US012383577B2

(12) United States Patent
Chen et al.

(10) Patent No.: US 12,383,577 B2
(45) Date of Patent: Aug. 12, 2025

(54) POLYSACCHARIDE COMPOUND WITH A DEFINED MOLECULAR STRUCTURE THAT CAN ELIMINATE THE TOXIC SIDE EFFECTS OF CHEMOTHERAPY DRUGS

(71) Applicant: SHENZHEN YANDAI INVESTMENT CO., LTD, Guangdong (CN)

(72) Inventors: Xuemin Chen, Guangdong (CN); Chunming He, Guangdong (CN); Guan Mo, Guangdong (CN); Jin Chen, Guangdong (CN); Yanjun Li, Guangdong (CN); Yao Chen, Guangdong (CN); Fengji Chen, Guangdong (CN); Mei Liang, Guangdong (CN); Zhe Fang, Guangdong (CN); Yuanye Su, Guangdong (CN)

(73) Assignee: SHENZHEN YANDAI INVESTMENT CO., LTD, Guangdong (CN)

( * ) Notice: Subject to any disclaimer, the term of this patent is extended or adjusted under 35 U.S.C. 154(b) by 0 days.

(21) Appl. No.: 19/012,840

(22) Filed: Jan. 7, 2025

(65) Prior Publication Data
US 2025/0134922 A1    May 1, 2025

Related U.S. Application Data

(63) Continuation of application No. PCT/CN2024/080442, filed on Mar. 7, 2024.

(30) Foreign Application Priority Data

Aug. 4, 2023  (CN) .......................... 202310984408.6

(51) Int. Cl.
| *A61K 36/00* | (2006.01) |
| *A61K 31/716* | (2006.01) |
| *A61K 33/243* | (2019.01) |
| *A61K 36/074* | (2006.01) |
| *A61P 35/00* | (2006.01) |
| *C08B 37/00* | (2006.01) |

(52) U.S. Cl.
CPC .......... *A61K 31/716* (2013.01); *A61K 33/243* (2019.01); *A61K 36/074* (2013.01); *A61P 35/00* (2018.01); *C08B 37/0024* (2013.01); *A61K 2236/13* (2013.01); *A61K 2236/15* (2013.01); *A61K 2236/17* (2013.01); *A61K 2236/331* (2013.01); *A61K 2236/37* (2013.01); *A61K 2236/51* (2013.01)

(58) Field of Classification Search
CPC .................................................. A61K 36/074
See application file for complete search history.

(56) References Cited

U.S. PATENT DOCUMENTS

| 2005/0282773 A1 | 12/2005 | Platt |
| 2008/0112967 A1 | 5/2008 | Feng et al. |
| 2017/0028003 A1 | 2/2017 | Ko et al. |

FOREIGN PATENT DOCUMENTS

| CN | 1513881 | 7/2004 |
| CN | 101357951 | 2/2009 |
| CN | 101367881 | 2/2009 |
| CN | 101857645 | 10/2010 |
| CN | 102617745 | 8/2012 |
| CN | 105175575 | 12/2015 |
| CN | 107857828 | 3/2018 |
| CN | 108250320 | 7/2018 |
| CN | 108976314 | 12/2018 |
| CN | 109021126 | 12/2018 |
| CN | 111410699 | 7/2020 |
| CN | 111533823 | 8/2020 |
| CN | 112094358 | 12/2020 |
| CN | 116077460 | 5/2023 |
| CN | 117186259 | 12/2023 |
| JP | S60188402 | 9/1985 |
| JP | 2016525552 | 8/2016 |

(Continued)

OTHER PUBLICATIONS

Li et al, Purification, structural characterization, and immunomodulatory activity of the polysaccharides from Ganoderma lucidum. International Journal of Biological Macromolecules (2019), vol. 143, pp. 806-813 (Year: 2019).*

Lili Cao et al., "Study on Extraction of Polysaccharides from Ganoderma lucidum by Hot Compressed Water and Its Antioxidant Activities", Journal of Food Science and Technology, Mar. 2018, with English abstract, pp. 58-62 and 67, vol. 36, No. 2.

Qun Dong et al., "A novel water-soluble b-D-glucan isolated from the spores of Ganoderma lucidum", Carbohydrate Research, Mar. 6, 2012, pp. 100-105, vol. 353.

Ting-Ting Wang et al., "Progress of Functional Research on the Polysaccharide Activity of Ganoderma lucidum", Edible Fungi of China, Dec. 31, 2022, with English abstract, pp. 7-16, vol. 41, No. 1.

(Continued)

*Primary Examiner* — Qiuwen Mi
(74) *Attorney, Agent, or Firm* — JCIPRNET

(57) ABSTRACT

This invention pertains to the field of plant extraction and separation technology, and provides a polysaccharide compound with a defined molecular structure that possesses antitumor efficacy. The polysaccharide compound is intended for the treatment of advanced cancer patients (those who are no longer candidates for surgery, have a life expectancy of only three to six months, and are still eligible for chemotherapy). The molecular formula is: $(C_{30}H_{50}O_{25})_n$. The active ingredient, polysaccharide, is obtained through the extraction of effective components from *Ganoderma lucidum* under high temperature and high pressure. The polysaccharide with this active ingredient, characterized by its water solubility, is readily absorbed by the human body, offers antitumor effects, and has proven efficacy in the prevention of tumor development in humans.

13 Claims, 33 Drawing Sheets

(56) References Cited

FOREIGN PATENT DOCUMENTS

| WO | 2018023857 | 2/2018 |
|----|------------|--------|
| WO | 2022062380 | 3/2022 |

OTHER PUBLICATIONS

Jin-Zhe He et al., "Study on the Structure and Constituents of Polysaccharide from Ganoderma Lucidum", Spectroscopy and Spectral Analysis, Jan. 2010, with English abstract, pp. 123-127, vol. 30, No. 1.

Xiaochen Sui et al., "Structure Features and Monosaccharide Composition of the Intracellular Polysaccharide from Submerge-Cultured Ganoderma lucidum", Journal of Food Science and Biotechnology, Dec. 31, 2016, with English abstract, pp. 728-733, vol. 35, No. 7.

"International Search Report (Form PCT/ISA/210) of PCT/CN2024/080442", mailed on Jun. 7, 2024, pp. 1-4.

"Written Opinion of the International Searching Authority (Form PCT/ISA/237) of PCT/CN2024/080442", mailed on Jun. 7, 2024, pp. 1-5.

\* cited by examiner

```
                                    ┌─ S1
┌─────────────────────────────────────┴──────────────────────────────────┐
│  Dusting and drying Ganoderma lucidum, then crushing Ganoderma          │
│         lucidum to make Ganoderma lucidum powder                        │
└─────────────────────────────────┬──────────────────────────────────────┘
                                  │ ┌─ S2
                                  ▼
┌────────────────────────────────────────────────────────────────────────┐
│  Placing the crushed Ganoderma lucidum in a sealed container mixed     │
│   with water, heating under high temperature and pressure to fully     │
│    dissolve the Ganoderma lucidum powder with the water into a         │
│                       medicinal juice solution                          │
└─────────────────────────────────┬──────────────────────────────────────┘
                                  │ ┌─ S3
                                  ▼
┌────────────────────────────────────────────────────────────────────────┐
│ Using membrane concentration technology to separate the medicinal      │
│   juice solution to obtain a concentrated solution with an active      │
│         ingredient and not fully dissolved medicinal residue           │
└─────────────────────────────────┬──────────────────────────────────────┘
                                  │ ┌─ S4
                                  ▼
┌────────────────────────────────────────────────────────────────────────┐
│  Mixing the concentrated solution containing the active ingredient     │
│    with pure water to a water solution with a preset concentration,    │
│  followed by multiple column chromatography separations to obtain      │
│    the Ganoderma lucidum polysaccharide GLP-2 with the active          │
│                              ingredient                                 │
└────────────────────────────────────────────────────────────────────────┘
```

FIG. 1

 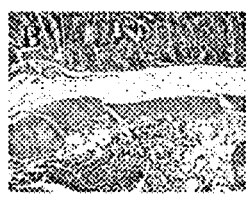 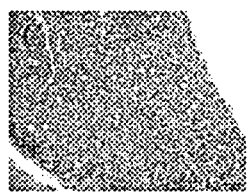 
FIG. 41A  FIG. 41B  FIG. 41C  FIG. 41D
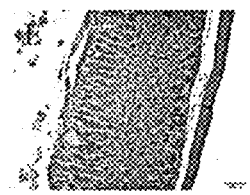 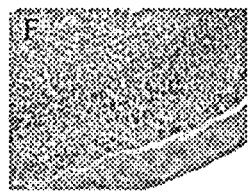 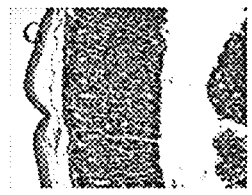
FIG. 41E  FIG. 41F  FIG. 41G

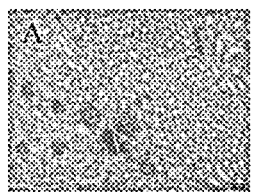 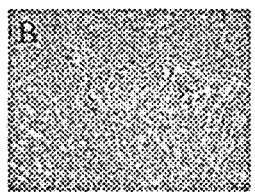 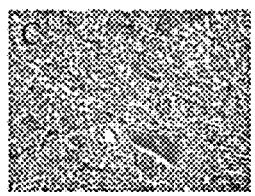 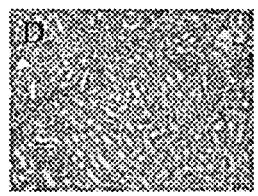
FIG. 42A  FIG. 42B  FIG. 42C  FIG. 42D
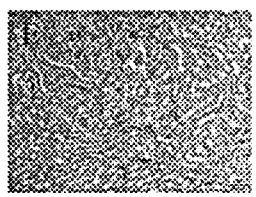 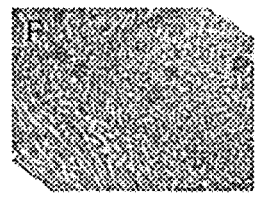 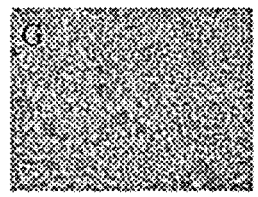
FIG. 42E  FIG. 42F  FIG. 42G

POLYSACCHARIDE COMPOUND WITH A DEFINED MOLECULAR STRUCTURE THAT CAN ELIMINATE THE TOXIC SIDE EFFECTS OF CHEMOTHERAPY DRUGS

CROSS-REFERENCE TO RELATED APPLICATION

This application is a continuation of international application of PCT application serial no. PCT/CN2024/080442, filed on Mar. 7, 2024, which claims the priority benefit of China application no. 202310984408.6 filed on Aug. 4, 2023. The entirety of each of the above-mentioned patent applications is hereby incorporated by reference herein and made a part of this specification.

TECHNICAL FIELD

This invention relates to the field of plant extraction and separation technology, particularly to the extraction of a polysaccharide compound from Ganoderma lucidum with a defined molecular structure that possesses antitumor efficacy and can mitigate the toxic side effects of chemotherapy drugs.

RELATED ART

*Ganoderma lucidum* is a type of fungal plant with a long history of medicinal use in China and Japan. *Ganoderma lucidum* has a plurality of complex active ingredients, and over 150 compounds have been isolated from it, such as polysaccharides, triterpenes, sterols, alkaloids, furan derivatives, amino peptides, and inorganic elements. Geographic location (longitude and latitude), seed variation, growth environment, and differences in temperature, humidity, and light intensity can significantly affect the content, proportion, and presence of an active ingredient referred to in this invention in *Ganoderma lucidum*.

SUMMARY OF INVENTION

This invention provides a polysaccharide compound with a defined molecular structure that has antitumor efficacy and can eliminate the toxic side effects of chemotherapy drugs.

This invention aims to address the unmet international challenges of treating patients with advanced cancer, where "patients with advanced cancer" are defined as: those who are no longer surgical candidates, have a life expectancy of only three to six months, and are still eligible for chemotherapy; the "challenges of treating patients" refer to: allowing patients with advanced cancer to regain their appetite quickly (typically within two to three weeks), reducing or stabilizing tumor size, and using in combination with chemotherapy drugs to essentially eliminate the toxic side effects induced by the chemotherapy drugs on the human body. Long-term combination use with the chemotherapy drugs can achieve the objective of substantially eradicating cancer cells or keeping the number of cancer cells within safe limits for high-quality human survival.

Another important function of the active ingredients specified in this invention is the prevention of mutations in normal human cells and the prevention of cancer cell formation.

Furthermore, the active ingredient in this invention, when used in combination with the chemotherapy drugs, exhibit exceptionally good therapeutic effects on lung cancer, liver cancer, and breast cancer, demonstrating a certain degree of broad-spectrum activity.

The invention provides a method for extracting *Ganoderma lucidum* polysaccharide GLP-2, comprising the steps of:

S1. dusting and drying *Ganoderma lucidum*, then crushing *Ganoderma lucidum* to make *Ganoderma lucidum* powder;

S2. placing the crushed *Ganoderma lucidum* powder in a sealed container mixed with water, heating under high temperature and pressure to fully dissolve the *Ganoderma lucidum* powder with the water into a medicinal juice solution;

S3. using membrane concentration technology to separate the medicinal juice solution to obtain a concentrated solution with an active ingredient and not fully dissolved medicinal residue; and S4. mixing the concentrated solution containing the active ingredient with pure water to a water solution with a preset concentration, followed by multiple column chromatography separations to obtain the *Ganoderma lucidum* polysaccharide GLP-2 with the active ingredient.

A further aspect of the invention: In step S2, the mixture of the *Ganoderma lucidum* powder and the water in the sealed container is fully stirred and heated at a high temperature to 105-200° C., with boiling time lasting for 2-6 h, during which the internal pressure in the sealed container gradually increases as the heating temperature rises, forming a high-temperature and high-pressure environment within the sealed container.

A further aspect of the invention: In step S2, the mixture of the *Ganoderma lucidum* powder and the water in the sealed container is heated at a high temperature to 105-170° C., with boiling time lasting for 3-6 h, during which the internal pressure in the sealed container gradually increases as the heating temperature rises, forming the high-temperature and high-pressure environment within the sealed container.

A further aspect of the invention: In step S4, the concentrated liquid containing the active ingredient is mixed with the pure water at a concentration ratio of 1:2 to 1:5.

A further aspect of the invention: In step S3, *Ganoderma lucidum* residue is removed from the extracted water solution containing the active ingredient by using the membrane concentration technology, obtaining a concentrated liquid or paste containing the active ingredient.

A further aspect of the invention: In step S1, the *Ganoderma lucidum* is rinsed with clean water to remove surface dust and dried at 105° C., and the dried *Ganoderma lucidum* is crushed, with the crushed *Ganoderma lucidum* powder being larger than 60 mesh.

A further aspect of the invention: In step S2, the mixed liquid in the sealed container is heated at a high temperature to 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C., with boiling times of 2 h, 2.5 h, 3 h, 3.5 h, 4 h, 4.5 h, 5 h, 5.5 h, or 6 h, during which the internal pressure in the sealed container gradually increases as the heating temperature rises, forming the high-temperature and high-pressure environment within the sealed container.

The invention also provides the *Ganoderma lucidum* polysaccharide GLP-2, wherein the structural formula of the *Ganoderma lucidum* polysaccharide GLP-2 is

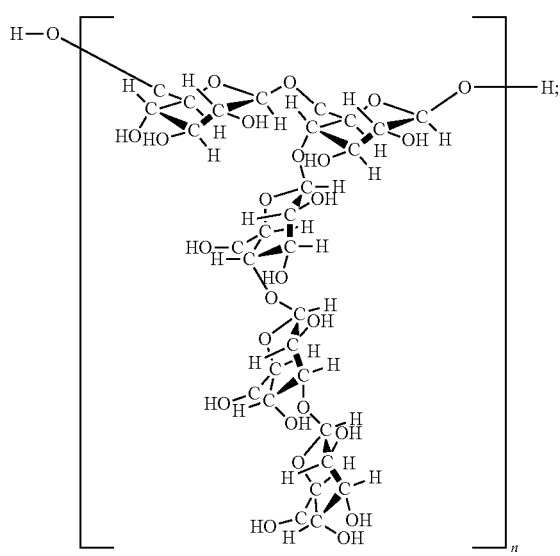

the molecular formula is $(C_{30}H_{50}O_{25})_n$, where n=92–147.

A further aspect of the invention: n is 92, 96, 100, 105, 110, 115, 120, 125, 130, 135, 140, 144, or 147.

This invention also provides the application of the *Ganoderma lucidum* polysaccharide GLP-2. The *Ganoderma lucidum* polysaccharide GLP-2 is characterized by its water solubility, is readily absorbed by the human body, offers antitumor effects, and has proven strong efficacy in the prevention of tumor development in humans. Notably, when used in combination with chemotherapy drugs, it can alleviate toxic side effects caused by the chemotherapy drugs on the human body, control and reduce tumor masses, and reduce and eliminate cancer cells.

The beneficial effects of this invention include a simple extraction process, high polysaccharide yield, low production cost, and ease of operation. The resultant *Ganoderma lucidum* polysaccharide is highly soluble and readily absorbed by the human body, enhancing its antitumor effects.

BRIEF DESCRIPTION OF DRAWINGS

FIG. 1: Flowchart of the method for extracting *Ganoderma lucidum* polysaccharide GLP-2, provided by an embodiment of the invention.

FIG. 41A to FIG. 41G: Schematic diagram of the effect of *Ganoderma lucidum* polysaccharide GLP-2 combined with chemotherapy on the stomach of orthotopic H22-bearing mice (×200), provided by an embodiment of the invention.

FIG. 42A to FIG. 42G: Schematic diagram of the effect of *Ganoderma lucidum* polysaccharide GLP-2 combined with chemotherapy on the kidneys of orthotopic H22-bearing mice (×200), provided by an embodiment of the invention.

DESCRIPTION OF EMBODIMENTS

Figure 2:
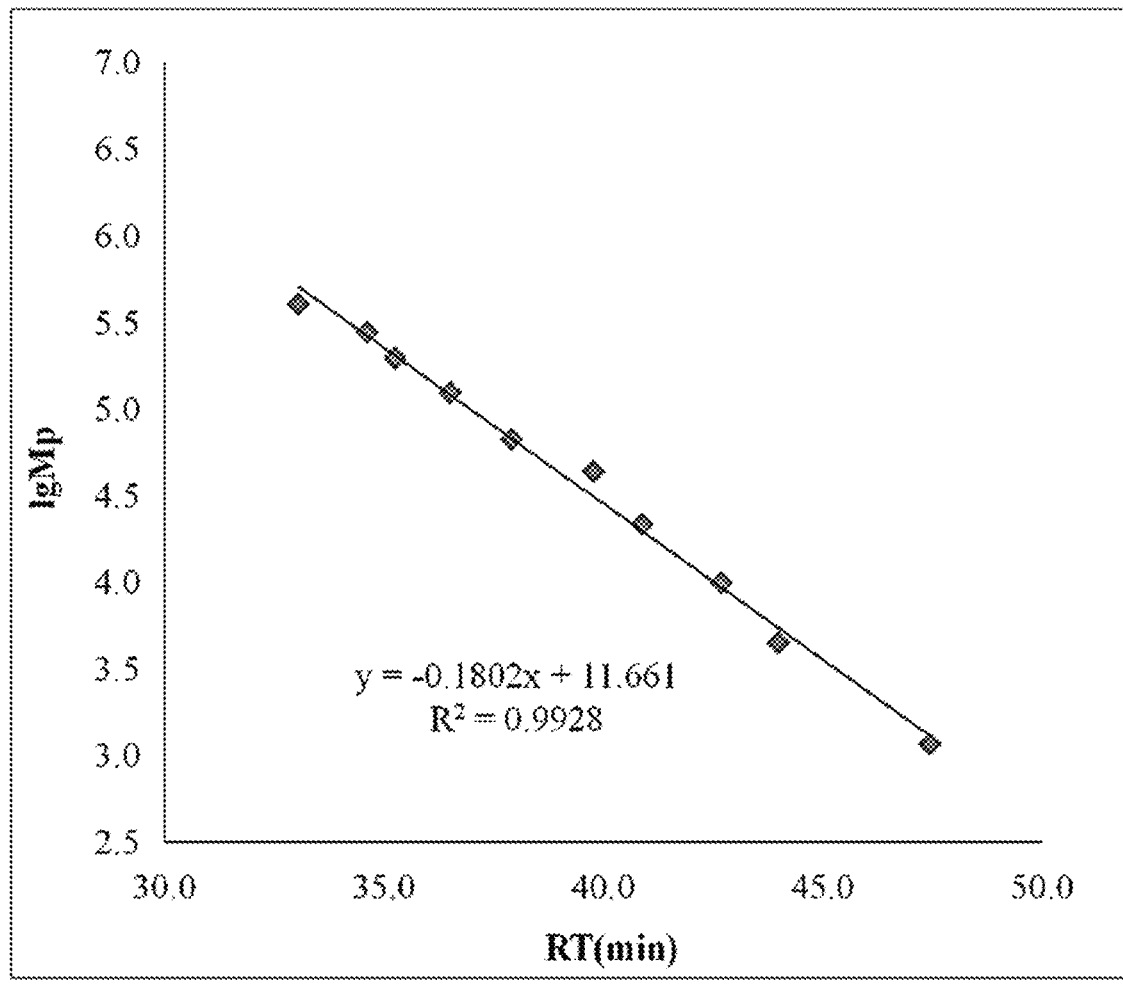
FIG. 2: Schematic diagram of lgMp-RT (peak molecular weight) calibration curves provided by an embodiment of the invention.

Embodiments of the present invention are described in detail below, and examples of the embodiments are shown in the drawings, wherein the same or similar reference numerals denote the same or similar elements or elements having the same or similar functions throughout. The embodiments below described by reference to the drawings are exemplary and are intended for the purpose of explaining the invention and should not be construed as limiting the scope of the invention.

As shown in FIG. 1, the present invention provides a flowchart for the method for extracting the *Ganoderma lucidum* polysaccharide GLP-2, described in detail as follows:

In step S1, harvested *Ganoderma lucidum*, either raw or having undergone preliminary processing, is washed with clean water in washing equipment to remove surface dust. After dust removal, the *Ganoderma lucidum* is transferred to drying equipment for high-temperature drying at a temperature of 105° C. The dried *Ganoderma lucidum* is then placed in a crusher or mill to be broken down into *Ganoderma lucidum* powder. The crushed *Ganoderma lucidum* powder is sieved, and particles of the *Ganoderma lucidum* powder larger than 60 mesh are screened out, while particles of the *Ganoderma lucidum* powder smaller than 60 mesh are returned to the crusher or mill for further crushing. This process is repeated multiple times until the crushed *Ganoderma lucidum* powder meets specified requirements.

In step S2, the *Ganoderma lucidum* powder that meets the requirements is mixed with pure water and placed in a sealed container. The sealed container is heated, in which the temperature is continuously increased to create a high-temperature, high-pressure environment, facilitating the thorough dissolution of the *Ganoderma lucidum* powder with the water to form a mixed solution. The sealed container is heated to a temperature between 105° C. and 200° C., with a boiling time of 2-6 h, preferably between 105° C. and 170° C., for 3-6 h. More preferably, the heating occurs at temperatures of 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C., with a boiling time of 2 h, 2.5 h, 3 h, 3.5 h, 4 h, 4.5 h, 5 h, 5.5 h, or 6 h, allowing the thorough dissolution. The sealed container is a reaction kettle.

In step S3, the water solution extracted, containing the active ingredient, is centrifuged to remove residues. The medicinal liquid is then concentrated using membrane concentration technology to obtain a concentrated liquid.

In step S4, the concentrated liquid containing the active ingredient is prepared at a specific concentration, separated by column chromatography, and then concentrated and lyophilized to obtain *Ganoderma lucidum* polysaccharide GLP-2 with the active ingredient.

This method offers a simple extraction process, high polysaccharide yield, low production costs, and simple operation.

The invention also provides the *Ganoderma lucidum* polysaccharide GLP-2, wherein the structural formula of the *Ganoderma lucidum* polysaccharide GLP-3 is

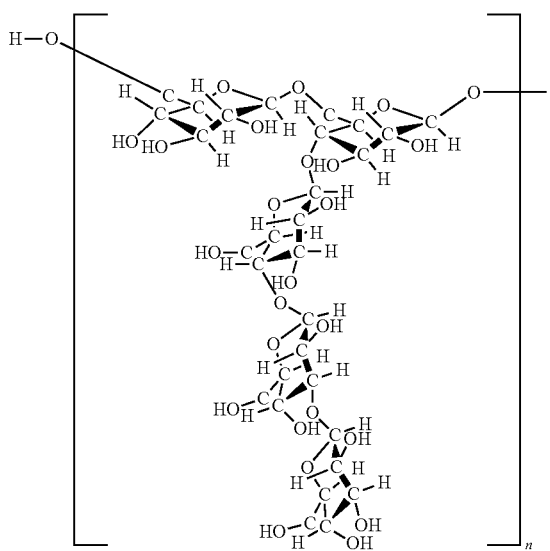

the molecular formula is $(C_{30}H_{50}O_{25})_n$, where $n=92-147$.

Following the acquisition of the *Ganoderma lucidum* polysaccharide GLP-2 with the aforementioned structure, assay experiments were conducted and the following results are reported herein.

I. MOLECULAR WEIGHT DETERMINATION

1. Experimental Objective

To determine the molecular weight and purity of the polysaccharide using HPGPC.

2. Experimental Materials

2.1 Equipment

| Equipment name | Manufacturer | Model |
|---|---|---|
| High-performance liquid chromatography | Shimadzu | LC-10A |
| Differential refractometer | Shimadzu | RI-10A |
| BRT105-104-102 tandem gel permeation chromatography column | BoRui Saccharide | BRT105-104-102 (8 × 300 mm) |
| Electronic scale | Sartorius | CPA225D |
| Centrifuge | Eppendorf | Eppendorf5424 |
| Pipette | Sartorius | 200 uL, 1,000 uL |

2.2 Materials

| Reagent | Manufacturer | Batch No. | Catalog No. | Grade | Shelf life |
|---|---|---|---|---|---|
| NaCl | ACROS | A0356762 | 139725000 | ACROS | 2022 |

2.3 Standards

| Standard | Manufacturer | Batch No. | Storage conditions | Purity | Shelf life |
|---|---|---|---|---|---|
| Dextranstandards1152 | Yuanye Bio-Technology | A16A8L41850 | Seal and store | 99% | 2 years |
| 5000 | Sigma | 102084138 | Seal and store | ≥99% | 2 years |
| 11600 | Sigma | 102136543 | Seal and store | 99% | 2 years |
| 23800 | Sigma | 102124529 | Seal and store | ≥97% | 2 years |
| 48600 | Sigma | 102104509 | Seal and store | ≥99% | 2 years |
| 80900 | Sigma | 102108375 | Seal and store | >98% | 2 years |
| 148000 | Sigma | 102089360 | Seal and store | >98% | 2 years |
| 273000 | Sigma | 102110878 | Seal and store | 98% | 2 years |
| 409800 | Sigma | 102124507 | Seal and store | >98% | 2 years |
| 667800 | Sigma | 102104510 | Seal and store | >98% | 2 years |

Molecular weight is measured in Daltons (Da).

3. Experimental Procedure

3.1 Reagent Preparation

| Reagent name | Preparation method | Storage conditions | Shelf life |
|---|---|---|---|
| 0.05M NaCl solution | Precisely prepared, filtered through a 0.45-μm membrane, degassed by sonication for 10 min | RT | 1 month |

3.2 Preparation of Sample and Standard Solutions

Samples and standards were precisely weighed to prepare a 5 mg/mL solution, which was centrifuged at 12,000 rpm for 10 min, and the supernatant was filtered through a 0.22-μm micropore filter. Then the sample was transferred to a 1.8-mL sample vial.

3.3 Chromatographic Method

Column: BRT105-104-102 tandem gel permeation chromatography column (8×300 mm); Mobile phase: 0.05 M NaCl solution; Flow rate: 0.6 mL/min; Column temperature: 40° C.; Injection volume: 20 μL; Detector: Differential refractometer RI-10A.

4. Experimental Results

Figure 3:
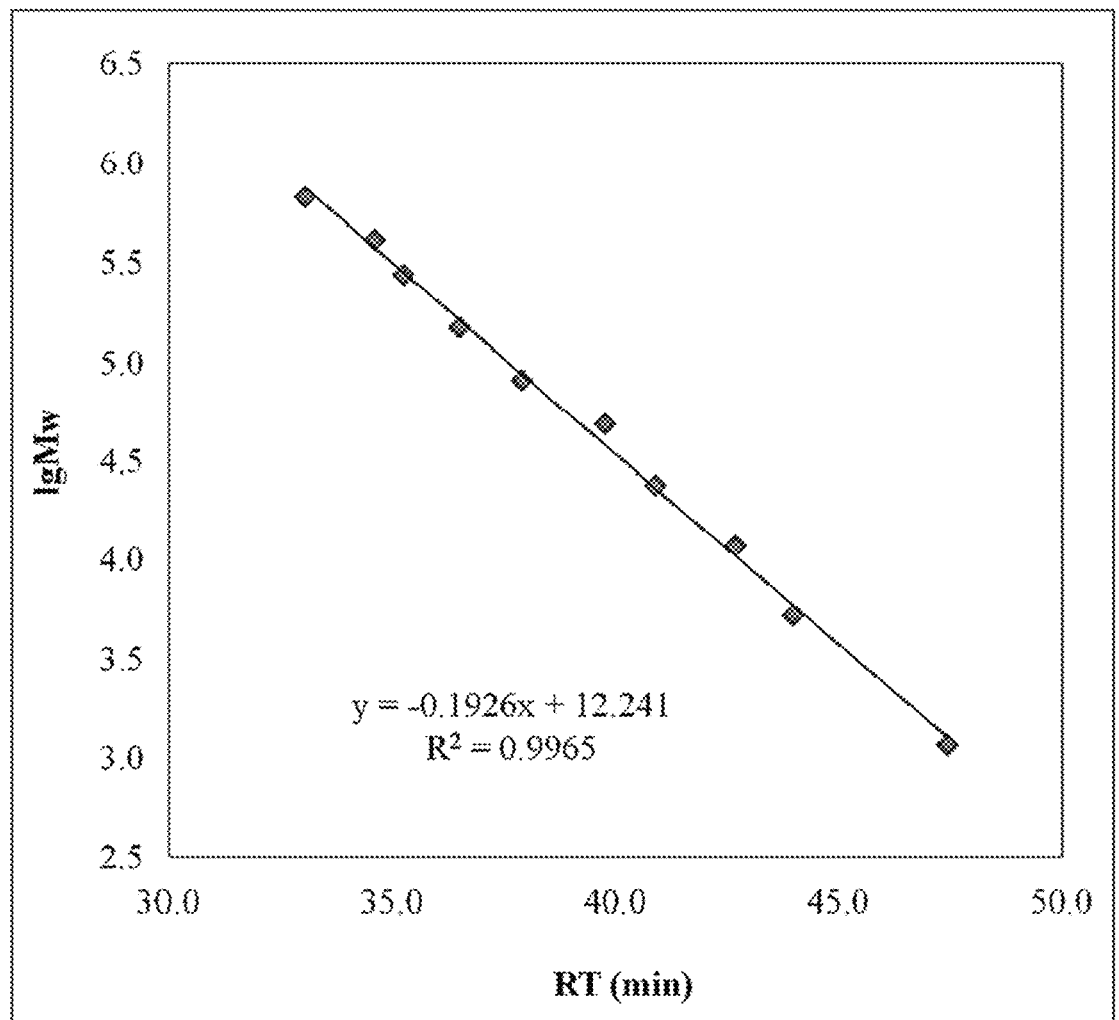
FIG. 3: Schematic diagram of lgMp-RT (weight-average molecular weight) calibration curvew provided by an embodiment of the invention.
Figure 4:
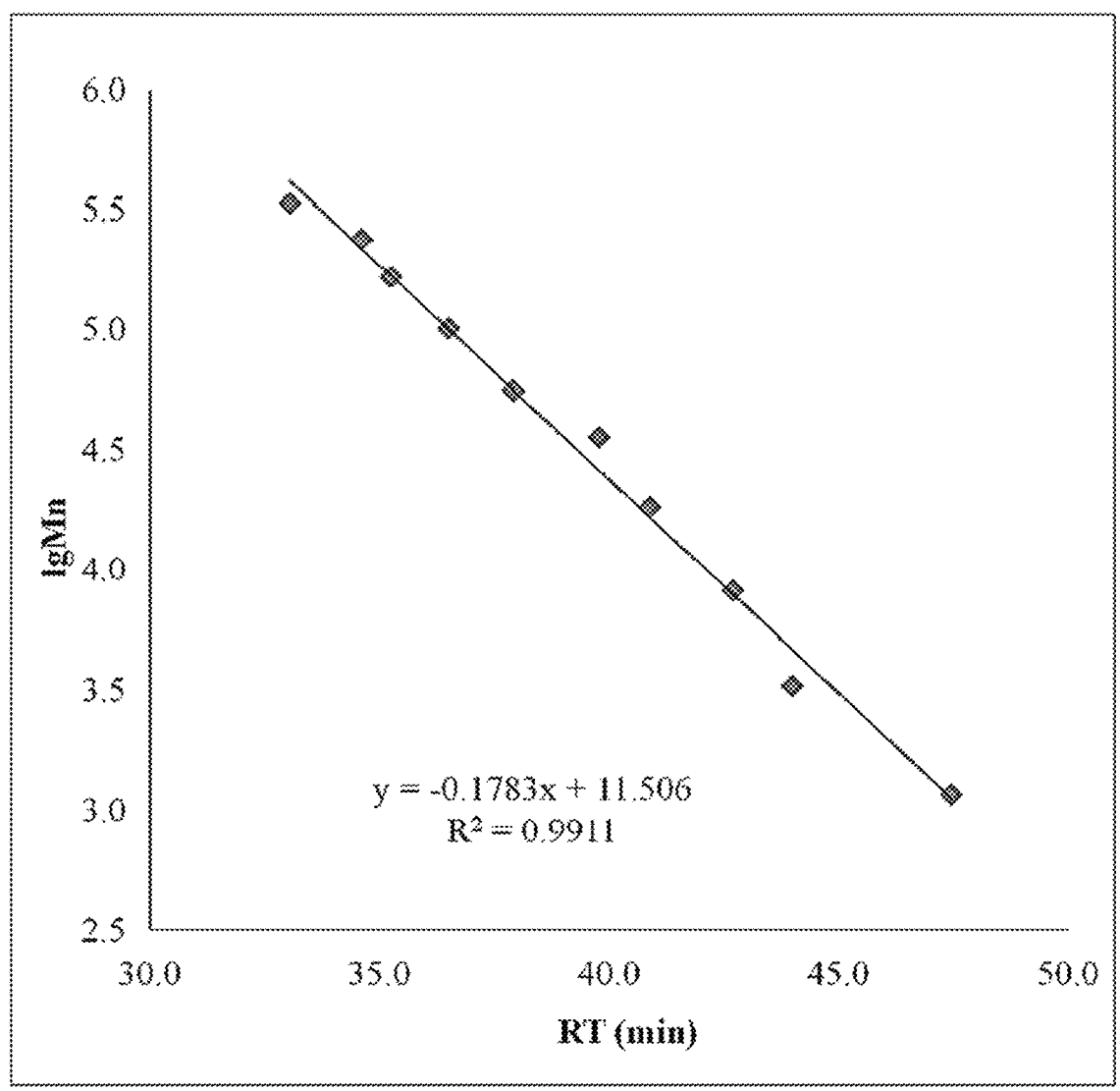
FIG. 4: Schematic diagram of lgMp-RT (number-average molecular weight) calibration curves provided by an embodiment of the invention.

As shown in FIGS. 2-4, calibration curves for lgMp-RT (peak molecular weight), lgMw-RT (weight-average molecular weight), and lgMn-RT (number-average molecular weight) were obtained.

Figure 5:
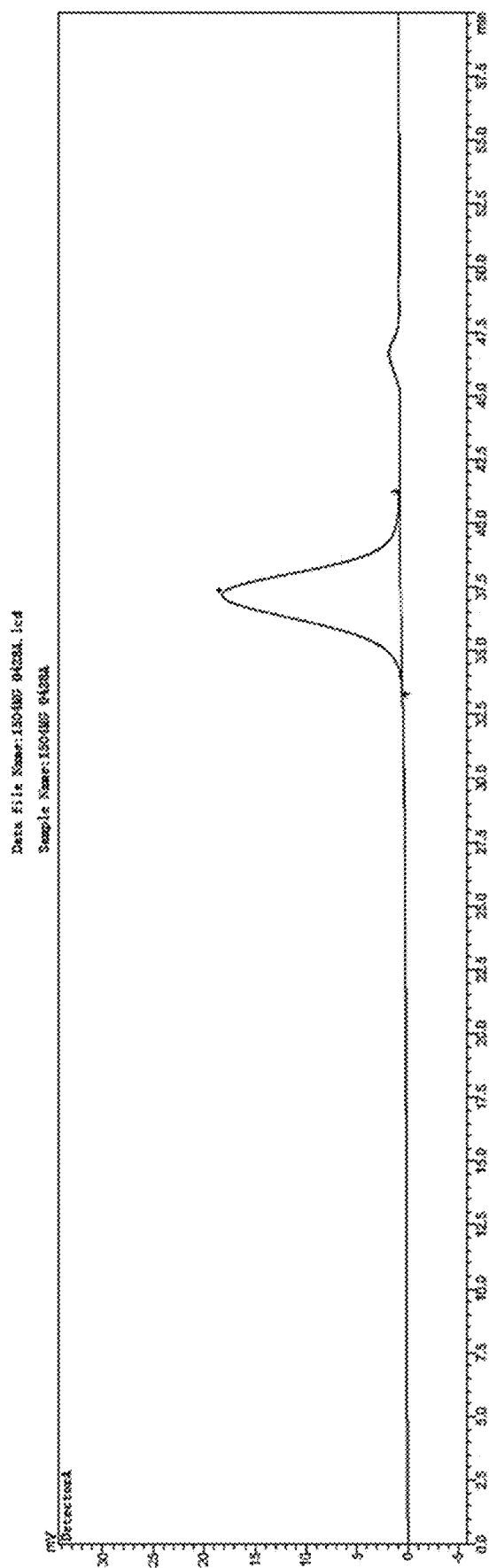
FIG. 5: Schematic diagram of the molecular weight of *Ganoderma lucidum* polysaccharide GLP-2, provided by an embodiment of the invention.

The equation of the calibration curves for lgMp-RT is: $y=-0.1082x+11.661 R^2=0.9928$;

The equation of the calibration curves for lgMw-RT is: $y=-0.1926x+12.241 R^2=0.9965$;

The equation of the calibration curves for lgMn-RT is: $y=-0.1783x+11.506 R^2=0.9911$;

Using the standard curves, a formula was derived to calculate the molecular weight of each sample. The molecular weight chromatograms for the samples are shown in FIG. 5, with the results detailed in the table below.

| Sample ID | RT (min) | lgMp | lgMw | lgMn | Mp | Mw | Mn | Peak Area Ratio (%) |
|---|---|---|---|---|---|---|---|---|
| | 37.199 | 5.0 | 5.1 | 4.9 | 90728 | 119254 | 74717 | 100 |

Note:
The peak at 46.5 min corresponds to the mobile phase.

II. MONOSACCHARIDE COMPOSITION DETERMINATION EXPERIMENT

1. Experimental Objective

To determine the monosaccharide composition using an ion chromatograph.

2. Experimental Principle

This method is based on the electrochemical activity of sugar molecules and their ionization in strong alkaline solutions. Sugar compounds are weak acids with a pKa greater than 11. In high pH eluents, they partially or fully exist as anions. Efficient anion exchange and separation of sugar compounds is achieved, which leverages differences in ion exchange due to variations in pKa of different sugars, as well as differences in hydrophobic interactions between some sugars and the anion exchange resin. Detection is then accomplished by measuring the current produced by the oxidation of hydroxyl groups in the sugar molecules at a gold electrode surface.

3. Experimental Materials

3.1 Equipment

| Equipment name | Manufacturer | Model |
|---|---|---|
| Ion chromatograph | ThermoFisher | ICS5000 |
| Electric thermostatic blast drying oven | LICHEN | 101-1BS |
| Nitrogen blower | LICHEN | UGC-24M |
| Electronic scale | Sartorius | BS 210 S |
| Centrifuge | ThermoFisher | D-37520 |
| Pipette | DRAGONLAB | 19050983 |

3.2 Reagents

| Reagent | Manufacturer | Batch No. | Catalog No. | Grade |
|---|---|---|---|---|
| Trifluoroacetic acid | ACROS | A0356762 | 139725000 | AR |
| 50% sodium hydroxide solution | Alfa Aesar | Z21E036 | 33382 | GR |
| Sodium acetate | ThermoFishe | 191126 | 059326 | GR |

3.3 Standards

| Standard | Manufacturer | Batch No. | Storage conditions | Purity |
|---|---|---|---|---|
| Mannose | Bo Rui Saccharide | C17D9H77586 | Seal and store | AR |
| Rhamnose | Bo Rui Saccharide | H10S9Z69863 | Seal and store | AR |
| Galacturonic acid | Bo Rui Saccharide | K02A9B66077 | Seal and store | AR |
| Galactose | Bo Rui Saccharide | E1927035 | Seal and store | AR |
| Glucose | Bo Rui Saccharide | Q18F10N80946 | Seal and store | AR |
| Glucuronic acid | Bo Rui Saccharide | K14M10S82777 | Seal and store | AR |
| Arabinose | Bo Rui Saccharide | S15A10G85850 | Seal and store | AR |
| Xylose | Bo Rui Saccharide | A22S6X3606 | Seal and store | AR |

-continued

| Standard | Manufacturer | Batch No. | Storage conditions | Purity |
|---|---|---|---|---|
| Fucose | Bo Rui Saccharide | X29D7Y27768 | Seal and store | AR |
| Glucosamine hydrochloride | Bo Rui Saccharide | A22S6X3606 | Seal and store | AR |
| N-acetyl-D-glucosamine | Bo Rui Saccharide | A21J8X40372 | Seal and store | AR |
| D-fructose | Bo Rui Saccharide | J01J10R89818 | Seal and store | AR |
| D-ribose | Bo Rui Saccharide | H26F10Z81556 | Seal and store | AR |
| Galactosamine hydrochloride | Bo Rui Saccharide | B01J8S37079 | Seal and store | AR |
| L-guluronic acid | Bo Rui Saccharide | S200115AG1 | Seal and store | ≥98% |
| D-mannuronic acid | Bo Rui Saccharide | S200108AM1 | Seal and store | ≥98% |

4. Experimental Methods

4.1 Reagent Preparation

| Reagent name | Preparation method | Storage conditions |
|---|---|---|
| 15 mM NaOH solution | 2.4 g of 50% NaOH solution, 2 L of water | RT |
| 15 mM NaOH & 100 mM NaOAc solution | 1.2 g of 50% NaOH solution, 8.2 g of NaOAc, 1 L of water | RT |

4.2 Preparation and Calculation Method for Standard Solutions

Standard stock solutions were prepared using 16 different monosaccharide standards (fucose, rhamnose, arabinose, galactose, glucose, xylose, mannose, fructose, ribose, galacturonic acid, glucuronic acid, glucosamine hydrochloride, galactosamine hydrochloride, N-acetyl-D-glucosamine, guluronic acid, and mannuronic acid).

Concentration standards of each monosaccharide standard solution were accurately prepared and used as a mixed standard. The mass of different monosaccharides was determined using an absolute quantification method and the molar ratios were calculated based on the molar mass of each monosaccharide.

4.3 Sample Preparation 5 mg of the sample was accurately weighed in an ampule. 2 mL of 3M TFA was added and hydrolyzed at 120° C. for 3 h. The acid hydrolysate was accurately transferred to a tube and evaporated to dryness under nitrogen. 5 mL water was added, vortexed to mix, and then 50 μL was taken and added to 950 μL of deionized water, and centrifuged at 12,000 rpm for 5 min. The supernatant was transferred for IC analysis.

4.4 Chromatographic Method

Column: Dionex Carbopac™ PA20 (3×150 mm); Mobile phase: A: $H_2O$; B: 15 mM NaOH; C: 15 mM NaOH & 100 mM NaOAc; Flow rate: 0.3 mL/min; Injection volume: 5 μL; Column temperature: 30° C.; Detector: Electrochemical detector.

4.5 Standard Series

| No. | Name | ppm | Name | RT | Area |
|---|---|---|---|---|---|
| 1 | Fucose | 5 | Fuc | 5.659 | 18.741 |
| 2 | Galactosamine hydrochloride | 3 | GalN | 10.084 | 23.888 |
| 3 | Rhamnose | 5 | Rha | 10.475 | 10.717 |
| 4 | Arabinose | 3.7 | Ara | 11.092 | 16.035 |
| 5 | Glucosamine hydrochloride | 5 | GlcN | 12.367 | 31.057 |
| 6 | Galactose | 5 | Gal | 13.767 | 17.597 |
| 7 | Glucose | 5 | Glc | 15.484 | 20.442 |
| 8 | N-acetyl-D-glucosamine | 5 | GlcNAc | 16.792 | 13.652 |
| 9 | Xylose | 5 | Xyl | 17.834 | 22.737 |
| 10 | Mannose | 5 | Man | 18.117 | 14.734 |
| 11 | Fructose | 15 | Fru | 20.534 | 12.857 |
| 12 | Ribose | 10 | Rib | 22.484 | 26.868 |
| 13 | Galacturonic acid | 5 | GalA | 45.125 | 8.815 |
| 14 | Guluronic acid | 10 | GulA | 45.950 | 20.824 |
| 15 | Glucuronic acid | 5 | GlcA | 48.509 | 11.689 |
| 16 | Mannuronic acid | 10 | ManA | 50.992 | 22.847 |

C (standard)/A (standard) = C (sample)/A (sample)

5. Experimental Results

Figure 6:
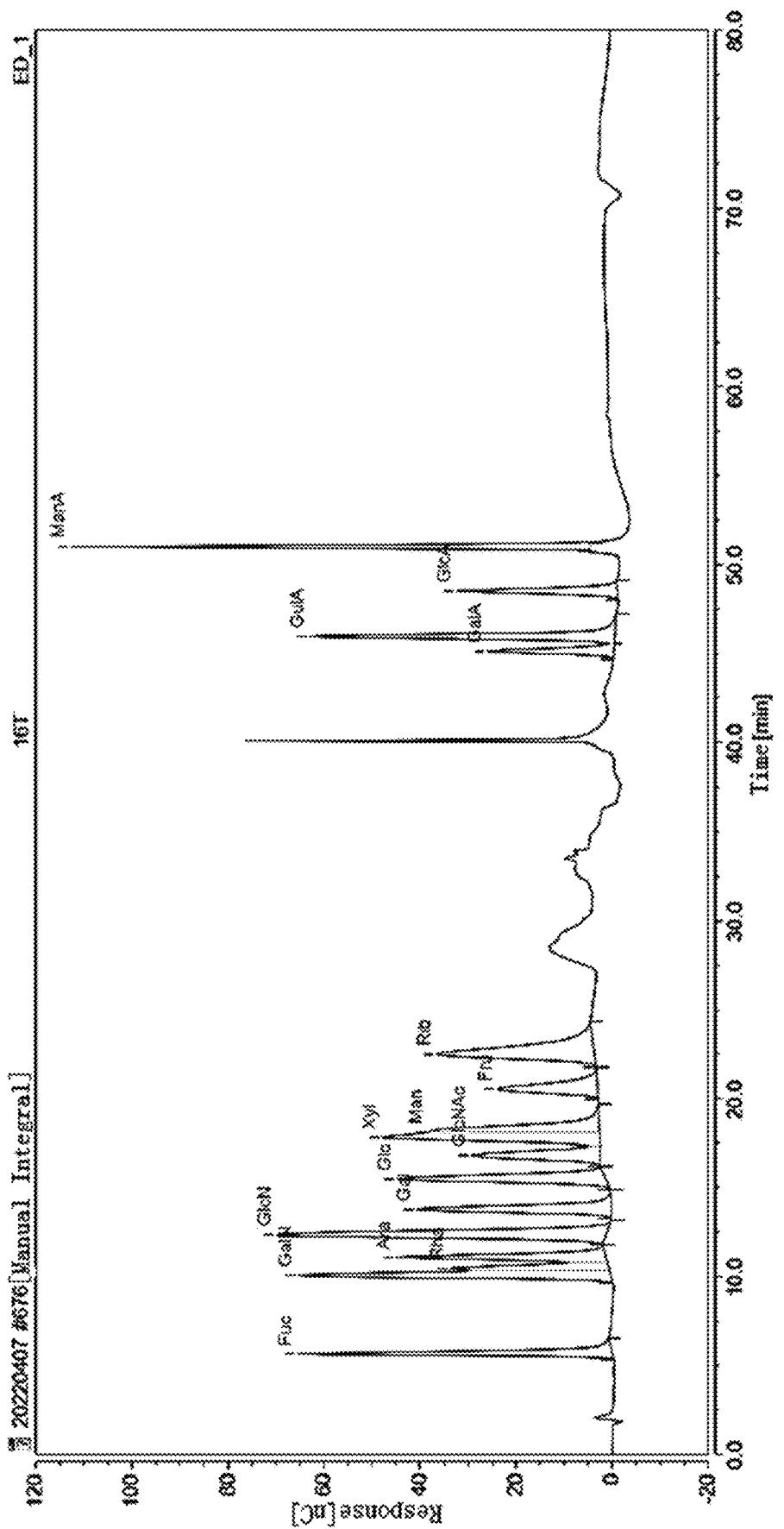
FIG. 6: Ion chromatography 1 of mixed standard 16 sugars, provided by an embodiment of the invention.
Figure 7:
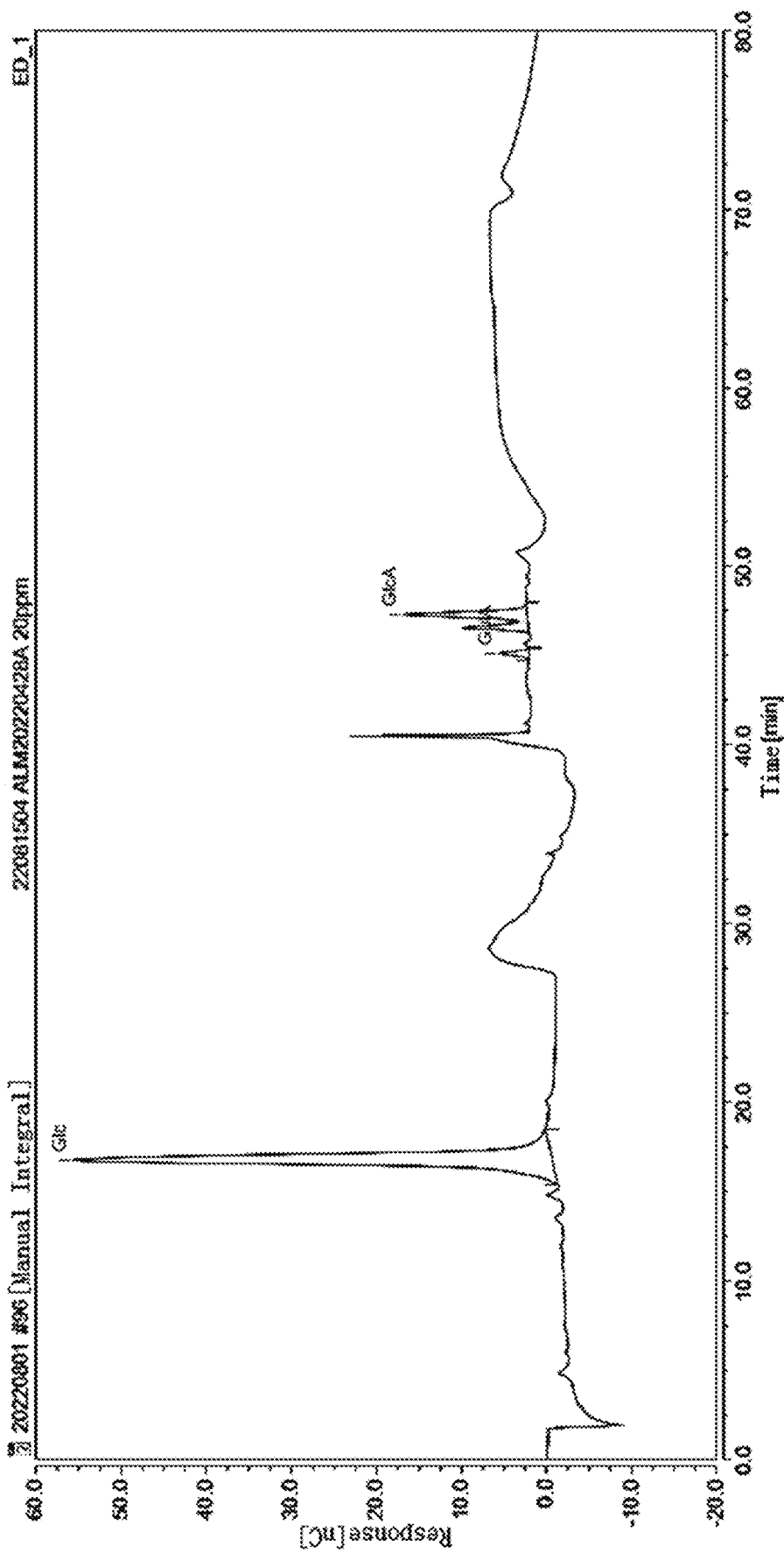
FIG. 7: Ion chromatography 2 of mixed standard 16 sugars, provided by an embodiment of the invention.

Mixed standard: Solvent peaks at 2.0 min for sodium hydroxide and at 41 min for sodium acetate, as shown in FIGS. 6 and 7.

| Name | RT | Molar Ratio |
|---|---|---|
| Fucose | 5.959 | 0.000 |
| Galactosamine hydrochloride | 10.817 | 0.000 |
| Rhamnose | 11.334 | 0.000 |
| Arabinose | 11.792 | 0.000 |
| Glucosamine hydrochloride | 13.384 | 0.000 |
| Galactose | 14.609 | 0.000 |
| Glucose | 16.759 | 0.789 |
| N-acetyl-D-glucosamine | 18.55 | 0.000 |
| Xylose | 19.209 | 0.000 |
| Mannose | 19.825 | 0.000 |
| Fructose | 22.259 | 0.000 |
| Ribose | 24.309 | 0.000 |
| Galacturonic acid | 44.592 | 0.000 |
| Guluronic acid | 45.092 | 0.042 |
| Glucuronic acid | 47.284 | 0.168 |
| Mannuronic acid | 50.2 | 0.000 |

III. EXPERIMENT ON THE DETERMINATION OF POLYSACCHARIDE LINKAGE

1. Experimental Objective

To determine the linkage patterns of polysaccharide samples through derivatization such as methylation by GC-MS analysis.

2. Experimental Materials

2.1 Equipment

| Equipment name | Manufacturer | Model |
|---|---|---|
| Rotary evaporator | Zhengzhou Greatwall Scientific Industrial and Trade Co., Ltd. | R-1001VN |
| Nitrogen blower | LICHEN | UGC-24M |
| Magnetic stirrer | DLAB | MS7-H550-Pro |
| Vacuum drying oven | LICHEN | 101-1BS |
| Gas chromatograph-mass spectrometer | Agilent | 6890-5973 |

2.2 Reagents

| Reagent | Manufacturer | Batch No. | Catalog No. | Grade |
|---|---|---|---|---|
| Trifluoroacetic acid | ACROS | A0356762 | 139725000 | AR |
| Methyl iodide | Adamas | P1345479 | 01111630 | AR |
| Sodium borohydride | Aldrich | MKCD7945 | 205591 | AR |
| Ethyl acetate | Vokai | 08050003 | 40065982 | AR |
| Acetic anhydride | HUSHI | 20170314 | 10000318 | AR |
| Perchloric acid | Aldrich | SHBF7833V | 311421 | AR |
| Acetic acid | Fisher | 156174 | A35-500 | AR |
| Methanol | Merck | 10941735810 | 67-56-1 | AR |
| Sodium hydroxide | HUSHI | 20150429 | 10019718 | AR |
| Dimethyl sulfoxide | Adamas | P1265087 | 759270 | AR |
| Sodium hydride | Adamas | P1306059 | 81778A | AR |
| Methylation kit | Borui Saccharide | BRT-2020JJH | BRT-JJH | AR |

3. Experimental Methods

3.1 Reagent Preparation

| Reagent name | Preparation method | Storage conditions |
|---|---|---|
| 3M trifluoroacetic acid | 1 V trifluoroacetic acid + 3 V water | Store in refrigerator at 5° C. |
| Sodium hydride dry powder | 60% sodium hydride washed with hexane | Store dry at room temperature |
| Sodium borodeuteride and sodium hydroxide solution | 20 mg + 20 mM NaOH solution | Seal and store |
| 20% acetic acid methanol solution | 1 V glacial acetic acid + 4 V water | Store in refrigerator at 5° C. |
| Polysaccharide methylation kit | A: anhydrous alkaline solution B: methyl iodide solution | Store in refrigerator at 5° C. |

3.2 Sample Methylation

The sample underwent methylation, hydrolysis, and acetylation, followed by GC-MS analysis, which was compared with the standard mass spectral library.

2-3 mg of the polysaccharide sample was weighed and placed in a glass reaction vial, 1 mL of anhydrous DMSO was added, and methylation reagent A was added rapidly. The solution was sealed and dissolved under ultrasonication, then methylation reagent B was added. The reaction was allowed at 30° C. in a magnetic stirring water bath for 60 min. Finally, 2 mL of ultrapure water was added to stop the methylation reaction.

The methylated polysaccharide was taken, 1 mL of 2M trifluoroacetic acid (TFA) was added, and hydrolyzed for 90 min. The rotary evaporator was used to dry. 2 mL of double-distilled water was added to the residue, which was reduced with 60 mg of sodium borohydride for 8 h, neutralized with glacial acetic acid, and evaporated using the rotary evaporator. Then, it was dried in a 101° C. oven, then 1 mL of acetic anhydride was added for acetylation and reacted at 100° C. for 1 h, and cooled. Then 3 mL of toluene was added, vacuum concentrated to dry, and this process was repeated 4-5 times to remove excess acetic anhydride.

The acetylated product was dissolved in 3 mL of $CH_2Cl_2$ and transferred to a separatory funnel. A small amount of distilled water was added and shaken thoroughly, then the upper aqueous layer was removed. This process was repeated four times. The $CH_2Cl_2$ layer was dried with an adequate amount of anhydrous sodium sulfate, brought to a volume of 10 mL, and placed in a vial for liquid analysis. The acetylated sample was analyzed using a Shimadzu GCMS-QP 2010 gas chromatograph-mass spectrometer.

GC-MS Conditions: RXI-5 SIL MS column 30 m×0.25 mm×0 0.25 μm; Temperature program: started at 120° C., increased at 3° C./min to 250° C., held for 5 min; Injector temperature at 250° C., detector temperature at 250° C., carrier gas was helium, flow rate was 1 mL/min.

4. Experimental Results

Figure 8:
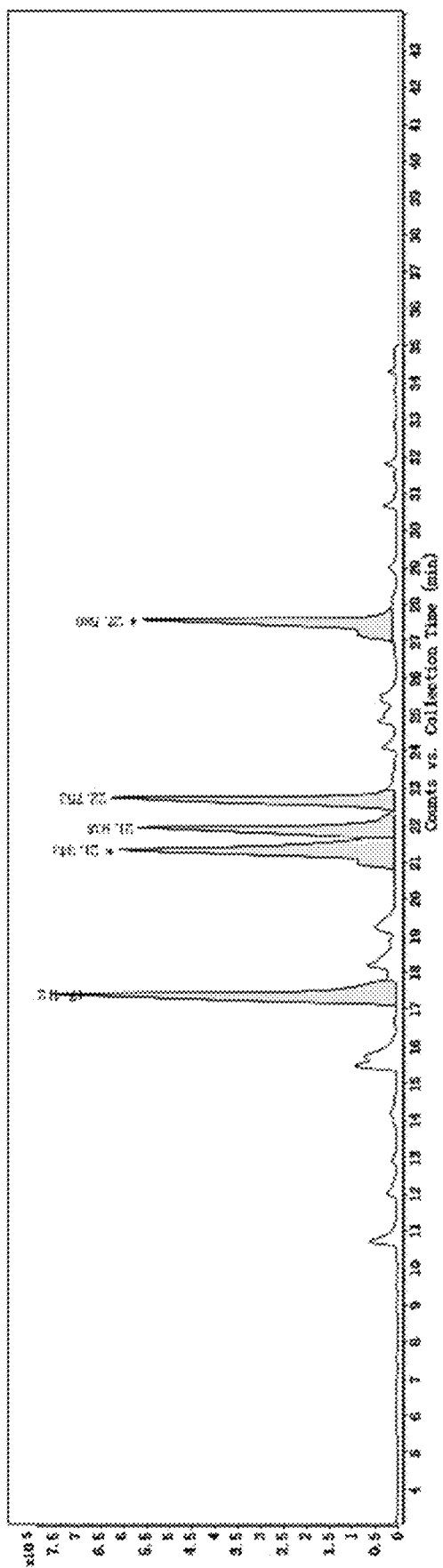
FIG. 8: GCMS chromatogram of the *Ganoderma lucidum* polysaccharide GLP-2 (PMAA) provided by an embodiment of the invention.
Figure 9:
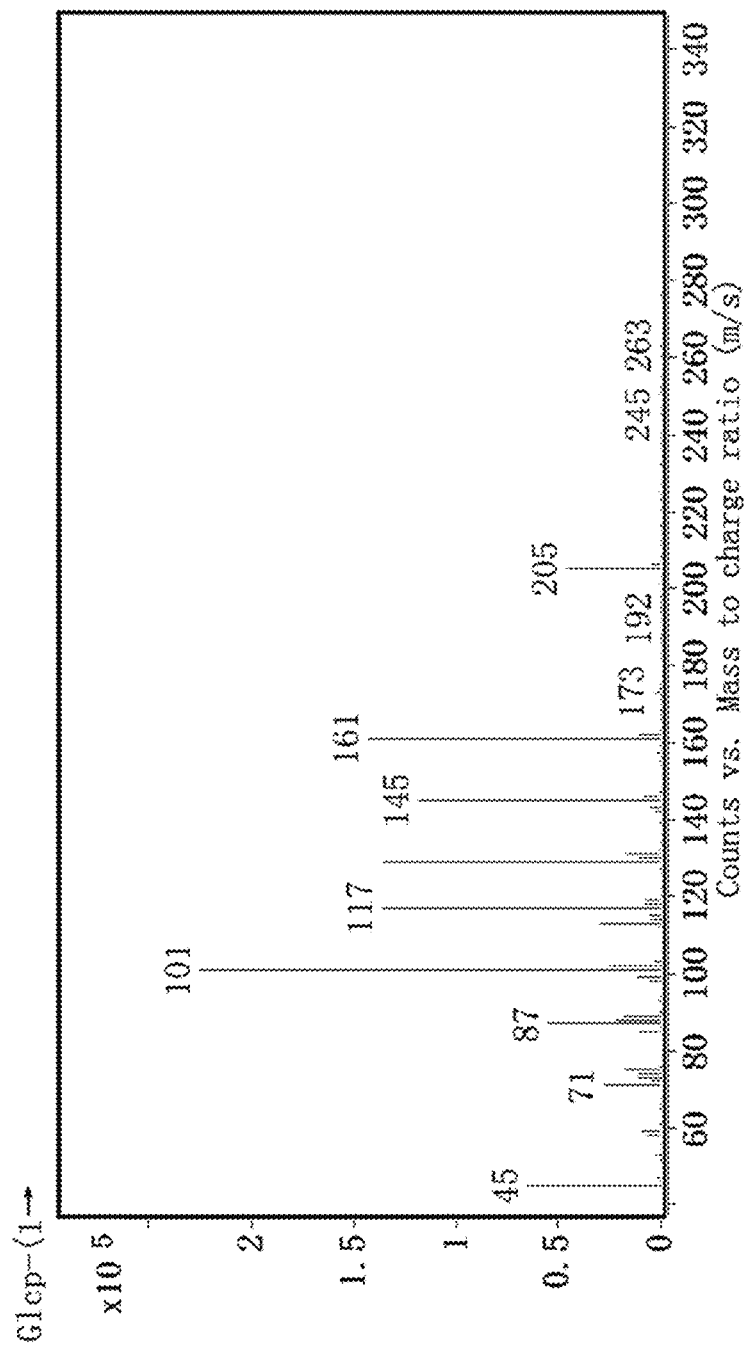
FIG. 9: Schematic diagram 1 of the mass-to-charge ratio analysis results of permethylated alditol acetate (PMAA) of polysaccharide, provided by an embodiment of the invention.
Figure 10:
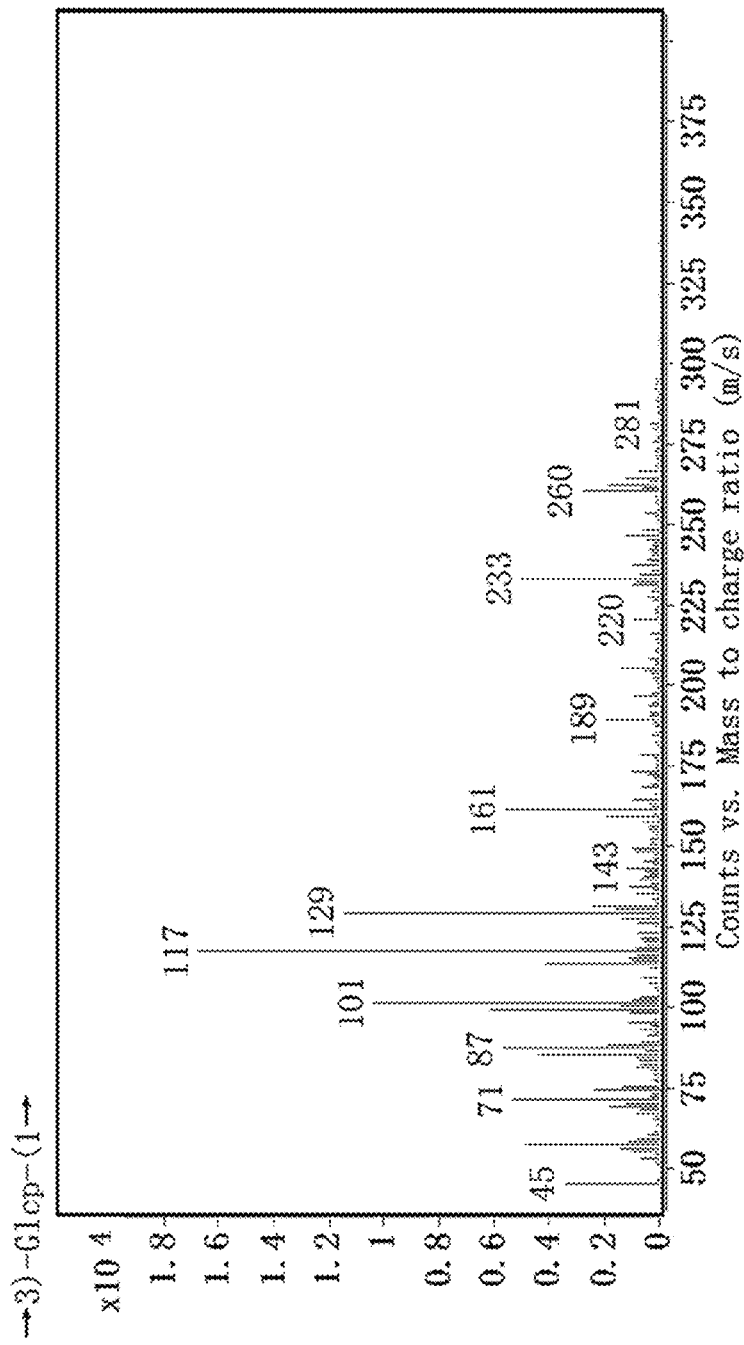
FIG. 10: Schematic diagram 2 of the mass-to-charge ratio analysis results of permethylated alditol acetate (PMAA) of polysaccharide, provided by an embodiment of the invention.
Figure 11:
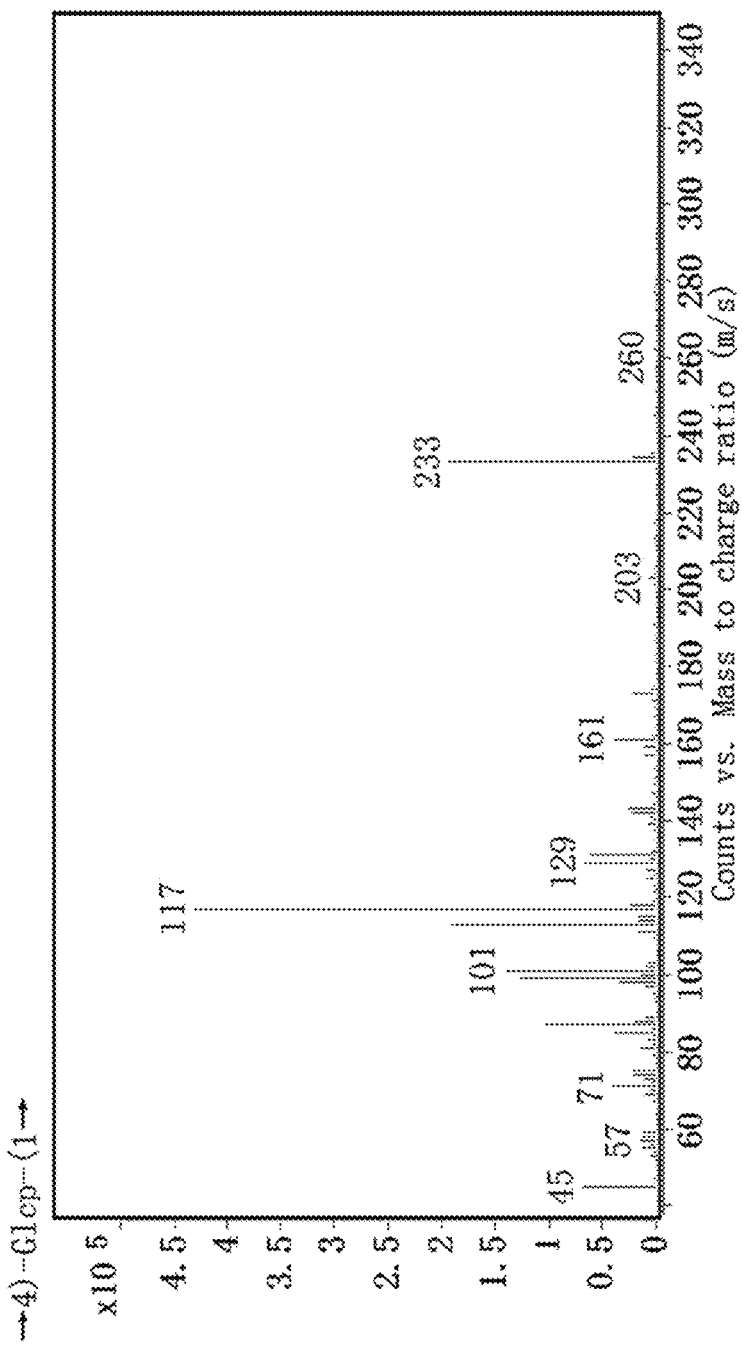
FIG. 11: Schematic diagram 3 of the mass-to-charge ratio analysis results of permethylated alditol acetate (PMAA) of polysaccharide, provided by an embodiment of the invention.
Figure 12:
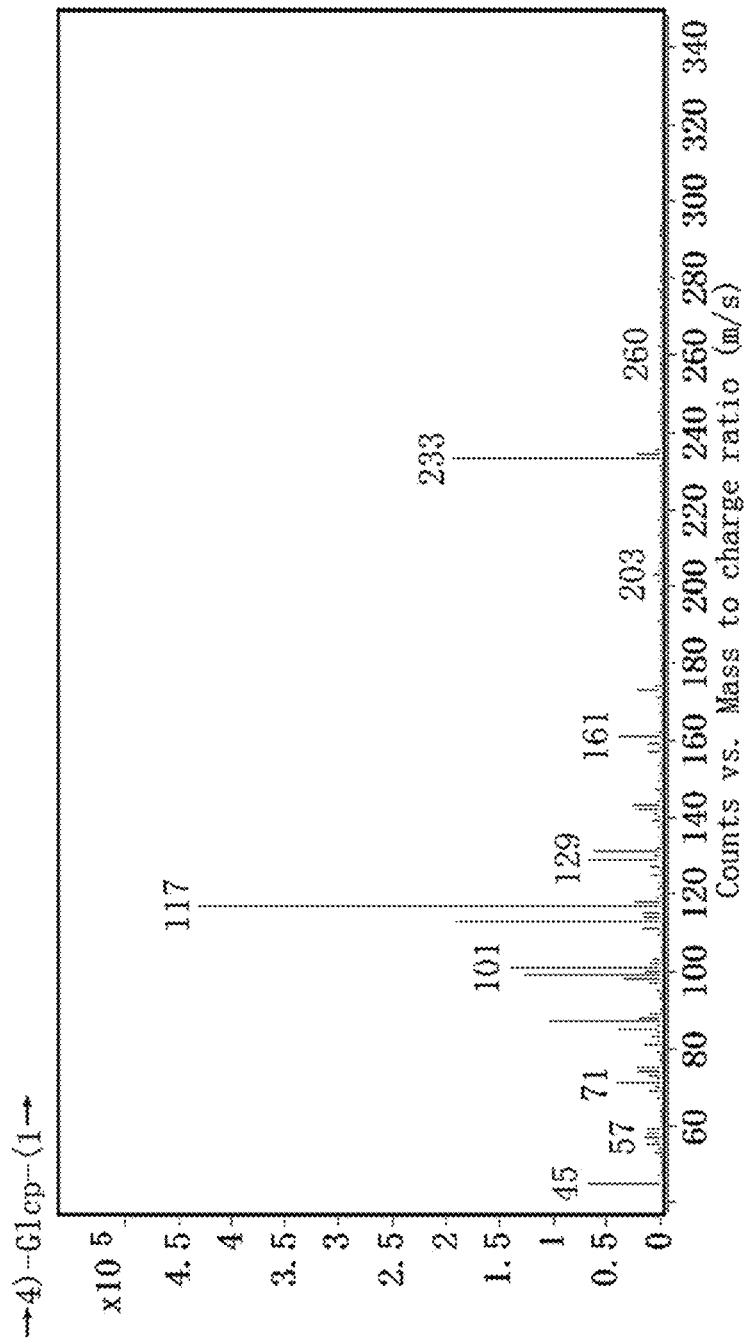
FIG. 12: Schematic diagram 4 of the mass-to-charge ratio analysis results of permethylated alditol acetate (PMAA) of polysaccharide, provided by an embodiment of the invention.
Figure 13:
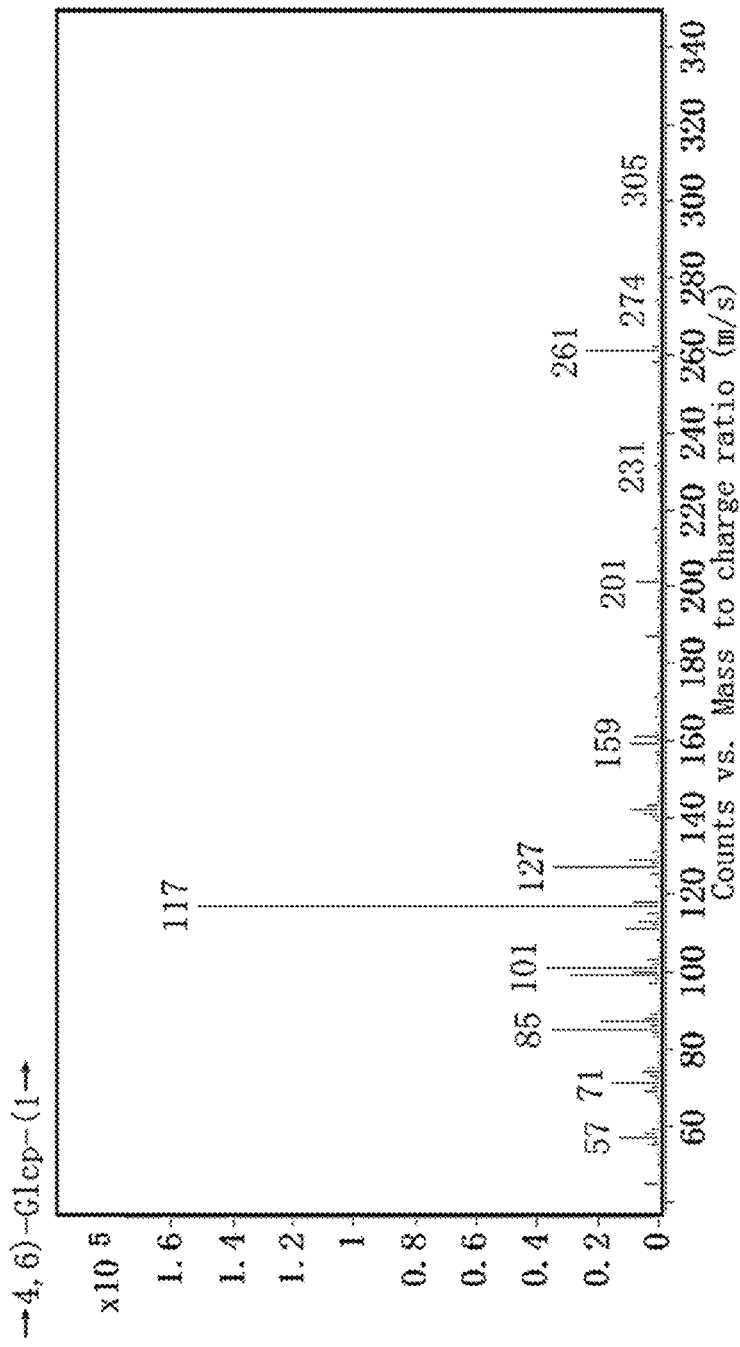
FIG. 13: Schematic diagram 5 of the mass-to-charge ratio analysis results of permethylated alditol acetate (PMAA) of polysaccharide, provided by an embodiment of the invention.

The GC-MS chromatogram of the sample (PMAA) is shown in FIG. 8.

The permethylated alditol acetate (PMAA) analysis of the polysaccharide is presented in the following table and FIGS. 9-13.

| RT | Methylated sugar | Mass fragments (m/z) | Molar ratio | Type of linkage |
|---|---|---|---|---|
| 17.412 | 2, 3, 4, 6-Me$_4$-Glcp | 45, 71, 87, 101, 117, 129, 145, 161, 205 | 0.261 | Glcp-(1→ |
| 21.343 | 2, 4, 6-Me$_2$-Glcp | 45, 71, 87, 101, 117, 129, 161, 189, 233 | 0.243 | →3)-Glcp-(1→ |
| 21.935 | 2, 3, 6-Me$_2$-Glcp | 45, 87, 99, 101, 113, 117, 129, 131, 161, 173, 233 | 0.171 | →4)-Glcp-(1→ |

-continued

| RT | Methylated sugar | Mass fragments (m/z) | Molar ratio | Type of linkage |
|---|---|---|---|---|
| 22.752 | 2, 3, 4-Me$_2$-Glcp | 45, 87, 99, 101, 117, 129, 161, 189, 233 | 0.167 | →6-Glcp-(1→ |
| 27.58 | 2, 3-Me2-Glcp | 45, 71, 85, 87, 99, 101, 117, 127, 159, 201 | 0.158 | →4, 6)-Glcp-(1→ |

IV. NMR SPECTRAL ANALYSIS AND INTERPRETATION

1. Experimental Materials and Equipment

Deuterium oxide (D2O, 99.9%) and deuterated acetone as internal standard; freeze-dryer, Bruker 600M Nuclear Magnetic Resonance (NMR) spectrometer;

2. Experimental Procedure 50 mg of the polysaccharide sample was weighed and dissolved in 0.5 mL of deuterium oxide followed by freeze-drying. The lyophilized powder was redissolved in 0.5 mL of deuterium oxide and freeze-drying was continued. The process was repeated to ensure complete exchange of labile hydrogens. Subsequently, the sample was dissolve in 0.5 mL of deuterium oxide, and 1H NMR, 13C NMR, DEPT135 one-dimensional and two-dimensional spectral measurements were performed at 25° C. using a 600 MHz NMR spectrometer.

3. Experimental Results

Figure 14:
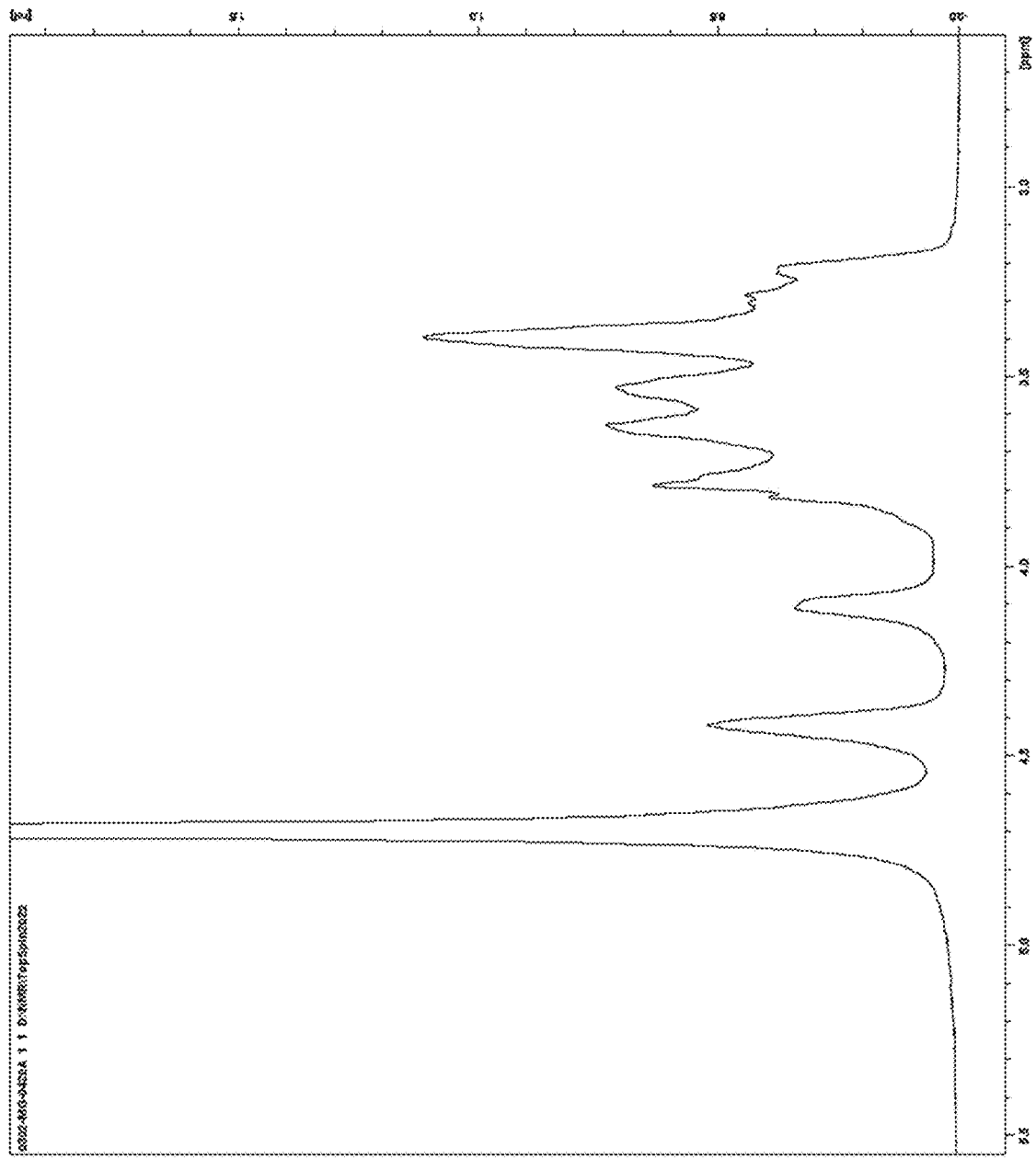
FIG. 14: Schematic diagram of the hydrogen spectrum provided by an embodiment of the invention.

The hydrogen spectrum signals were primarily concentrated between 3.0 and 5.5 ppm. The signals for sugar ring protons were between δ3.2-4.0 ppm, with main terminal group protons peaks at δ4.66, 4.64, 4.46, 4.43, and 4.41, primarily distributed in the 4.3-5.5 ppm region as shown in FIG. 14.

Figure 15:
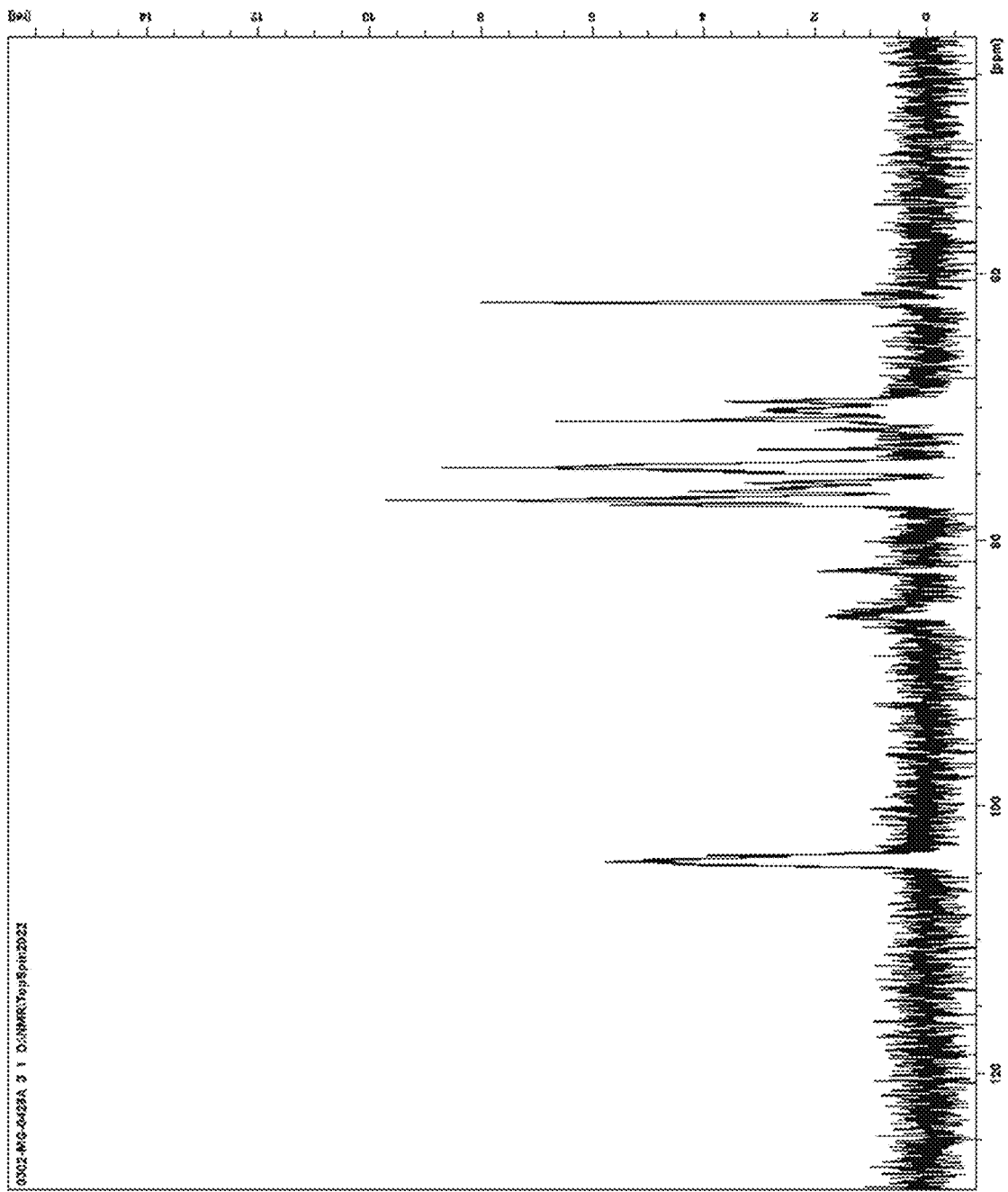
FIG. 15: Schematic diagram of the carbon spectrum provided by an embodiment of the invention.

Carbon spectral analysis in 13C NMR (201 MHz, D2O): The NMR carbon spectrum signals were mainly concentrated between 60-120 ppm. Observations of the carbon spectrum indicated main anomeric carbon signal peaks at δ103.92, 103.88, 103.82, 103.81, and 103.11, primarily between δ93-105. Other notable signal peaks were at δ74.51, 76.73, 70.88, 76.4, 70.48, 74.75, 85.63, 69.62, 77.02, 62.03, 74.15, 71.56, 80.14, 76.67, 61.66, 76.68, 74.08, 81.22, 75.39, 70.19, 72.71, 74.54, 69.22, 76.07, and 62.12 ppm. Based on monosaccharide composition results, the polysaccharide is composed of glucose, indicating the polysaccharide is primarily glucan. This is depicted in FIG. 15.

Figure 16:
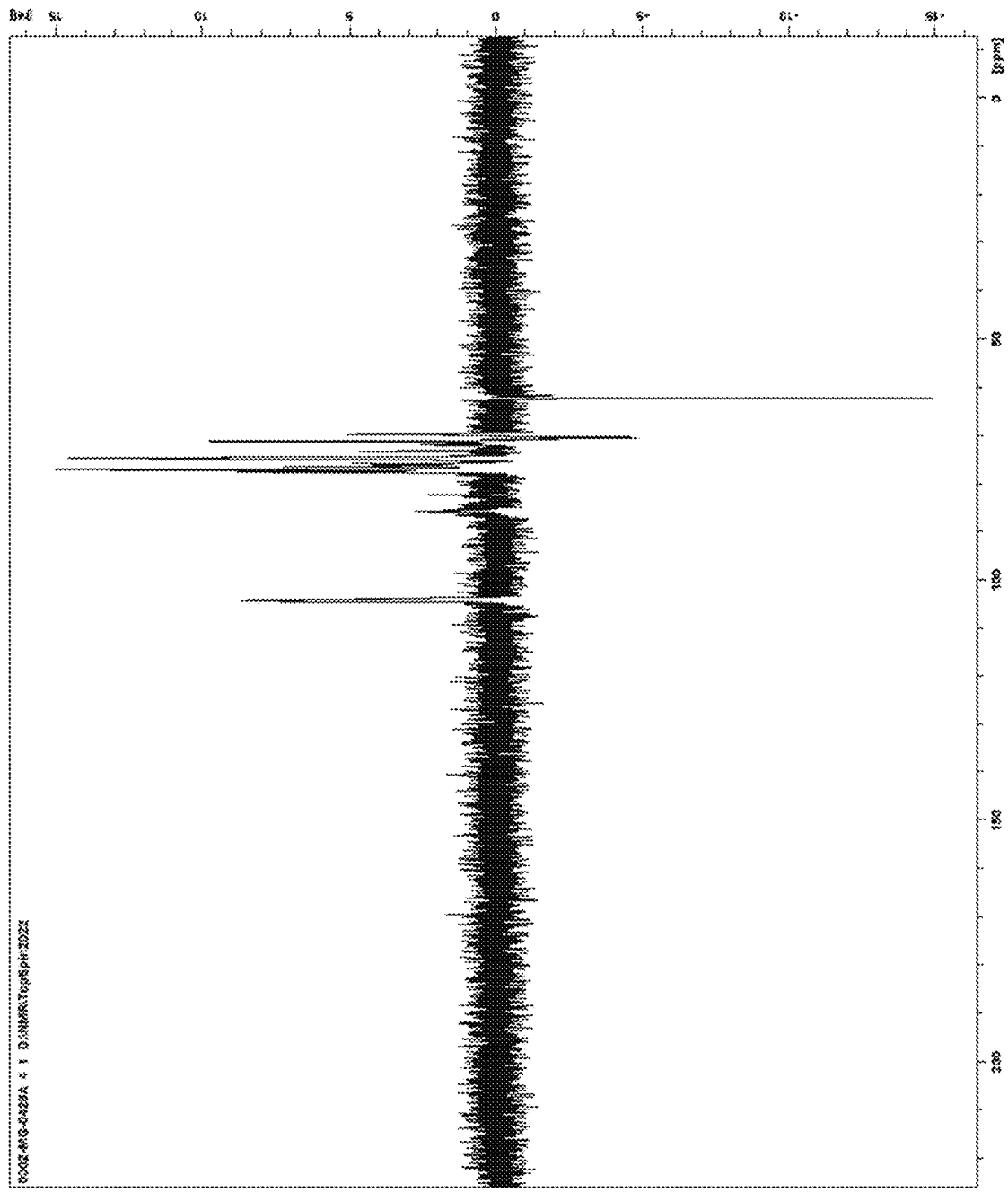
FIG. 16: Schematic diagram of the Dept135 spectrum provided by an embodiment of the invention.
Figure 17:
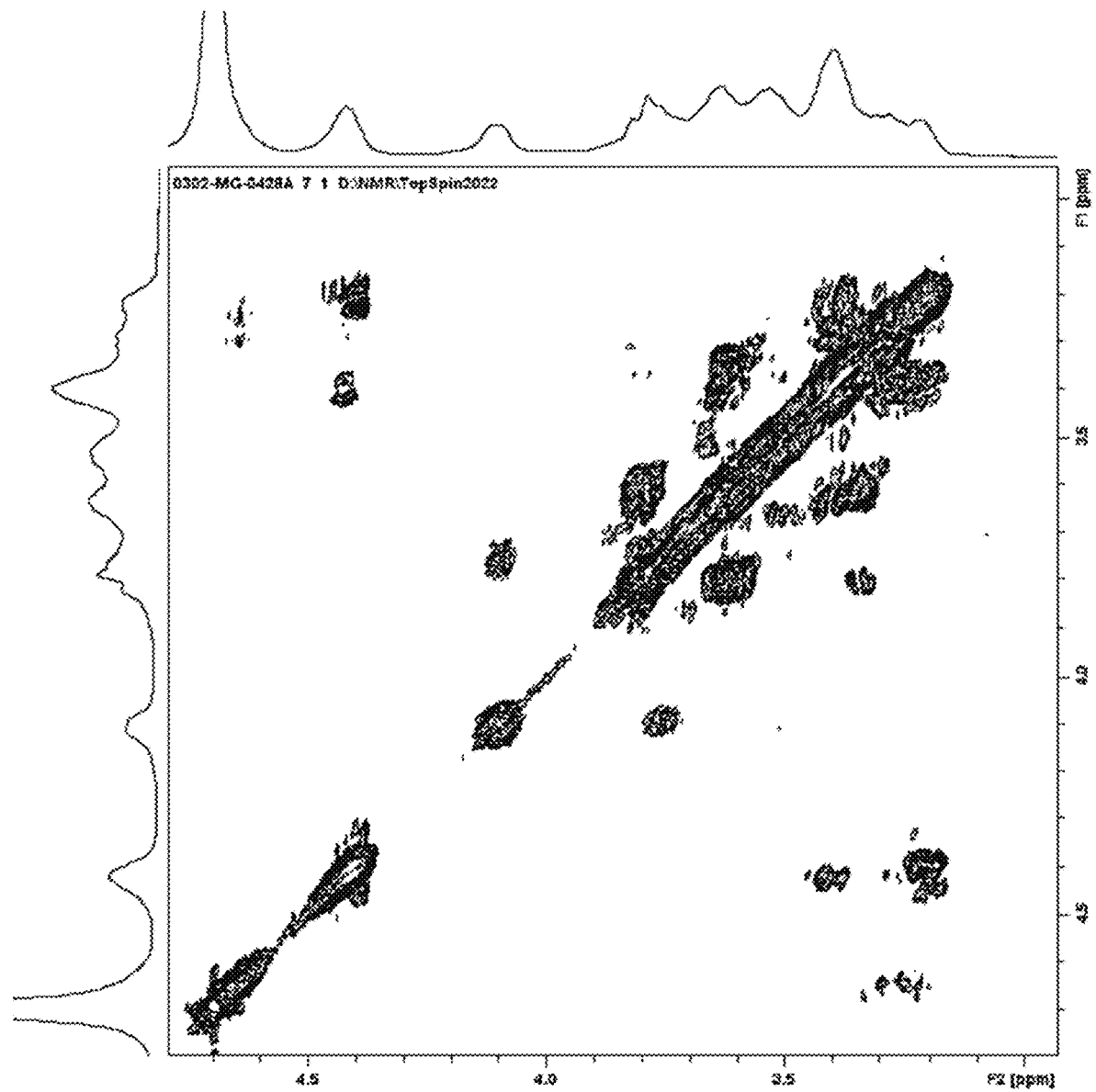
FIG. 17: Schematic diagram of HH-COSY provided by an embodiment of the invention.
Figure 18:
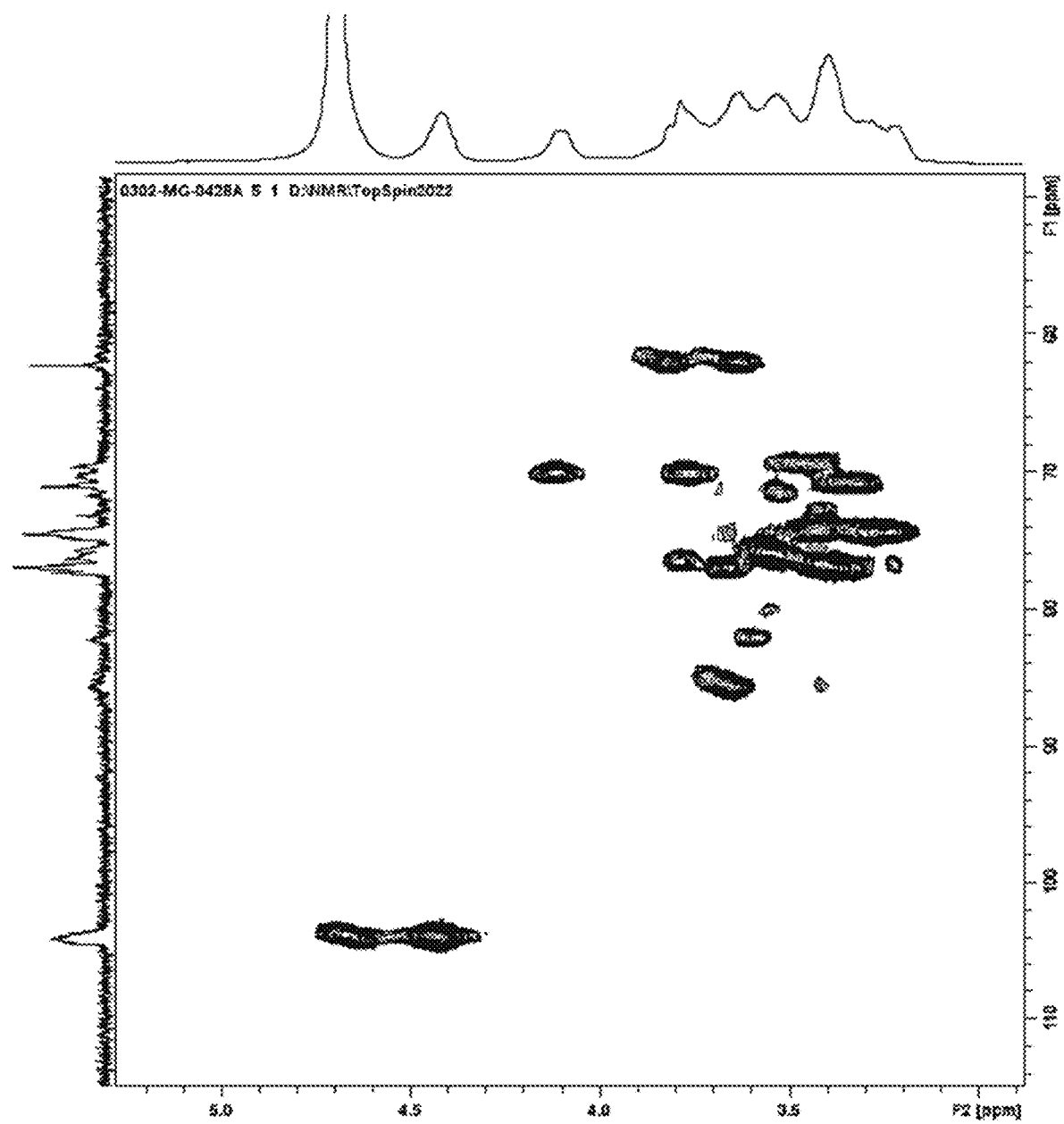
FIG. 18: Schematic diagram of HSQC provided by an embodiment of the invention.
Figure 19:
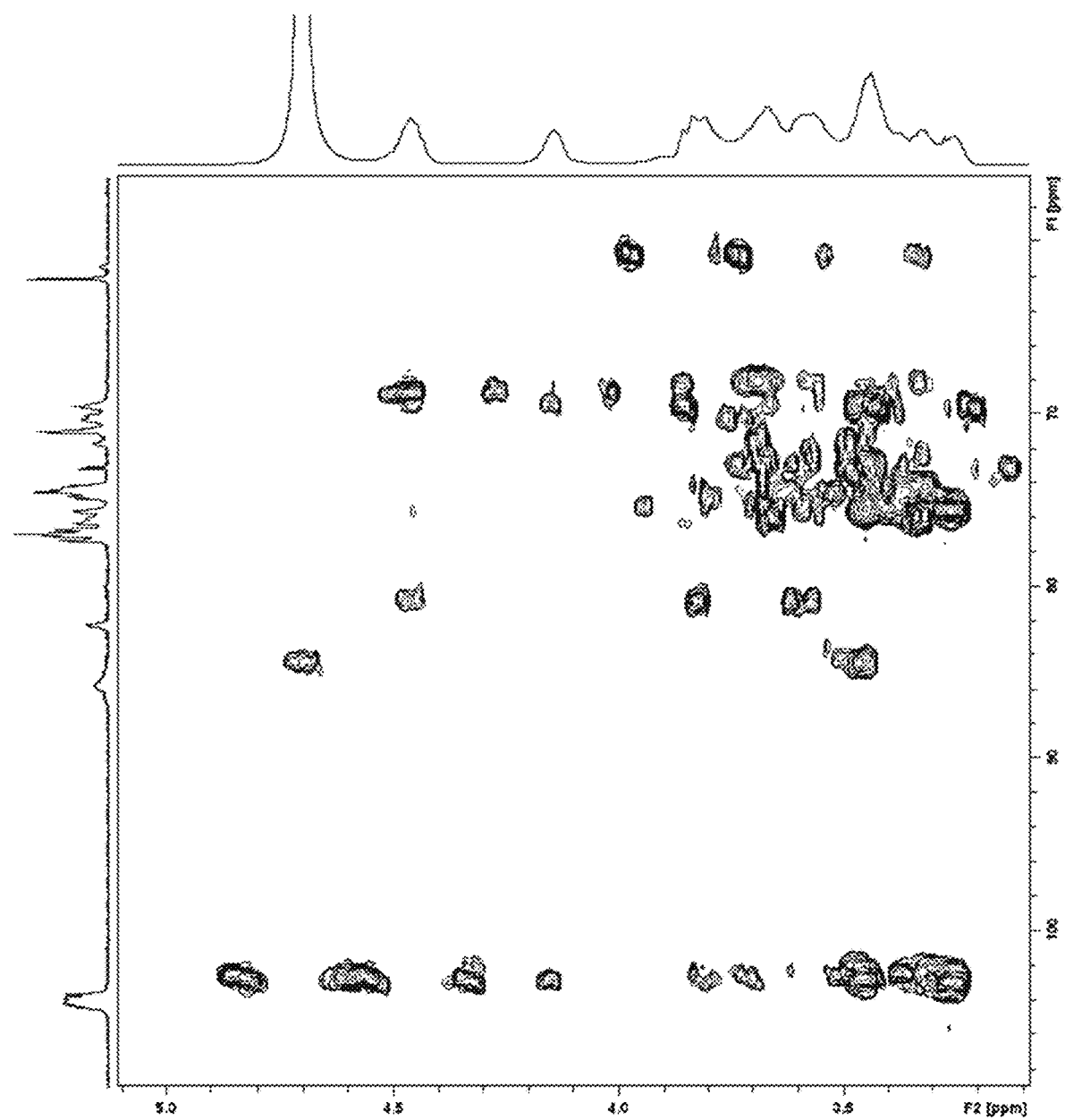
FIG. 19: HMBC spectrum provided by an embodiment of the invention.
Figure 20:
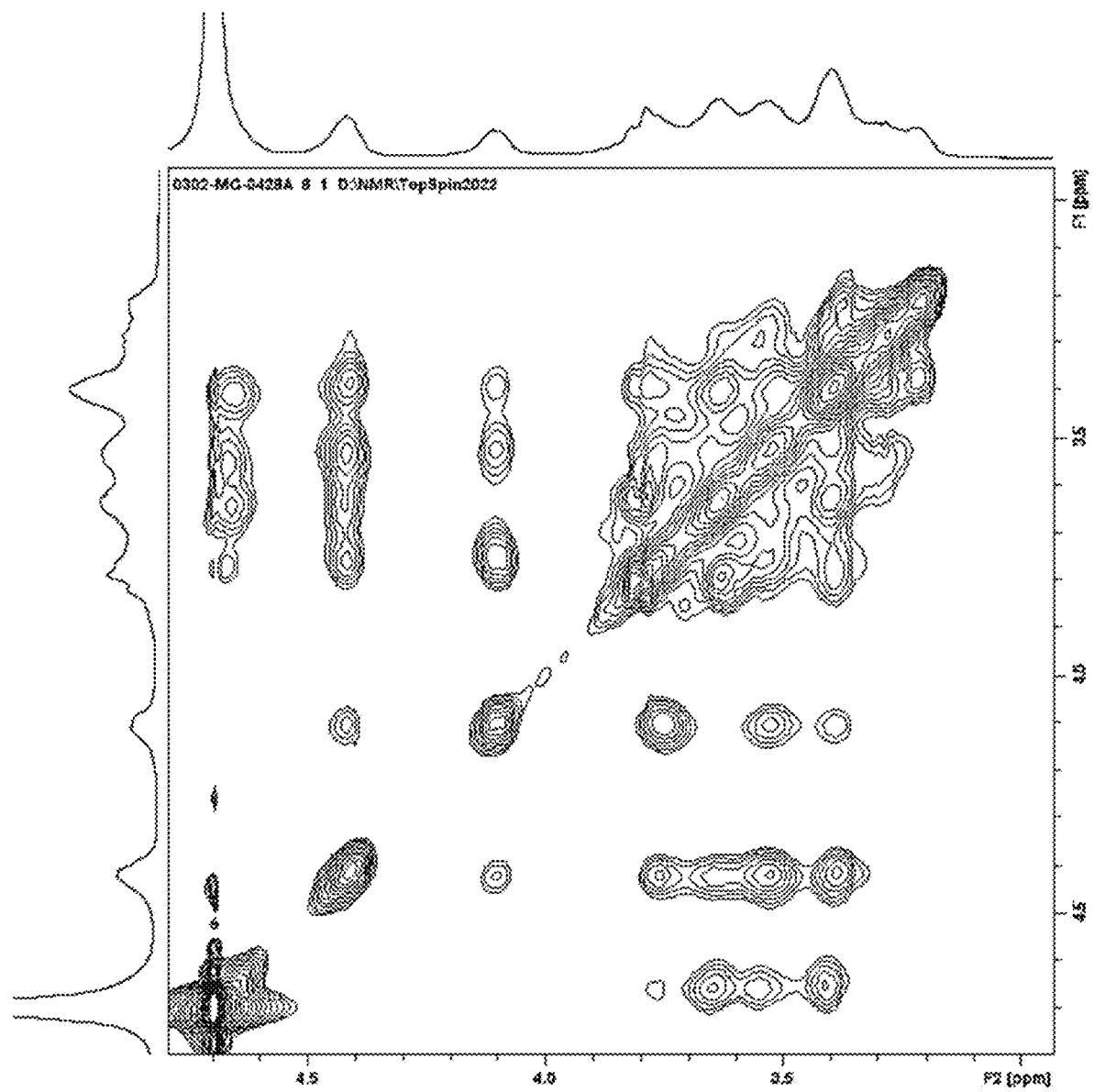
FIG. 20: Schematic diagram of NOESY provided by an embodiment of the invention.

Dept135 spectral analysis showed inverted peaks at 70.48, 70.19, 62.12, 62.03, and 61.66 ppm, indicative of chemical shifts for C6, as shown in FIG. 16.

FIGS. 17-20 present HSQC spectra where the anomeric carbon signal at δ103.11 corresponds to anomeric hydrogen signal at δ4.64. HH-COSY identifies H1-2 signal at 4.64/3.51; H2-3 signal at 3.51/3.67; H3-4 signal at 3.67/3.73. We deduce H1, H2, H3, and H4 as δ4.64, 3.51, 3.67, and 3.73 respectively, corresponding to δ103.11, 72.71, 74.54, and 69.22. Dept135 analysis confirmed C6 at 62.12 ppm, with H6b at 3.83 ppm and H6a at 3.63 ppm, correlating to C5 at 76.07; thus, these signals are attributed to the glycosidic bond β-Glcp-(1-→.

HSQC spectra show that the anomeric carbon signal at δ103.94 corresponds to anomeric hydrogen signal at δ4.66. HH-COSY identifies H1-2 signal at 4.66/3.47; H2-3 signal at 3.47/3.65. We deduce H1, H2, and H3 as δ4.66, 3.47, and 3.65 respectively, corresponding to δ103.88, 74.75, and 85.63.

HH-COSY identifies H6b-a signal at 3.81/3.62; H6a-5 signal at 3.62/3.39. The corresponding H6b, H6a, and H5 are at δ3.81, 3.62, and 3.39 respectively. The corresponding C5 is at 77.02; the chemical shift of C6 is at δ62.03. Therefore, this signal is attributed to the glycosidic bond →3)-β-Glcp-(1→.

Further HSQC observations show anomeric carbon signal at δ103.92, corresponding to anomeric hydrogen signal at δ4.41. HH-COSY identifies H1-2 signal at 4.41/3.22; H2-3 signal at 3.22/3.38; H3-4 signal at 3.38/3.54. We deduce H1, H2, H3, and H4 as δ4.41, 3.22, 3.38, 3.54 respectively, corresponding to C1-4 at δ103.92, 74.51, 76.73, and 70.88. NOESY spectra show correlated peaks at δ4.43 with 3.38, 3.54, 3.76, and 4.12. Dept135 combined with HSQC allows the attribution of δ3.76, 4.12 as peaks for H6a,b; H5 at 3.54 ppm. Corresponding C5 is at δ76.40; C6 chemical shift is at δ70.48, with H6a at δ3.76, 4.11. Therefore, this signal is attributed to the glycosidic bond →6)-β-Glcp-(1→.

Using similar patterns and combining HMBC and NOESY, all glycosidic bond signals are assigned as shown in the following table:

| Hydrogen and Carbon Signal Attribution | | | | | | | |
|---|---|---|---|---|---|---|---|
| Glycosyl residues | H1/C1 | H2/C2 | H3/C3 | H4/C4 | H5/C5 | H6a/C6 | H6b |
| β-D-Glcp-(1→ | 4.64 | 3.51 | 3.67 | 3.53 | 3.64 | 3.63 | 3.83 |
|  | 103.61 | 71.61 | 74.54 | 69.22 | 76.07 | 62.12 |  |
| →3)-β-D-Glcp-(1→ | 4.66 | 3.47 | 3.65 | 3.41 | 3.42 | 3.65 | 3.83 |
|  | 103.88 | 74.75 | 85.63 | 69.62 | 77.26 | 62.03 |  |
| →6)-β-D-Glcp-(1→ | 4.41 | 3.22 | 3.38 | 3.34 | 3.54 | 3.76 | 4.12 |
|  | 103.92 | 74.51 | 76.73 | 70.88 | 76.25 | 70.48 |  |
| →4,6)-β-D-Glcp-(1→ | 4.46 | 3.30 | 3.66 | 3.61 | 3.82 | 4.13 | 3.77 |
|  | 103.81 | 74.08 | 76.68 | 81.22 | 76.62 | 70.19 |  |
| →4)-β-D-Glcp-(1→ | 4.43 | 3.28 | 3.55 | 3.57 | 3.42 | 3.84 | 3.68 |
|  | 103.82 | 74.15 | 75.56 | 80.14 | 76.67 | 61.66 |  |

Main Chain Analysis

From the HMBC spectra, based on the one-dimensional and two-dimensional NMR spectra, we have attributed the signals of the glycosidic bonds in the polysaccharide: The anomeric hydrogen of the glycosidic bond →6)-β-D-Glcp-(1→shows correlation signal peaks with C6 of →4,6)-β-D-

Glcp-(1→, indicating the presence of a →6)-β-D-Glcp-(1→4,6)-β-DGlcp-(1→linkage.

Branch Chain Analysis

From the HMBC spectra, the anomeric hydrogen of the glycosidic bond β-D-Glcp-(1→shows correlation peaks with the H3 of →3)-β-D-Glcp-(1→, indicating the presence of a β-D-Glcp-(1→3)-β-D-Glcp-(1→linkage.

The anomeric hydrogen of the glycosidic bond →3)-β-D-Glcp-(1→shows correlation peaks with the H4 of →4)-β-D-Glcp-(1→, indicating the presence of a →3)-β-D-Glcp-(1→4)-β-D-Glcp-(1→linkage.

The anomeric hydrogen of the glycosidic bond →4)-β-D-Glcp-(1→shows correlation peaks with the H4 of →4,6)-β-D-Glcp-(1→, indicating the presence of a →4)-β-D-Glcp-(1→4,6)-β-D-Glcp-(1→linkage.

Based on the above, we can deduce that the main chain of the polysaccharide is the β-1,6 glucan, with β-D-Glcp-(1→3)-β-D-Glcp-(1→4)-β-D-Glcp-(1→linked to the main chain through an O- 4 bond of →4,6)-β-D-Glcp-(1→. The condensed structural formula is as follows.

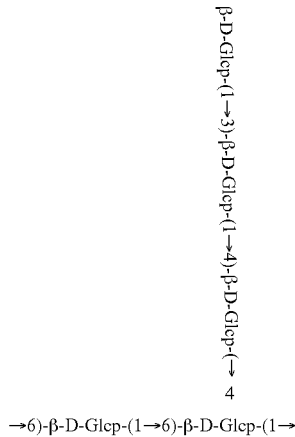

→6)-β-D-Glcp-(1→6)-β-D-Glcp-(1→

This invention also provides the application of the *Ganoderma lucidum* polysaccharide GLP-2. The *Ganoderma lucidum* polysaccharide GLP-2 is characterized by its water solubility, is readily absorbed by the human body, offers antitumor effects, and has proven efficacy in the prevention of tumor development in humans. Notably, when used in combination with cisplatin, a chemotherapy drug, it can alleviate toxic side effects caused by the chemotherapy drugs on the human body, control and reduce tumor masses, and reduce and eliminate cancer cells.

The *Ganoderma lucidum* polysaccharide GLP-2 is used in medications to inhibit tumor metastasis or to enhance human immune function.

Experimental Study on the Antitumor Effect of *Ganoderma lucidum* Polysaccharide GLP-2 Combined with Chemotherapy on LLC-Bearing Mice and Study Data Experimental Objective To study the antitumor effect of *Ganoderma lucidum* polysaccharide GLP-2 on lung cancer-bearing mice which are prepared by implanting LLC tumor homogenate in the right axilla of C57 mice. This study aims to provide experimental evidence for clinical studies of GLP-2.

Experimental Materials

Test Sample

*Ganoderma lucidum* polysaccharide GLP-2, provided by Shenzhen Aolimei Oncology Medical Technology Co., Ltd.

Positive Control

Cisplatin, batch number: E2128081, product of Shanghai Aladdin Biochemical Technology Co., Ltd.

Laboratory Animals

68 SPF male C57 mice, weighing 16-18 g, supplied by Guangdong Medical Laboratory Animal Center. Laboratory animal production license number: SCXK (Yue) 2022-0002; laboratory animal quality certification number: 44007200109382.

Main Reagents

PBS buffer, prepared by Shenzhen Aolimei Oncology Medical Technology Co., Ltd.; fetal bovine serum, product of Zhejiang Tianhang Biotechnology Co., Ltd.; DMEM culture medium, product of Gibco; 0.25% trypsin, product of Gibco.

Main Instruments

Vernier caliper, product of Shanghai Tool Works Co., Ltd.; I-2000 scale, Dongguan Nancheng Changxie Electronic Products Factory; ophthalmic scissors and tweezers, products of Shanghai Jinzhong Medical Instrument Co., Ltd.; CCL-170B-8 $CO_2$ incubator, product of ESCO, Singapore; Luna-II cell counter, product of Nanjing Hengqiao Instrument Co., Ltd.

Experimental Methods

Healthy LLC cells were inoculated subcutaneously into the left shoulder of 8 healthy male C57 mice. Once tumors reached a volume of 2,000-3,000 mm3, they were harvested and homogenized to prepare a homogenate suspension. This suspension was then injected subcutaneously into the axilla of 52 healthy male C57 mice to establish a solid tumor model. Once all mouse tumors averaged a volume of about 180 mm3, mice were randomized into groups based on tumor volume and were administered the respective drugs or drug solvents via oral gavage or intraperitoneal injection for 18 consecutive days. Longest and shortest diameters of tumors were measured every three days to calculate tumor volume, and mouse weights were recorded every three days. At the end of the experiment, tumors, spleens, and thymuses were harvested and weighed to calculate tumor, spleen, and thymus indices.

Dosage Design

Based on previous experimental results, *Ganoderma lucidum* polysaccharide GLP-2 was administered at a low dose of 50 mg/kg and a high dose of 150 mg/kg. The doses for each respective drug administered in this experiment are shown in Table 1.

Rationale for cisplatin dosage design: Based on the clinical dosage of cisplatin, which should not exceed 100 mg/m$^2$ per person per day, and considering the tolerance of mice to cisplatin, a dose of 4 mg/kg has been selected as the administration dosage.

TABLE 1

Experimental groups and dosage design

| Group | Dose (mg/kg) | Method of administration | Administration volume (mL/10 g) | Frequency of administration |
|---|---|---|---|---|
| Model control group | — | Oral gavage | 0.2 | Once daily |
| Cisplatin | 4 | Intraperitoneal injection | 0.2 | Once every 3 days |
| Cisplatin + GLP-2 low-dose group | 4 + 50 | Intraperitoneal injection + oral gavage | 0.2 + 0.2 | Cisplatin, once every 3 days; GLP-2, once daily |
| Cisplatin + GLP-2 high-dose group | 4 + 150 | Intraperitoneal injection + oral gavage | 0.2 + 0.2 | Cisplatin, once every 3 days; GLP-2, once daily |
| Normal group | — | Oral gavage | 0.2 | Once daily |

Test Indicators

Efficacy Indicators

Relative tumor growth inhibition rate

Relative tumor growth inhibition rate (%)=(1−TRTV/CRTV)×100%. Where TRTV is the relative tumor volume in the experimental group, and CRTV is the relative tumor volume in the model control group. Relative tumor volume (RTV)=Vt/V0, where Vt is the tumor volume on day t of dosing, and V0 is the tumor volume at the time of grouping. Evaluation criteria: A relative tumor growth inhibition rate of ≥40% and a statistical analysis with P<0.05 indicate effective inhibition.

Tumor growth inhibition rate

Tumor growth inhibition rate (%)=(1−T/C)×100%. Where T represents the average tumor weight in the treatment group, and C represents the average tumor weight in the model control group. Evaluation criteria: A tumor growth inhibition rate of ≥40% and a statistical analysis with P<0.05 indicate effective inhibition.

Spleen and thymus organ coefficients: After the last dose, spleen, thymus, and tumor weights are measured, and organ coefficients are calculated.

$$\text{Tumor index (\%)} = (\text{tumor weight/body weight}) \times 100\%.$$

$$\text{Immune organ index (mg/g)} = (\text{organ mass/body weight}) \times 1000.$$

Data Processing and Statistical Analysis

Statistical analyses were performed using SPSS 17.0, with the significance level set at P≤0.05. Measurement data were expressed as mean±standard deviation ($\bar{x}$±s). Normality and homogeneity of variance were tested using Leven's test. If data met normality and homogeneity of variance (P>0.05), one-way ANOVA and LSD test were used for statistical analysis. If data did not meet normality and homogeneity of variance (P<0.05), the Kruskal-Wallis test was used. If the Kruskal-Wallis test was statistically significant (P<0.05), comparison analysis was performed using Dunnett's Test (a non-parametric method). Evaluation considered statistical differences and biological significance.

Experimental Results

Animal Mortality

As shown in Table 2, the mortality rate was 25% in the cisplatin group and 0 in the remaining groups of mice.

TABLE 2

Statistics on the number of surviving animals and mortality rate in each group

| Group | Total number of animals | Number of deaths | Mortality rate (%) | Survival time (days) |
|---|---|---|---|---|
| Model control group | 8 | 0 | 0 | 18 ± 0 |
| Cisplatin | 8 | 2 | 25 | 17.1 ± 1.9 |
| Cisplatin + GLP-2 low-dose group | 8 | 0 | 0 | 18 ± 0 |
| Cisplatin + GLP-2 high-dose group | 8 | 0 | 0 | 18 ± 0 |
| Normal group | 8 | 0 | 0 | 18 ± 0 |

Effect of *Ganoderma lucidum* Polysaccharide GLP-2 Combined with Chemotherapy on Body Weight of LLC-Bearing Mice As shown in Table 3, compared to the normal group, the body weight of mice in the model control group significantly increased from D15 to D18, and the body weight of mice in the cisplatin group, the cisplatin+GLP-2 low-dose and high-dose groups significantly decreased from D6 to D18.

Compared to the model control group, the body weight of mice in the cisplatin group significantly decreased from D9 to D18, and the body weight of mice in the cisplatin+GLP-2 low-dose and high-dose groups significantly decreased from D6 to D18.

Compared to the cisplatin group, the body weight of mice in the cisplatin+GLP-2 low-dose group significantly decreased from D9 to D18, and the body weight of mice in the cisplatin+GLP-2 high-dose group significantly decreased on D18.

TABLE 3

Effect of *Ganoderma lucidum* polysaccharide GLP-2 combined with chemotherapy on body weight of LLC-bearing mice ($\bar{x} \pm s$)

| Group | Weight (g) | | | | | | |
|---|---|---|---|---|---|---|---|
| | D0 | D3 | D6 | D9 | D12 | D15 | D18 |
| Model control group | 20.8 ± 1.2 | 21.1 ± 1.7 | 21.3 ± 1.6 | 22.3 ± 1.6 | 23.5 ± 1.9 | 25.4± 2.1* | 26.2± 2.2* |
| Cisplatin | 20.8 ± 1.4 | 20.7 ± 1.3 | 20.4± 1* | 19.7± 0.8*+ | 18.5 ± 0.6*+ | 18.2± 1.2*+ | 17.9± 1.4*+ |
| Cisplatin + GLP-2 low-dose group | 20.9 ± 1 | 20.3 ± 0.6 | 19.4± 0.8*+ | 18.3± 0.8*+# | 16.6± 0.8*+# | 15.6± 0.7*+# | 14.7± 1*+# |
| Cisplatin + GLP-2 high-dose group | 20.9 ± 0.9 | 20.4 ± 1.1 | 20± 1.3*+ | 19.3± 1.8*+ | 18.5± 1.9*+ | 17.3± 1.7*+ | 16.3± 1.4*+# |
| Normal group | 20.7 ± 1.2 | 21.3 ± 1 | 21.6 ± 1.2 | 21.9 ± 1.3 | 22.5 ± 1.2 | 22.9 ± 1.3+ | 23 ± 1.6+ |

Note:
Compared to the model control group, +P < 0.05; Compared to the cisplatin group, #P < 0.05; Compared to the normal group, *P < 0.05.

Effect of *Ganoderma lucidum* Polysaccharide GLP-2 Combined with Chemotherapy on Tumor Volume in LLC-Bearing Mice As shown in Table 4, compared to the model control group, the tumor volume in the cisplatin group, the cisplatin+GLP-2 low-dose group, and the cisplatin+GLP-2 high-dose group was significantly reduced from D6 to D18.

Compared to the cisplatin group, the tumor volume in the cisplatin+GLP-2 low-dose group and cisplatin+GLP-2 high-dose group was significantly reduced from D15 to D18.

TABLE 4

Effect of *Ganoderma lucidum* polysaccharide GLP-2 combined with chemotherapy on tumor volume in LLC-bearing mice (x ± s)

| Group | Tumor volume (mm³) | | | | | | |
|---|---|---|---|---|---|---|---|
| | D0 | D3 | D6 | D9 | D12 | D15 | D18 |
| Model control group | 183.1 ± 35.1 | 411.7 ± 104.7 | 1108.6 ± 191.9 | 1462.8 ± 233.1 | 2538.4 ± 485.7 | 3969.5 ± 591 | 5493 ± 528 |
| Cisplatin | 193 ± 41.9 | 350.8 ± 138.5 | 692.4± 215.3+ | 956.4± 394+ | 1186.6± 386.4+ | 1388.9± 448.2+ | 1679.8± 439+ |
| Cisplatin + GLP-2 low-dose group | 195.4 ± 44.1 | 368.1 ± 141.7 | 566.8± 281.2+ | 735.2± 309.5+ | 799.3± 304+ | 831.9± 302.6+* | 860.4± 357.7+# |
| Cisplatin + GLP-2 high-dose group | 181.8 ± 33.8 | 345.4 ± 143.4 | 520.1± 171.9+ | 777.4± 480.6+ | 889± 509+ | 847.9± 391.1+* | 937.4± 261+# |

Note:
Compared to the model control group, +P < 0.05; Compared to the cisplatin group, #P < 0.05.

Effect of *Ganoderma lucidum* Polysaccharide GLP-2 Combined with Chemotherapy on Relative Tumor Growth Inhibition Rate in LLC-Bearing Mice As indicated in Table 5, compared to the model control group, the relative tumor growth inhibition rate in the cisplatin group from D6 to D18 was over 40%, specifically 41.7%, 40.1%, 56.2%, 68.0%, and 70.9%; the relative tumor growth inhibition rate in the cisplatin+GLP-2 low-dose group from D6 to D18 was over 50%, specifically 52.7%, 54.0%, 71.1%, 80.8%, and 85.5%; the relative tumor growth inhibition rate in the cisplatin+GLP-2 high-dose group from D6 to D18 was over 45%, specifically 53.7%, 48.7%, 66.2%, 79.3%, and 83.3%.

As shown in Table 6, compared to the cisplatin group, the relative tumor growth inhibition rate in the cisplatin+GLP-2 low-dose group from D15 to D18 was 39.9% and 50.3% (P<0.05), and the relative tumor growth inhibition rate in the cisplatin+GLP-2 high-dose group from D15 to D18 was 35.4% and 42.5% (P<0.05).

TABLE 5

Effect of *Ganoderma lucidum* polysaccharide GLP-2 combined with chemotherapy on relative tumor growth inhibition rate in LLC-bearing mice (vs. the model control group)

| Group | Relative tumor growth inhibition rate (compared to model control group) (%) | | | | | |
|---|---|---|---|---|---|---|
| | D3 | D6 | D9 | D12 | D15 | D18 |
| Model control group | — | — | — | — | — | — |
| Cisplatin | 21.2 | 41.7+ | 40.1+ | 56.2+ | 68.0+ | 70.9+ |
| Cisplatin + GLP-2 low-dose group | 17.8 | 52.7+ | 54.0+ | 71.1+ | 80.8+ | 85.5+ |
| Cisplatin + GLP-2 high-dose group | 17.8 | 53.7+ | 48.7+ | 66.2+ | 79.3+ | 83.3+ |

Note:
Compared to the model control group, +P < 0.05

TABLE 6

Effect of *Ganoderma lucidum* polysaccharide GLP-2 combined with chemotherapy on relative tumor growth inhibition rate in LLC-bearing mice (vs. the cisplatin group)

| Group | Relative tumor growth inhibition rate (compared to cisplatin group) (%) | | | | | |
|---|---|---|---|---|---|---|
| | D3 | D6 | D9 | D12 | D15 | D18 |
| Cisplatin | — | — | — | — | — | — |
| Cisplatin + GLP-2 low-dose group | −4.4 | 18.9 | 23.1 | 34.0 | 39.9# | 50.3# |
| Cisplatin + GLP-2 high-dose group | −4.4 | 20.6 | 14.3 | 22.8 | 35.4# | 42.5# |

Note:
Compared to the cisplatin group, #$P < 0.05$.

Effect of *Ganoderma lucidum* Polysaccharide GLP-2 Combined with Chemotherapy on Organ Coefficients and Tumor Growth Inhibition Rates in LLC-Bearing Mice As indicated in Table 7, compared to the model group, the tumor index, spleen index, and thymus index were significantly reduced in the cisplatin group, the cisplatin+GLP-2 low-dose group, and the cisplatin+GLP-2 high-dose group. Compared to the cisplatin group, the tumor index and spleen index were significantly reduced in the cisplatin+GLP-2 low-dose group and the cisplatin+GLP-2 high-dose group. Compared to the normal group, the spleen index was significantly higher in the model control group, but significantly reduced in the cisplatin+GLP-2 low-dose group; the thymus index was significantly reduced in the model control group, cisplatin group, cisplatin+GLP-2 low-dose group, and cisplatin+GLP-2 high-dose group.

Compared to the model control group, the tumor growth inhibition rate was 67.3% in the cisplatin group, and 83.6% and 81.2% in the cisplatin+GLP-2 low-dose and high-dose groups, respectively. Compared to the cisplatin group, the tumor growth inhibition rate was 49.7% and 42.4% in the cisplatin+GLP-2 low-dose and high-dose groups, respectively.

TABLE 7

Effect of *Ganoderma lucidum* polysaccharide GLP-2 combined with chemotherapy on organ indices and tumor growth inhibition rates in LLC-bearing mice

| Group | Tumor index (%) | Spleen index (mg/g) | Thymus index (mg/g) | Tumor growth inhibition rate (%) vs. the model control group | Tumor growth inhibition rate (%) vs. the cisplatin group |
|---|---|---|---|---|---|
| Model control group | 24.7 ± 4 | 11.4 ± 2.2* | 1.1 ± 0.4* | — | — |
| Cisplatin | 11.8 ± 3.6+ | 4.1 ± 1.2+ | 0.4 ± 0.1*+ | 67.3 | — |
| Cisplatin + GLP-2 low-dose group | 7 ± 3.6+# | 2.1 ± 0.3*+# | 0.4 ± 0.1*+ | 83.6 | 49.7 |
| Cisplatin + GLP-2 high-dose group | 7.3 ± 2.8+# | 2.6 ± 0.5+# | 0.4 ± 0.1*+ | 81.2 | 42.4 |
| Normal group | — | 3.1 ± 0.3+ | 1.7 ± 0.2+ | — | — |

Note:
Compared to the model control group, +$P < 0.05$; Compared to the cisplatin group, #$P < 0.05$; Compared to the normal group, *$P < 0.05$.

Figure 21:
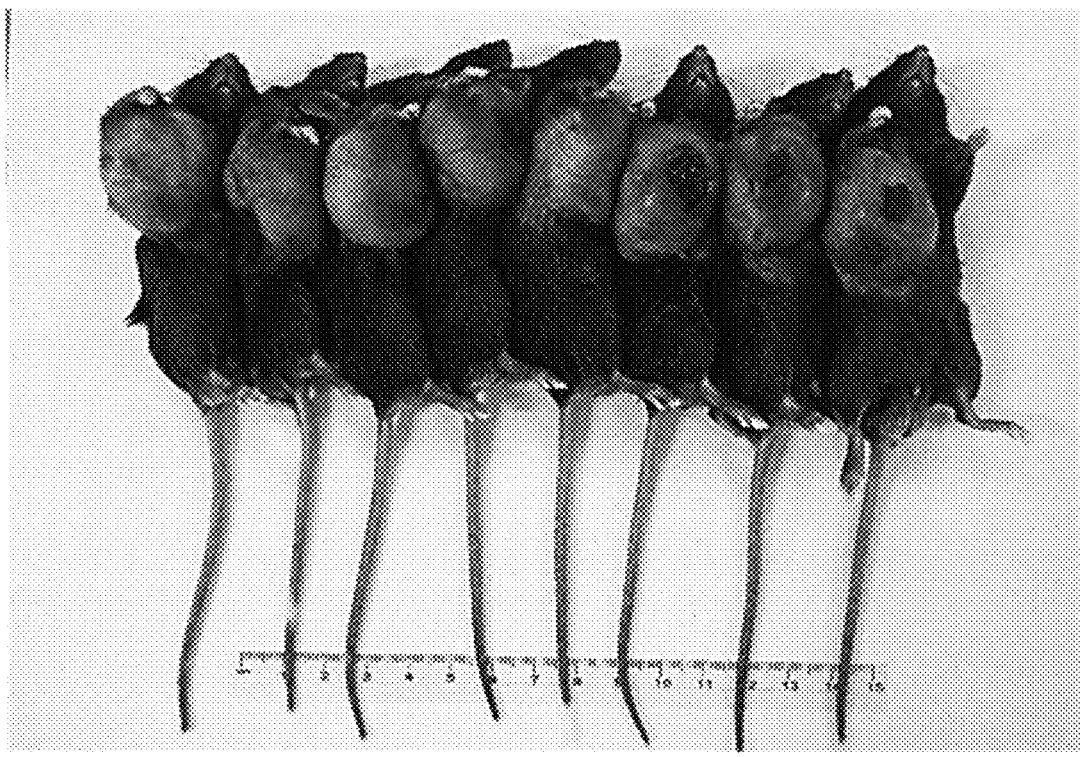
FIG. 21: Schematic diagram of the control group of LLC-bearing mouse model treated with *Ganoderma lucidum* polysaccharide GLP-2 combined with chemotherapy, provided by an embodiment of the invention.
Figure 22:
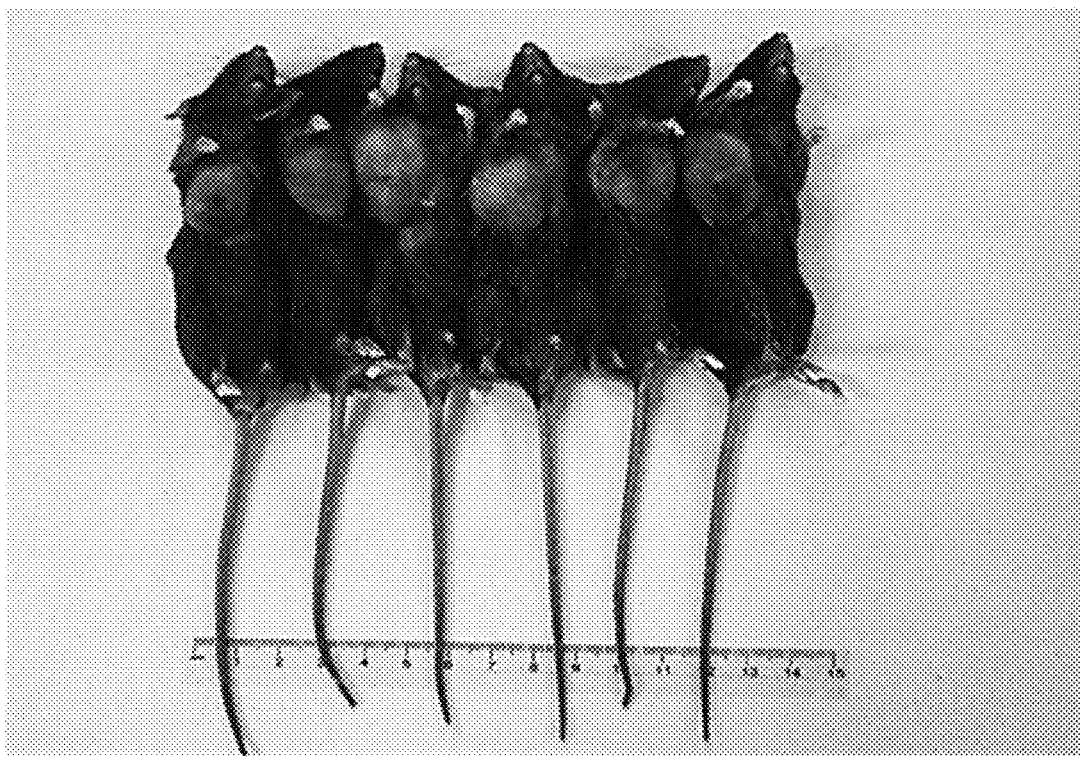
FIG. 22: Schematic diagram of the cisplatin group of LLC-bearing mice treated with *Ganoderma lucidum* polysaccharide GLP-2 combined with chemotherapy, provided by an embodiment of the invention.
Figure 23:
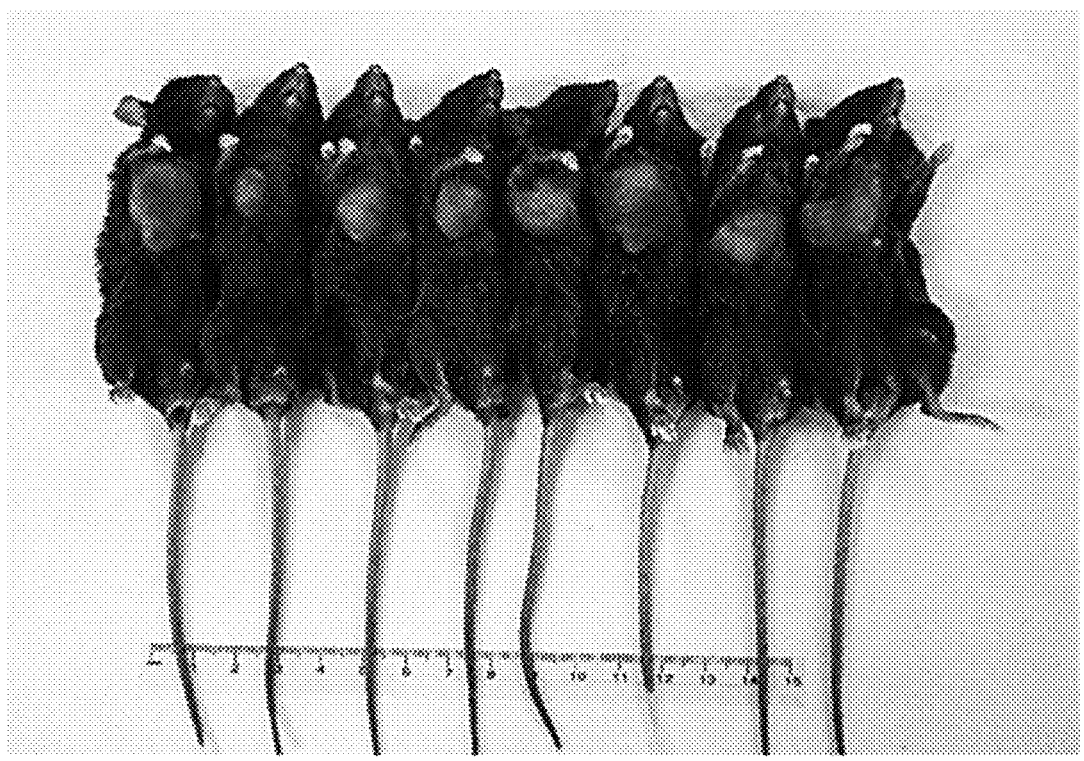
FIG. 23: Schematic diagram of the cisplatin+low-dose GLP-2 group of LLC-bearing mice treated with *Ganoderma lucidum* polysaccharide GLP-2 combined with chemotherapy, provided by an embodiment of the invention.
Figure 24:
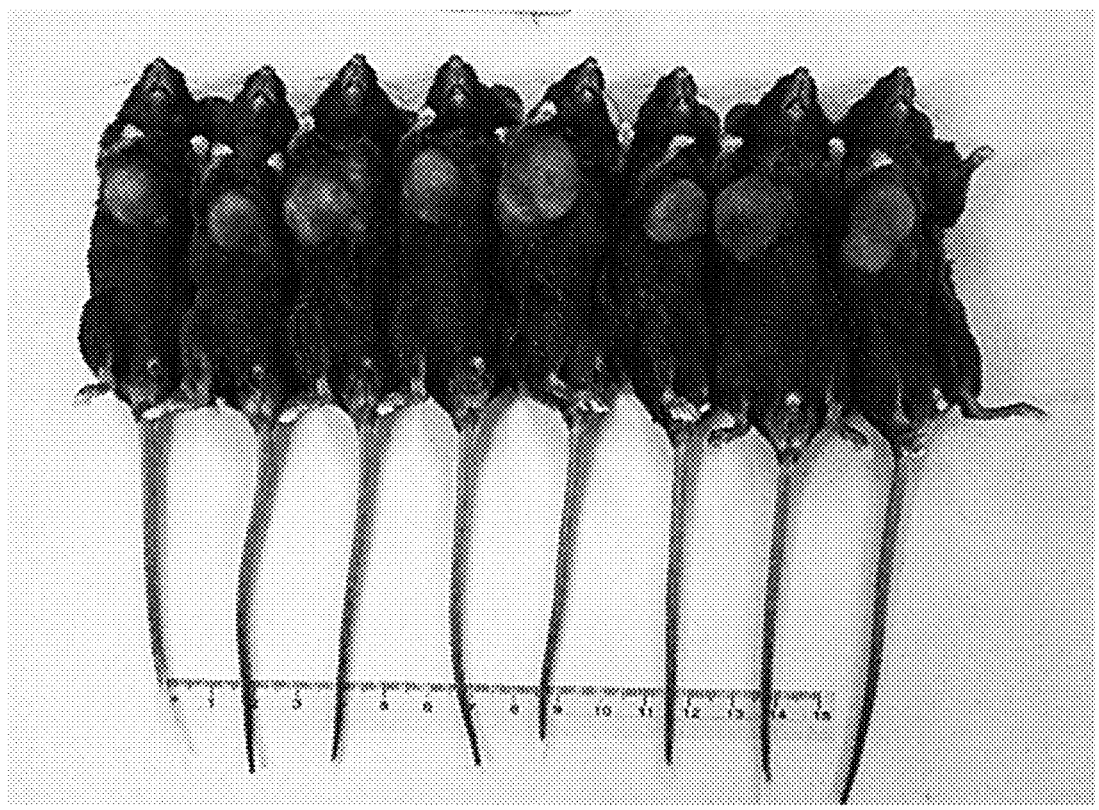
FIG. 24: Schematic diagram of the cisplatin+high-dose GLP-2 group of LLC-bearing mice treated with *Ganoderma lucidum* polysaccharide GLP-2 combined with chemotherapy, provided by an embodiment of the invention.

FIGS. 21-24 show images of the tumor-bearing mice, corresponding to the groups as follows: FIG. 21: model control group, FIG. 22: cisplatin group, FIG. 23: cisplatin+GLP-2 low-dose group, FIG. 24: cisplatin+GLP-2 high-dose group.

Figure 25:
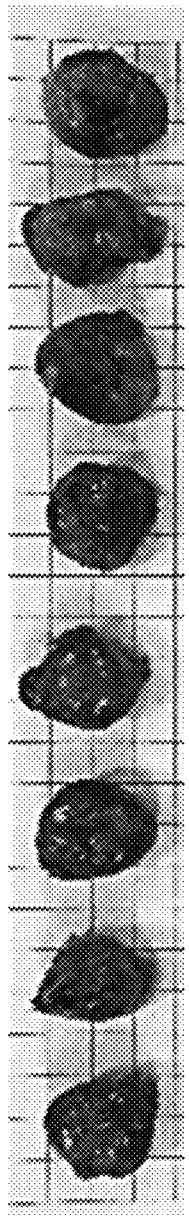
FIG. 25: Schematic diagram of tumor models in the control group of LLC-bearing mice treated with *Ganoderma lucidum* polysaccharide GLP-2 combined with chemotherapy, provided by an embodiment of the invention.
Figure 26:
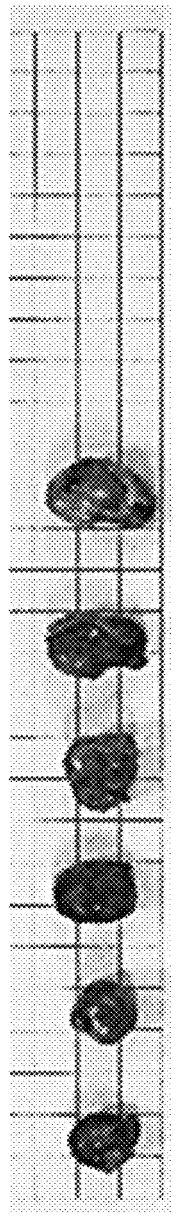
FIG. 26: Schematic diagram of tumors in the cisplatin group of LLC-bearing mice treated with *Ganoderma lucidum* polysaccharide GLP-2 combined with chemotherapy, provided by an embodiment of the invention.
Figure 27:
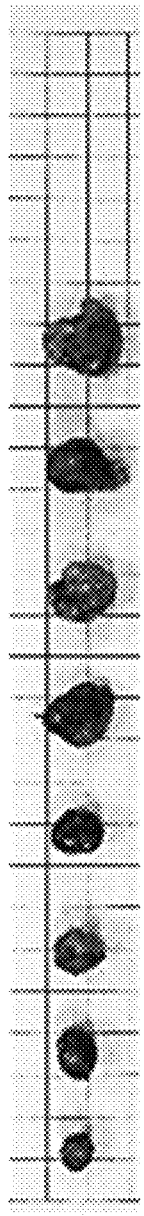
FIG. 27: Schematic diagram of tumors in the cisplatin+low-dose GLP-2 group of LLC-bearing mice treated with *Ganoderma lucidum* polysaccharide GLP-2 combined with chemotherapy, provided by an embodiment of the invention.
Figure 28:
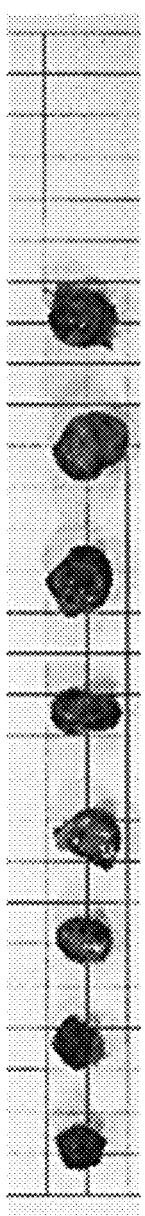
FIG. 28: Schematic diagram of tumors in the cisplatin+high-dose GLP-2 group of LLC-bearing mice treated with *Ganoderma lucidum* polysaccharide GLP-2 combined with chemotherapy, provided by an embodiment of the invention.

FIGS. 25-28 show images of the tumors in the tumor-bearing mice, corresponding to the groups as follows: FIG. 25: model control group, FIG. 26: cisplatin group, FIG. 27: cisplatin+GLP-2 low-dose group, FIG. 28: cisplatin+GLP-2 high-dose group.

Conclusion

*Ganoderma lucidum* Polysaccharide GLP-2 combined with cisplatin significantly inhibits tumor growth in LLC-bearing mice and exhibits a significant synergistic effect.

Experimental Study on the Antitumor Effect of *Ganoderma lucidum* Polysaccharide GLP-2 Combined with Chemotherapy on H22-Bearing Mice and Study Data

Experimental Objective

To study the antitumor effect of *Ganoderma lucidum* polysaccharide GLP-2 on hepatoma-bearing mice which are prepared by implanting H22 hepatoma tumor homogenate in the right axilla of C57 mice. This study aims to provide experimental evidence for clinical studies of GLP-2.

Experimental Materials

Test Sample

*Ganoderma lucidum* polysaccharide GLP-2, provided by Shenzhen Aolimei Oncology Medical Technology Co., Ltd.

Positive Control

Cisplatin, batch number: E21268081, product of Shanghai Aladdin Biochemical Technology Co., Ltd.

Laboratory Animals

55 SPF male C57 mice, weighing 16-18 g, supplied by Guangdong Medical Laboratory Animal Center. Laboratory animal production license number: SCXK (Yue) 2022-0002; laboratory animal quality certification number: 44007200104725.

Main Reagents

PBS buffer, prepared by Shenzhen Aolimei Oncology Medical Technology Co., Ltd.; fetal bovine serum, product of Zhejiang Tianhang Biotechnology Co., Ltd.; 1640 culture medium, product of Gibco; 0.25% trypsin, product of Gibco.

Main Instruments

Vernier caliper, product of Shanghai Tool Works Co., Ltd.; I-2000 scale, Dongguan Nancheng Changxie Electronic Products Factory; ophthalmic scissors and tweezers, products of Shanghai Jinzhong Medical Instrument Co., Ltd.; CCL-170B-8 CO2 incubator, product of ESCO, Singapore; Luna-II cell counter, product of Nanjing Hengqiao Instrument Co., Ltd.

Experimental Methods

A homogenate suspension of H22 mouse hepatoma was injected subcutaneously under the axilla of 45 healthy male C57 mice to create a solid tumor model. Once all mouse tumors averaged a volume of about 150 mm3, mice were randomized into groups based on tumor volume and were administered the respective drugs or drug solvents via oral gavage or intraperitoneal injection for 18 consecutive days. Longest and shortest diameters of tumors were measured every three days to calculate tumor volume, and mouse weights were recorded every three days. At the end of the experiment, tumors, spleens, and thymuses were harvested and weighed to calculate tumor, spleen, and thymus indices.

Dosage Design

Based on previous experimental results, *Ganoderma lucidum* polysaccharide GLP-2 was administered at a low dose of 50 mg/kg and a high dose of 150 mg/kg as shown in Table 8.

Rationale for cisplatin dosage design: Based on the clinical dosage of cisplatin, which should not exceed 100 mg/m$^2$ per person per day, and considering the tolerance of mice to cisplatin, a dose of 3 mg/kg has been selected as the administration dosage.

TABLE 8

Experimental groups and dosage design

| Group | Dose (mg/kg) | Method of administration | Administration volume (mL/10 g) | Frequency of administration |
|---|---|---|---|---|
| Model control group | — | Oral gavage | 0.2 | Once daily |
| Cisplatin | 3 | Intraperitoneal injection | 0.2 | Once every 3 days |
| Cisplatin + GLP-2 low-dose group | 3 + 50 | Intraperitoneal injection + oral gavage | 0.2 + 0.2 | Cisplatin, once every 3 days; GLP-2, once daily |
| Cisplatin + GLP-3 high-dose group | 3 + 150 | Intraperitoneal injection + oral gavage | 0.2 + 0.2 | Cisplatin, once every 3 days; GLP-2, once daily |
| Normal group | — | Oral gavage | 0.2 | Once daily |

Test Indicators

Efficacy Indicators

Relative Tumor Growth Inhibition Rate

Relative tumor growth inhibition rate $(\%) = (1 - T_{RTV}/C_{RTV}) \times 100\%$. Where $T_{RTV}$ is the relative tumor volume in the experimental group, and $C_{RTV}$ is the relative tumor volume in the model control group. Relative tumor volume $(RTV) = V_t/V_0$, where $V_t$ is the tumor volume on day t of dosing, and $V_0$ is the tumor volume at the time of grouping. Evaluation criteria: A relative tumor growth inhibition rate of ≥40% and a statistical analysis with P<0.05 indicate effective inhibition.

Tumor Growth Inhibition Rate

Tumor growth inhibition rate $(\%) = (1 - T/C) \times 100\%$. Where T represents the average tumor weight in the treatment group, and C represents the average tumor weight in the model control group. Evaluation criteria: A tumor growth inhibition rate of ≥40% and a statistical analysis with P<0.05 indicate effective inhibition.

Spleen and thymus organ coefficients: After the last dose, spleen, thymus, and tumor weights are measured, and organ coefficients are calculated.

$$\text{Tumor index } (\%) = (\text{tumor weight/body weight}) \times 100\%.$$

$$\text{Immune organ index } (mg/g) = (\text{organ mass/body weight}) \times 1000.$$

Data Processing and Statistical Analysis

Statistical analyses were performed using SPSS 17.0, with the significance level set at P≤0.05. Measurement data were expressed as mean±standard deviation ($\bar{x}\pm s$). Normality and homogeneity of variance were tested using Leven's test. If data met normality and homogeneity of variance (P>0.05), one-way ANOVA and LSD test were used for statistical analysis. If data did not meet normality and homogeneity of variance (P<0.05), the Kruskal-Wallis test was used. If the Kruskal-Wallis test was statistically significant (P<0.05), comparison analysis was performed using Dunnett's Test (a non-parametric method). Evaluation considered statistical differences and biological significance.

Experimental Results

Animal Mortality

As shown in Table 9, the mortality rate for all groups of mice was 0.

TABLE 9

Statistics on the number of surviving animals and mortality rate in each group

| Group | Total number of animals | Number of deaths | Mortality rate (%) | Survival time (days) |
|---|---|---|---|---|
| Model control group | 8 | 0 | 0.0 | 18 ± 0 |
| Cisplatin | 8 | 0 | 0.0 | 18 ± 0 |
| Cisplatin + GLP-2 low-dose group | 8 | 0 | 0.0 | 18 ± 0 |
| Cisplatin + GLP-2 high-dose group | 8 | 0 | 0.0 | 18 ± 0 |
| Normal group | 8 | 0 | 0 | 18 ± 0 |

Effect of *Ganoderma lucidum* Polysaccharide GLP-2 Combined with Chemotherapy on Body Weight of H22-Bearing Mice As indicated in Table 10, compared to the normal group, the body weight of mice in the model control group significantly increased on D18; the body weight of mice in the cisplatin group significantly increased from D12 to D18; the body weight of mice in the cisplatin+GLP-2 low-dose group significantly decreased from D6 to D18; and the body weight of mice in the cisplatin+GLP-2 high-dose group significantly decreased from D12 to D18.

Compared to the model control group, the body weight of mice in the cisplatin group significantly decreased from D12 to D18, the body weight of mice in the cisplatin+GLP-2 low-dose group significantly decreased from D6 to D18, and the body weight of mice in the cisplatin+GLP-2 high-dose group significantly decreased from D9 to D18.

Compared to the cisplatin group, the body weight of mice in the cisplatin+GLP-2 low-dose group significantly decreased on D6, D9, D12, and D18.

TABLE 10

Effect of *Ganoderma lucidum* polysaccharide GLP-2 combined with chemotherapy on body weight of H22-bearing mice ($\bar{x} \pm s$)

| Group | Weight (g) | | | | | | |
|---|---|---|---|---|---|---|---|
| | D0 | D3 | D6 | D9 | D12 | D15 | D18 |
| Model control group | 19.7 ± 0.8 | 20.4 ± 1.5 | 21.1 ± 1.6 | 22.1 ± 1.8 | 23.3 ± 2.1 | 23.3 ± 2.4 | 25.9± 2.6* |
| Cisplatin | 20.6 ± 1.3 | 20.8 ± 1.3 | 21 ± 1.3 | 21 ± 1.5 | 20.7± 1.4$^{+*}$ | 20.5± 1.4$^{+*}$ | 19.9± 1.7$^{+*}$ |
| Cisplatin + GLP-2 low-dose group | 19.5 ± 1.9 | 19.7 ± 1.4 | 19± 1.6$^{+\#*}$ | 18.7± 1.7$^{+\#*}$ | 18.6± 1.6$^{+\#*}$ | 18.7± 1.5$^{+*}$ | 17.7± 1.2$^{+\#*}$ |
| Cisplatin + GLP-2 high-dose group | 20.7 ± 1.1 | 20.6 ± 1.3 | 20.2 ± 1.6 | 20.2± 1.5$^{+*}$ | 20.3± 1.9$^{+*}$ | 20± 1.9$^{+*}$ | 19.6± 1.8$^{+*}$ |
| Normal group | 20.2 ± 0.6 | 21 ± 0.9 | 21.1 ± 1 | 21.7 ± 1 | 22.4 ± 1 | 22.9 ± 1.1 | 23.4 ± 1.1 |

Note:
Compared to the model control group, $^+P < 0.05$; Compared to the cisplatin group, $^\#P < 0.05$; Compared to the normal group, $*P < 0.05$.

Effect of *Ganoderma lucidum* Polysaccharide GLP-2 Combined with Chemotherapy on Tumor Volume in H22-Bearing Mice As shown in Table 11, compared to the model control group, the tumor volume in the cisplatin group was significantly reduced from D12 to D18, and the tumor volume in the cisplatin+GLP-2 low-dose group and the cisplatin+GLP-2 high-dose group was significantly reduced from D6 to D18.

Compared to the cisplatin group, the tumor volume in the cisplatin+GLP-2 low-dose group was significantly reduced from D15 to D18, and the tumor volume in the cisplatin+GLP-2 high-dose group was significantly reduced from D12 to D18.

TABLE 11

Effect of *Ganoderma lucidum* polysaccharide GLP-2 combined with chemotherapy on tumor volume in H22-bearing mice ($\bar{x} \pm s$)

| Group | Tumor volume (mm$^3$) | | | | | | |
|---|---|---|---|---|---|---|---|
| | D0 | D3 | D6 | D9 | D12 | D15 | D18 |
| Model control group | 158.2 ± 39.9 | 257.5 ± 76.4 | 540.5 ± 180.1 | 826.1 ± 332.1 | 1438.2 ± 779.3 | 1971.4 ± 998.2 | 3091.1 ± 1537.4 |
| Cisplatin | 167.9 ± 42.2 | 205.9 ± 122.5 | 417.4 ± 228.3 | 577.3 ± 420.2 | 798± 676.5$^+$ | 952.7± 711.9$^+$ | 1097± 805.3$^+$ |
| Cisplatin + GLP-2 low-dose group | 156 ± 39.6 | 297.3 ± 172.3 | 363.3± 108.4$^+$ | 458.9± 1226.3$^+$ | 539.6± 288.6$^+$ | 557.5± 212$^{+\#}$ | 659.8± 407$^{+\#}$ |

TABLE 11-continued

Effect of *Ganoderma lucidum* polysaccharide GLP-2 combined with
chemotherapy on tumor volume in H22-bearing mice ($\bar{x} \pm s$)

| Group | Tumor volume (mm³) | | | | | | |
|---|---|---|---|---|---|---|---|
| | D0 | D3 | D6 | D9 | D12 | D15 | D18 |
| Cisplatin + GLP-2 high-dose group | 174.1 ± 47.5 | 237.1 ± 133.5 | 331.7 ± 176.1+ | 373.8 ± 191.4+ | 383.7 ± 185.9+# | 490.7 ± 243.7+# | 551.5 ± 225.4+# |

Note:
Compared to the model control group, +P < 0.05; Compared to the cisplatin group, #P < 0.05.

Effect of *Ganoderma lucidum* Polysaccharide GLP-2 Combined with Chemotherapy on Relative Tumor Growth Inhibition Rate in H22-Bearing Mice As indicated in Tables 12 and 136, compared to the model control group, the relative tumor growth inhibition rate in the cisplatin group from D12 to D18 was over 45%, specifically 47.29%, 52.99%, and 64.27%; the relative tumor growth inhibition rate in the cisplatin+GLP-2 low-dose group from D9 to D18 was over 45%, specifically 47.69%, 64.57%, 72.10%, and 79.82%; the relative tumor growth inhibition rate in the cisplatin+GLP-2 high-dose group from D6 to D18 was over 45%, specifically 45.85%, 60.34%, 76.86%, 77.87%, and 83.93%.

Compared to the cisplatin group, the relative tumor growth inhibition rate in the cisplatin+GLP-2 low-dose group from D15 to D18 was 40.64% and 43.52% (P<0.05), and the relative tumor growth inhibition rate in the cisplatin+GLP-2 high-dose group from D12 to D18 was 56.10%, 52.93%, and 55.03% (P<0.05).

TABLE 12

Effect of *Ganoderma lucidum* polysaccharide GLP-2 combined
with chemotherapy on relative tumor growth inhibition rate in
H22-bearing mice (vs. the model control group)

| Group | Relative tumor growth inhibition rate (compared to model control group) (%) | | | | | |
|---|---|---|---|---|---|---|
| | D3 | D6 | D9 | D12 | D15 | D18 |
| Model control group | — | — | — | — | — | — |
| Cisplatin | 30.90 | 25.54 | 33.52 | 47.29+ | 52.99+ | 64.27+ |
| Cisplatin + GLP-2 low-dose group | −5.78 | 31.59+ | 47.69+ | 64.57+ | 72.10+ | 79.82+ |
| Cisplatin + GLP-2 high-dose group | 22.01 | 45.85+ | 60.34+ | 76.86+ | 77.87+ | 83.93+ |

Note:
Compared to the model control group, +P < 0.05.

TABLE 13

Effect of *Ganoderma lucidum* polysaccharide GLP-2 combined
with chemotherapy on relative tumor growth inhibition
rate in H22-bearing mice (vs. the cisplatin group)

| Group | Relative tumor growth inhibition rate (compared to cisplatin group) (%) | | | | | |
|---|---|---|---|---|---|---|
| | D3 | D6 | D9 | D12 | D15 | D18 |
| Cisplatin | — | — | — | — | — | — |
| Cisplatin + GLP-2 low-dose group | −53.08 | 8.11 | 21.31 | 32.78 | 40.64# | 43.52# |
| Cisplatin + GLP-2 high-dose group | −12.86 | 27.27 | 40.33 | 56.10# | 52.93# | 55.03# |

Note:
Compared to the cisplatin group, #P < 0.05.

Effect of *Ganoderma lucidum* Polysaccharide GLP-2 Combined with Chemotherapy on Organ Coefficients and Tumor Growth Inhibition Rates in H22-Bearing Mice As indicated in Table 14, compared to the model group, the tumor index, spleen index, and thymus index were significantly reduced in the cisplatin group, the cisplatin+GLP-2 low-dose dose group, and the cisplatin+GLP-2 high-dose group. Compared to the cisplatin group, the tumor index was significantly reduced in the cisplatin+GLP-2 low-dose group and the cisplatin+GLP-2 high-dose group. Compared to the normal group, the spleen index was significantly reduced in the model control group; the thymus index was significantly reduced in the cisplatin group, the cisplatin+GLP-2 low-dose group, and the cisplatin+GLP-2 high-dose group.

Compared to the model control group, the tumor growth inhibition rate was 57.3% in the cisplatin group, and 76.4% and 79.3% in the cisplatin+GLP-2 low-dose and high-dose groups, respectively. Compared to the cisplatin group, the tumor growth inhibition rate was 44.8% and 51.6% in the cisplatin+GLP-2 low-dose and high-dose groups, respectively.

TABLE 14

Effect of *Ganoderma lucidum* polysaccharide GLP-2 combined with chemotherapy on organ indices and tumor growth inhibition rates in H22-bearing mice

| Group | Tumor index (%) | Spleen index (mg/g) | Thymus index (mg/g) | Tumor growth inhibition rate (%) vs. the model control group | Tumor growth inhibition rate (%) vs. the cisplatin group |
|---|---|---|---|---|---|
| Model control group | 10.2 ± 5.1 | 4.9± 1.5* | 1.3 ± 0.3 | — | — |
| Cisplatin | 5.7± 4.6+ | 3.1± 1+ | 0.6± 0.4+* | 57.3+ | — |
| Cisplatin + GLP-2 low-dose group | 3.6± 1.6+# | 2.8± 1.1+ | 0.5± 0.2+* | 76.4+ | 44.8# |
| Cisplatin + GLP-2 high-dose group | 2.9± 1.6+# | 2.6± 0.1+ | 0.8± 0.2+* | 79.3+ | 51.6# |
| Normal group | — | 2.3 ± 0.1 | 1.4 ± 0.2 | — | — |

Note:
Compared to the model control group, $^+P < 0.05$; Compared to the cisplatin group, $^\#P < 0.05$; Compared to the normal group, $^*P < 0.05$.

Figure 29:
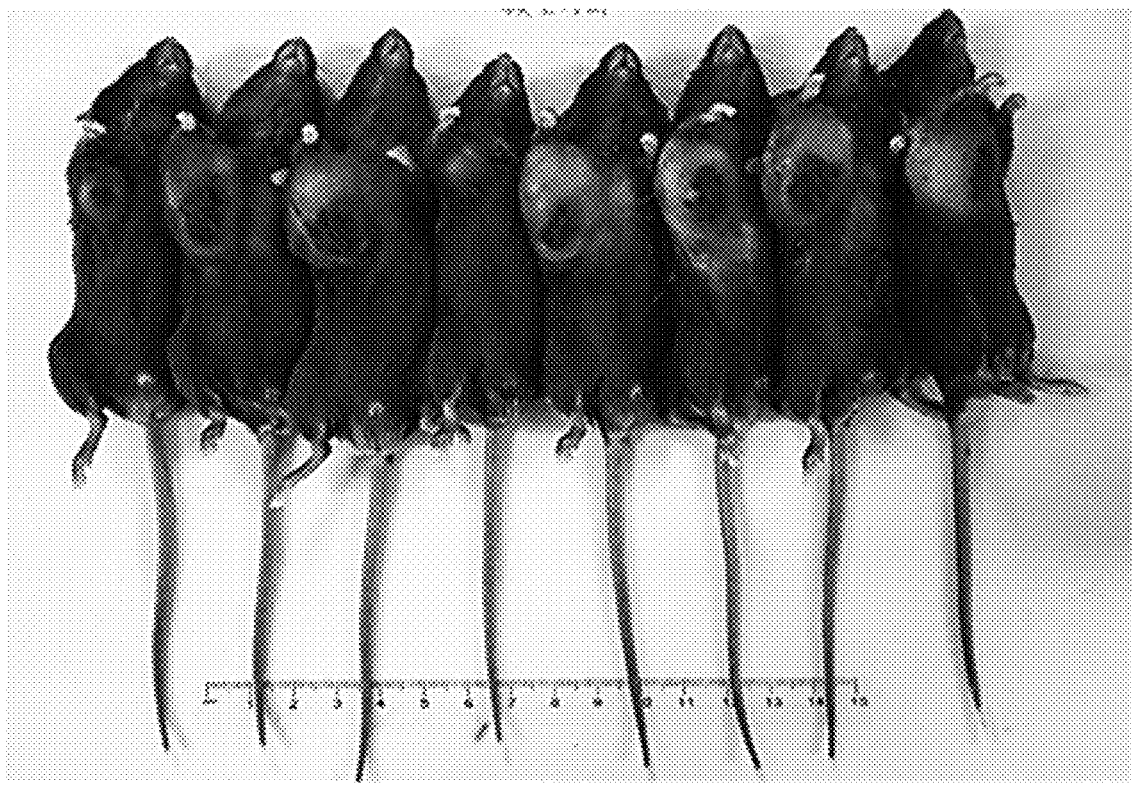
FIG. 29: Schematic diagram of the control group of H22-bearing mouse model treated with *Ganoderma lucidum* polysaccharide GLP-2 combined with chemotherapy, provided by an embodiment of the invention.
Figure 30:
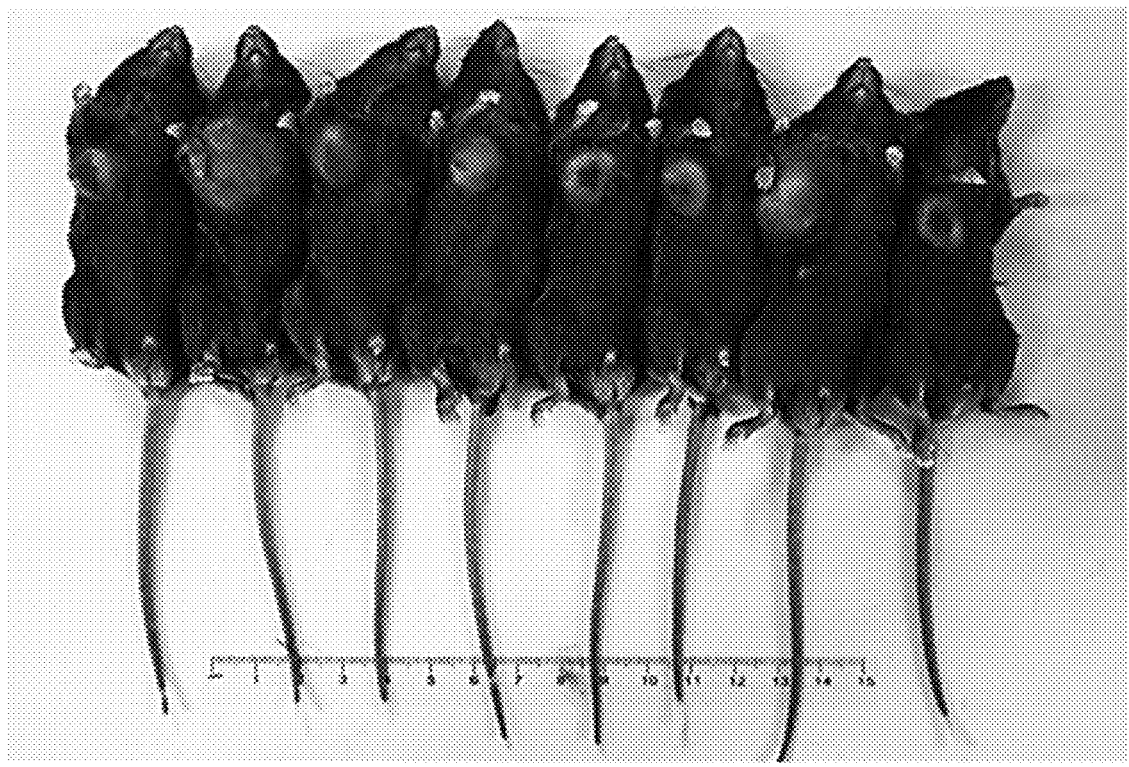
FIG. 30: Schematic diagram of the cisplatin group of H22-bearing mice treated with *Ganoderma lucidum* polysaccharide GLP-2 combined with chemotherapy, provided by an embodiment of the invention.
Figure 31:
FIG. 31: Schematic diagram of the cisplatin+low-dose GLP-2 group of H22-bearing mice treated with *Ganoderma lucidum* polysaccharide GLP-2 combined with chemotherapy, provided by an embodiment of the invention.
Figure 32:
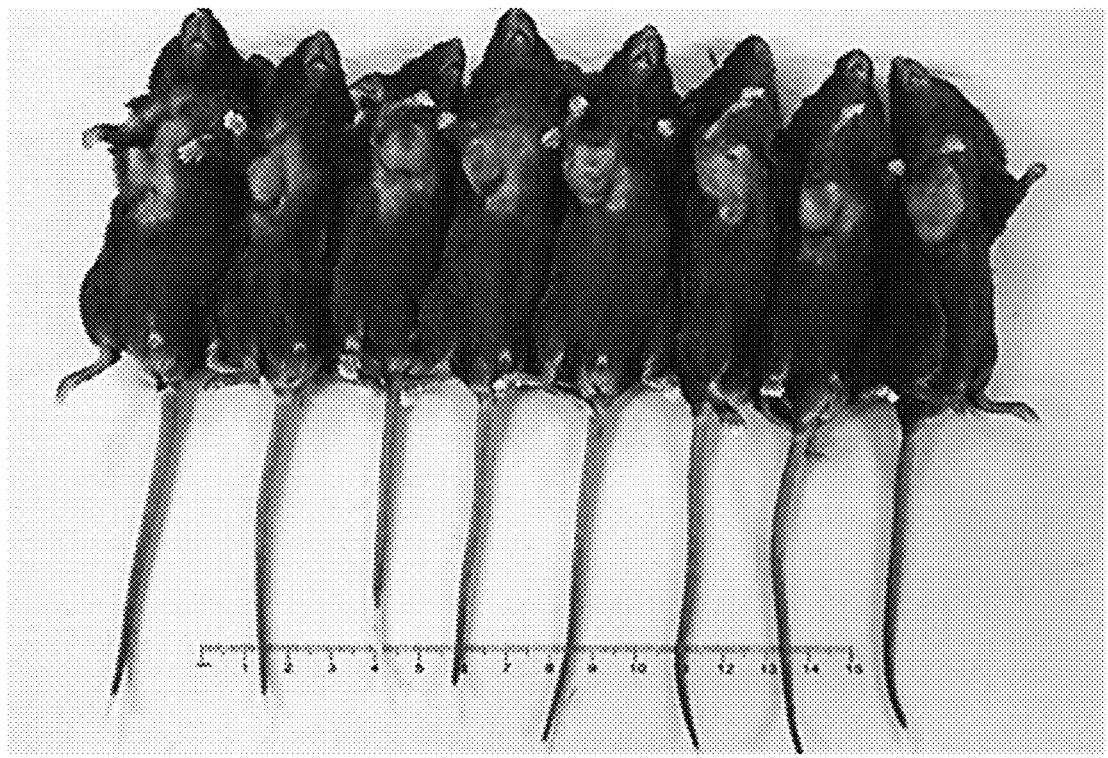
FIG. 32: Schematic diagram of the cisplatin+high-dose GLP-2 group of H22-bearing mice treated with *Ganoderma lucidum* polysaccharide GLP-2 combined with chemotherapy, provided by an embodiment of the invention.

FIGS. 29-32 show images of the tumor-bearing mice, corresponding to the groups as follows: FIG. 29: model control group, FIG. 30: cisplatin group, FIG. 31: cisplatin+GLP-2 low-dose group, FIG. 32: cisplatin+GLP-2 high-dose group.

Figure 33:
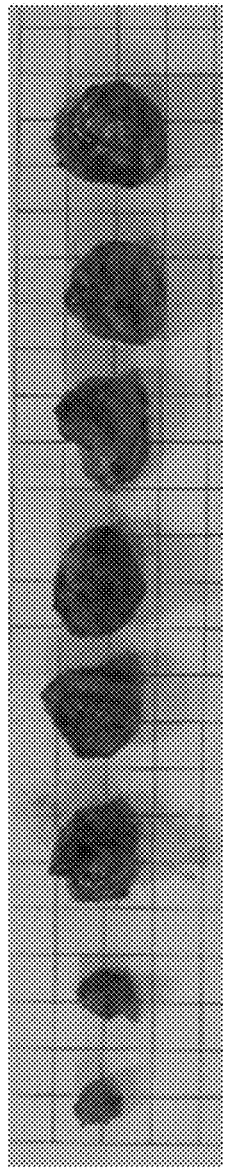
FIG. 33: Schematic diagram of the control group of H22-bearing mouse tumor model treated with *Ganoderma lucidum* polysaccharide GLP-2 combined with chemotherapy, provided by an embodiment of the invention.
Figure 34:
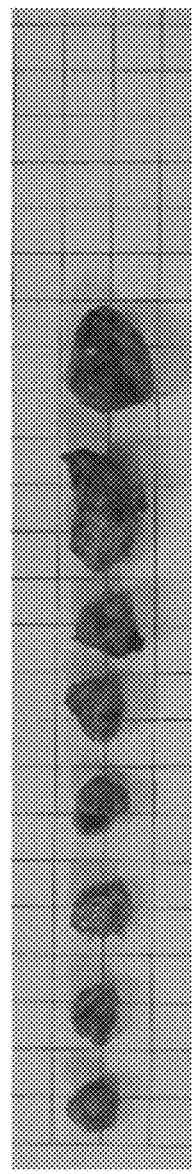
FIG. 34: Schematic diagram of the cisplatin group of H22-bearing mouse tumor treated with *Ganoderma lucidum* polysaccharide GLP-2 combined with chemotherapy, provided by an embodiment of the invention.
Figure 35:
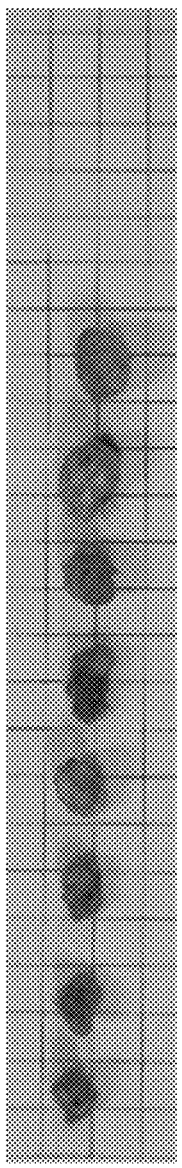
FIG. 35: Schematic diagram of the cisplatin+low-dose GLP-2 group of H22-bearing mouse tumor treated with *Ganoderma lucidum* polysaccharide GLP-2 combined with chemotherapy, provided by an embodiment of the invention.
Figure 36:
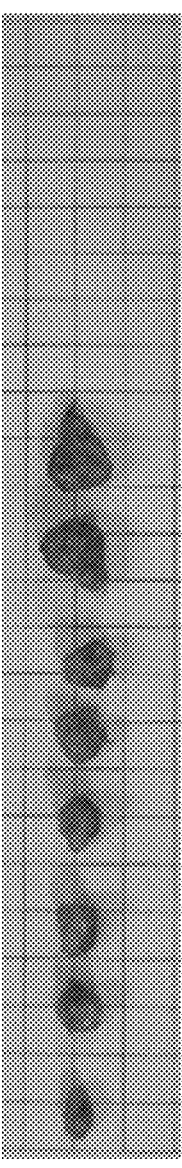
FIG. 36: Schematic diagram of the cisplatin+high-dose GLP-2 group of H22-bearing mouse tumor treated with *Ganoderma lucidum* polysaccharide GLP-2 combined with chemotherapy, provided by an embodiment of the invention.
Figure 37A:
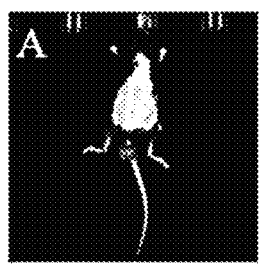
FIG. 37A to FIG. 37H: Schematic diagram of the effect of *Ganoderma lucidum* polysaccharide GLP-2 combined with chemotherapy on the tumor of orthotopic H22-bearing mice (binning: 8×8; T=30 s), provided by an embodiment of the invention.
Figure 37B:
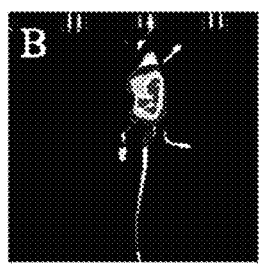
Figure 37C:
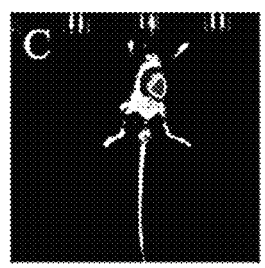
Figure 37D:
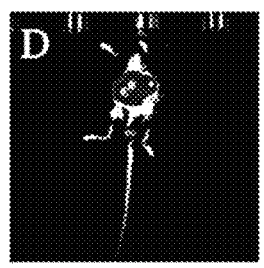
Figure 37E:
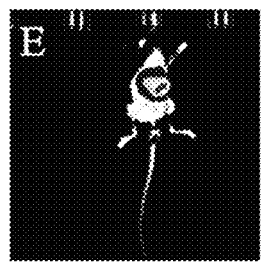
Figure 37F:
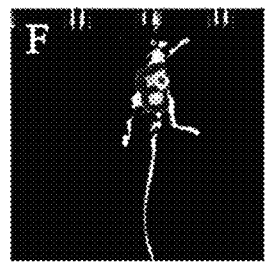
Figure 37G:
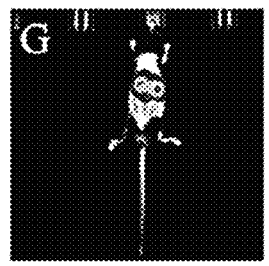
Figure 37H:
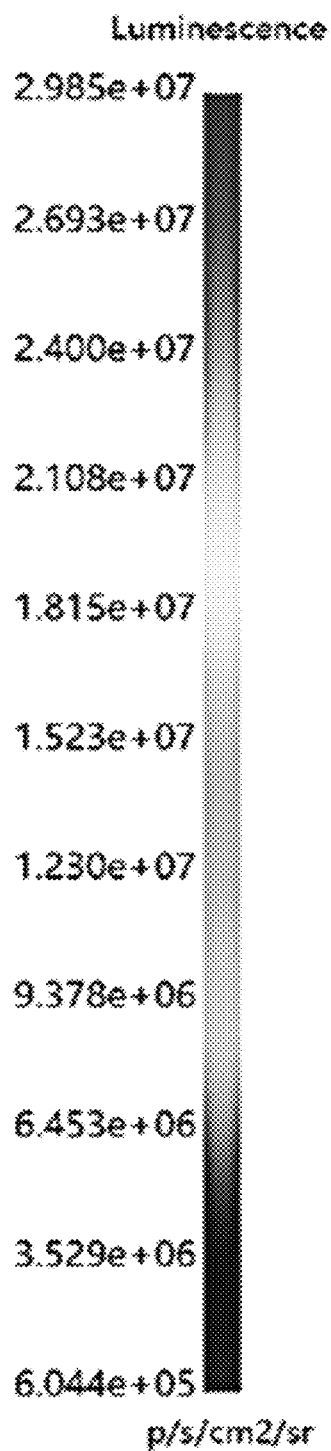

FIGS. 33-36 show images of the tumors in the tumor-bearing mice, corresponding to the groups as follows: FIG. 33: model control group, FIG. 34: cisplatin group, FIG. 35: cisplatin+GLP-2 low-dose group, FIG. 36: cisplatin+GLP-2 high-dose group.

Conclusion

*Ganoderma lucidum* Polysaccharide GLP-2 combined with cisplatin significantly inhibits tumor growth in H22-bearing mice and exhibits a significant synergistic effect.

Experimental Study on the Antitumor Effect of *Ganoderma lucidum* Polysaccharide GLP-2 Combined with Chemotherapy on Orthotopic H22-Bearing Mice and Study Data Experimental Objective To study the effect of *Ganoderma lucidum* polysaccharide GLP-2 combined with chemotherapy on orthotopic H22-bearing mice which are prepared by implanting H22 hepatoma tumors in the right axilla of C57 mice. This study aims to provide experimental evidence for clinical studies of GLP-2.

Experimental Materials

Test Sample

*Ganoderma lucidum* polysaccharide GLP-2, batch number: ALM20200518A1, provided by Shenzhen Aolimei Oncology Medical Technology Co., Ltd.

Control

Kanglaite soft capsules, batch number: 20211006, Zhejiang Kanglaite Pharmaceutical Co., Ltd.; cisplatin injection, batch number: 601211204, Jiangsu Hansoh Pharmaceutical Co., Ltd.

Laboratory Animals

60 SPF-grade male C57 mice, weighing 12-15 g, provided by Hunan SJA Laboratory Animal Co., Ltd. Laboratory animal production license number: SCXK (Xiang) 2019-0004. The animals were housed in Barrier Environment Laboratory D of Hunan Puruima Pharmaceutical Research Center Co., Ltd., under the laboratory animal use license number: SYXK (Xiang) 2020-0015.

Main Reagents 0.9% sodium chloride injection, batch number: 21071401C, Hunan Kangyuan Pharmaceutical Co., Ltd.; ALT assay kit, batch number: 201751; AST assay kit, batch number: 110620; CRE assay kit, batch number: 111644; BUN assay kit, batch number: 201749, all manufactured by Wako Pure Chemical Industries, Ltd. of Japan.

Main Instruments

AR223CN Electronic Scale, Ohaus Instruments (Changzhou) Co., Ltd.; LABOSPECT003 Automatic Biochemical Analyzer, Hitachi, Japan; AniView100 Multimodal Animal In Vivo Imaging System, ANDOR; TDZ5-WS Benchtop Multi-Tube Automatic Balance Centrifuge, Hunan Kaida Industrial Development Co., Ltd.; ME2002E Electronic Scale, Shimadzu Corporation, Japan; Flow Cytometer, BD Biosciences; ASP200S Fully Automatic Tissue Dehydrator, ASP300S Fully Automatic Tissue Dehydrator, TP1020 Fully Automatic Dehydrator, HI1210 Slide Spreader, HI1220 Slide Dryer, RM2235 Paraffin Microtome, EG1150H+C Tissue Embedding Station, AutoStainer XL Automatic Slide Stainer+CV5030 Automatic Cover Slipper, BX43 Biological Microscope+MD50 Digital Imaging System, CX31 Biological Microscope, all from Leica, Germany.

Experimental Methods

Liver cancer (H22) cells, labeled with Luc fluorescent marker at a concentration of $1\times10^7$ cells/mL, were initially inoculated into the peritoneal cavity of 5 male C57 mice. After the development of ascites, the ascitic fluid was aseptically extracted, washed with HBSS buffer, centrifuged to discard the supernatant, and stained with Trypan Blue, and cells in the ascitic fluid were counted under a microscope. The cell concentration was adjusted to $1\times10^{13}$/mL with HBSS buffer and inoculated into the right hepatic region of 45 male C57 mice, at a volume of 10 µL per mouse, to prepare the orthotopic tumor-bearing mice. One week later, the liver tumor formation in mice was detected using a small animal in vivo imaging system. Based on tumor size, the mice were randomized into groups: model control group, cisplatin group (4 mg/kg), Kanglaite soft capsule group (1,404 mg/kg), cisplatin+Kanglaite soft capsule group (4+1, 404 mg/kg), cisplatin+GLP-2 low-dose group (4+130 mg/kg), and cisplatin+GLP-2 high-dose group (4+1,170 mg/kg), with 6 mice per group. An additional 6 mice served as the normal control group. The normal control group and the model control group were administered pure water by oral gavage. The chemotherapy group received intraperitoneal injections of cisplatin, and the other groups were administered their respective drug solutions by oral gavage (20 mL/kg) or intraperitoneal injection (10 mL/kg), once daily for 14 consecutive days. After the last dose, blood was collected from the orbital plexus to test blood WBC, RBC, liver and kidney function indicators (ALT, AST, BUN, CRE), and $CD3^+/CD4^+$, $CD3^+/CD8^+$ ratios. The spleen, thymus, and tumors were weighed to calculate organ coefficients.

Dosage Design

Based on previous experimental results, *Ganoderma lucidum* polysaccharide GLP-2 was administered at a low dose of 130 mg/kg and a high dose of 1170 mg/kg as shown in Table 15.

The proposed clinical dose for Kanglaite soft capsules is 0.45 g per capsule, 6 capsules per dose, 4 doses per day, which totals 10.8 g per day. When converted to an equivalent mouse dose based on body surface area, it is calculated as 10.8 g/day×0.0026/0.02 kg=1,404 mg/kg. This study used the proposed clinical dose as a basis for the experiment.

Rationale for cisplatin dosage design: Based on the clinical dosage of cisplatin, which should not exceed 100 $mg/m^2$ per person per day, and considering the tolerance of mice to cisplatin, a dose of 4 mg/kg has been selected as the administration dosage.

TABLE 15

Experimental groups and dosage design

| Group | Dose (mg/kg) | Method of administration | Frequency of administration |
|---|---|---|---|
| Normal control group | — | Oral gavage | Once daily |
| Model control group | — | Oral gavage | Once daily |
| Cisplatin group | 4 | Intraperitoneal injection | Once every 3 days |
| Kanglaite soft capsule group | 1404 | Oral gavage | Once daily |
| Cisplatin + Kanglaite soft capsule group | 4 + 1404 | Intraperitoneal injection + oral gavage | Cisplatin, once every 3 days; Kanglaite soft capsule, once daily |
| Cisplatin + GLP-2 low-dose group | 4 + 130 | Intraperitoneal injection + oral gavage | Cisplatin, once every 3 days; GLP-2, once daily |
| Cisplatin + GLP-2 high-dose group | 4 + 1170 | Intraperitoneal injection + oral gavage | Cisplatin, once every 3 days, GLP-2, once daily |

Test Indicators

Efficacy Indicators

Animal survival and general condition: Weight was recorded weekly, along with any deaths among the animals.

Tumor volume measurement: Tumor volume changes were measured weekly using small animal in vivo imaging technology.

Hematological tests: After the last dose, routine blood tests (WBC and RBC) and biochemical tests (liver and kidney functions) were performed.

Immune organs: The thymus, spleen, tumor, and liver were weighed, and organ coefficients were calculated as follows: organ coefficient (%)=organ weight/fasting body weight×100%.

$CD4^+$ and $CD8^+$ content measurement: After the last dose, lymphocyte subtypes $CD3^+/CD4^+$ and $CD3^+/CD8^+$ in the blood were measured using flow cytometry.

Data Processing and Statistical Analysis

Significant figures of the study data were rounded according to the nearest whole number. Statistical analysis was conducted in accordance with the center's SOP, using SPSS software. Measurement data are expressed as mean±standard deviation ($\bar{x}$±s), and normality and homogeneity of variance were tested using Leven's test. If not statistically significant (P>0.05), one-way ANOVA was used for statistical analysis. If ANOVA was statistically significant (P≤0.05), the LSD test (parametric method) was used for comparison analysis. If the variance was not homogeneous (P≤0.05), the Kruskal-Wallis test was employed. If the Kruskal-Wallis test was statistically significant (P≤0.05), the Dunnett's Test (non-parametric method) was used for comparison analysis. Statistical significance was determined at α=0.05, where P≤0.05 indicates statistical significance and P≤0.01 indicates highly significant differences.

Experimental Results

Animal Mortality

As shown in Table 16, before administration, the mice exhibited normal activity, movement, and gait; after administration, a reduction in activity was observed, and tumor growth impacted their food and water intake, leading to minimal weight gain. In the model control group, 2M01 died on D12; in the cisplatin group, 3M01/3M05 and 3M02 died on D9 and D10, respectively; in the Kanglaite soft capsule group, 4M01 died on D9; in the cisplatin+Kanglaite soft capsule group, 5M01 and 5M06 died on D8 and D11, respectively; in the cisplatin+GLP-2 high-dose group, 7M03, 7M04, and 7M05 died on D8, D12, and D11.

The mortality rates for each group were 0%, 16.7%, 50.0%, 16.7%, 16.7%, 0%, and 50.0%, respectively. The cisplatin group and the cisplatin+GLP-2 high-dose group had the highest mortality rate, both reaching 50.0%.

TABLE 16

Statistics on the number of surviving animals and mortality rate in each group

| Group | Dose (mg/kg) | Number of animals | Number of deaths | Number of surviving animals | Mortality rate (%) |
|---|---|---|---|---|---|
| Normal control group | — | 6 | 0 | 6 | 0 |
| Model control group | — | 6 | 1 | 5 | 16.7 |
| Cisplatin group | 4 | 6 | 3 | 3 | 50.0 |
| Kanglaite soft capsule group | 1404 | 6 | 1 | 5 | 16.7 |
| Cisplatin + Kanglaite soft capsule group | 4 + 1404 | 6 | 1 | 5 | 16.7 |

TABLE 16-continued

Statistics on the number of surviving animals and mortality rate in each group

| Group | Dose (mg/kg) | Number of animals | Number of deaths | Number of surviving animals | Mortality rate (%) |
|---|---|---|---|---|---|
| Cisplatin + GLP-2 low-dose group | 4 + 130 | 6 | 0 | 6 | 0 |
| Cisplatin + GLP-2 high-dose group | 4 + 1170 | 6 | 3 | 3 | 50.0 |

Effect of *Ganoderma lucidum* Polysaccharide GLP-2 Combined with Chemotherapy on Body Weight of Orthotopic H22-Bearing Mice As shown in Table 17, compared to the normal control group, the body weight of mice in the model control group significantly decreased on W2 after administration (P≤0.01). Compared to the model control group, the body weight of mice in both the cisplatin group, the cisplatin+Kanglaite soft capsule group, the cisplatin+GLP-2 low-dose group, and the cisplatin+GLP-2 high-dose group significantly decreased on W1 and W2 after administration (P≤0.05 or P≤0.01). Compared to the cisplatin group, the body weight of mice in the Kanglaite soft capsule group significantly increased on W2 after administration (P≤0.05 or P≤0.01). Compared to the Kanglaite soft capsule group, the body weight of mice in the cisplatin+GLP-2 low-dose and high-dose groups significantly decreased on W1 and W2 after administration (P≤0.05 or P≤0.01). There was no significant statistical difference between treatment groups compared to the cisplatin+Kanglaite soft capsule group.

TABLE 17

Effect of *Ganoderma lucidum* polysaccharide GLP-2 combined with chemotherapy on body weight of orthotopic H22-bearing mice ($\bar{x} \pm s$)

| Group | Weight (g) | | |
|---|---|---|---|
| | W0 | W1 | W2 |
| Normal control group | 19.9 ± 1.2 | 18.9 ± 1.6 | 22.4 ± 1.7 |
| Model control group | 18.3 ± 1.9 | 19.1 ± 1.9 | 19.6± 1.8++ |
| Cisplatin group | 18.5 ± 1.3 | 16.9± 1.8* | 15.1± 1.6** |
| Kanglaite soft capsule group | 18.2 ± 1.5 | 18.7 ± 2.9 | 19.0± 1.3## |
| Cisplatin + Kanglaite soft capsule group | 18.6 ± 0.9 | 15.5± 2.3**&& | 16.6± 3.7**& |

TABLE 17-continued

Effect of *Ganoderma lucidum* polysaccharide GLP-2 combined with chemotherapy on body weight of orthotopic H22-bearing mice ($\bar{x} \pm s$)

| Group | Weight (g) | | |
|---|---|---|---|
| | W0 | W1 | W2 |
| Cisplatin + GLP-2 low-dose group | 18.0 ± 1.0 | 16.7± 1.2*& | 15.8± 1.5**&& |
| Cisplatin + GLP-2 high-dose group | 18.3 ± 1.1 | 15.3± 1.5**&& | 14.1± 1.5**&& |

Note:
Compared to the normal control group, ++P ≤ 0.01; compared to the model control group, *P ≤ 0.05, **P ≤ 0.01; compared to the cisplatin group, *P ≤ 0.05, **P ≤ 0.01; compared to the Kanglaite soft capsule group, &P ≤ 0.05, &&P ≤ 0.01; compared to the cisplatin + Kanglaite soft capsule group, *P ≤ 0.05, **P ≤ 0.01.

Effect of *Ganoderma lucidum* Polysaccharide GLP-2 Combined with Chemotherapy on Tumors in Orthotopic H22-Bearing Mice As shown in FIGS. 37A-37H, 38, and Table 18, compared to the normal control group, the tumors in the mice of the model control group significantly increased (P≤0.01); compared to the model control group, the tumors in the mice of the cisplatin+GLP-2 low-dose group and the Kanglaite soft capsule group significantly decreased on W1 and W2 after administration (P≤0.05 or P≤0.01); the tumors in the mice of the cisplatin group and the cisplatin+Kanglaite soft capsule group significantly decreased on W2 after administration (P≤0.05 or P≤0.01). There was no statistical difference between the groups when compared to the cisplatin group. Compared to the Kanglaite soft capsule group, the tumors in the mice of the cisplatin+Kanglaite soft capsule group significantly increased on W1 after administration (P≤0.05 or P≤0.01); the tumors in the mice of the cisplatin+GLP-2 high-dose group significantly increased on W1 and W2 after administration (P≤0.05). Compared to the cisplatin+Kanglaite soft capsule group, the tumors in the mice of the cisplatin+GLP-2 low-dose group significantly decreased on W1 and W2 after administration (P≤0.05); there was no statistically significant difference in the rest of the groups.

As shown in FIG. 37A to FIG. 37H, the corresponding groups are as follows: A: normal group, B: model control group, C: cisplatin group, D: Kanglaite soft capsule group, E: cisplatin+Kanglaite soft capsule group, F: cisplatin+GLP-2 low-dose group, G: cisplatin+GLP-2 high-dose group.

Figure 38:
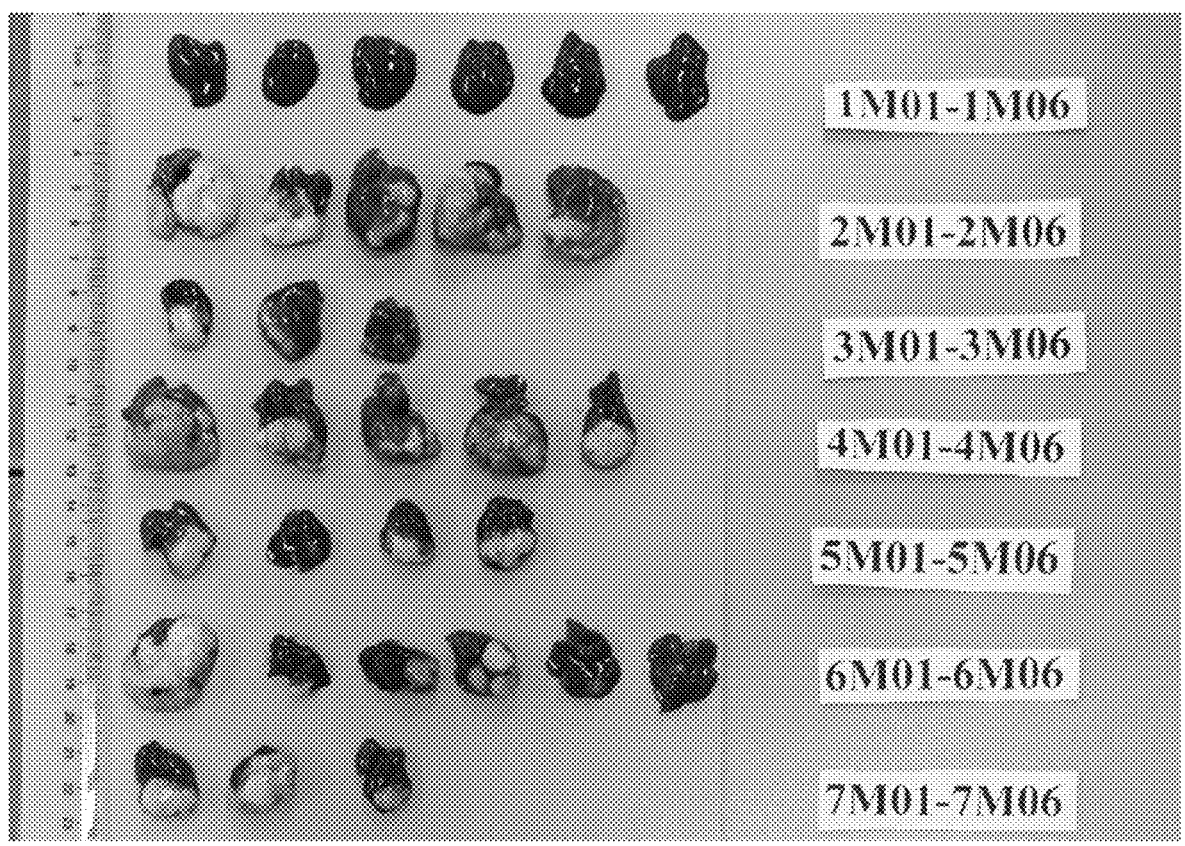
FIG. 38: Schematic diagram of the effect of *Ganoderma lucidum* polysaccharide GLP-2 combined with chemotherapy on the tumor of orthotopic H22-bearing mice, provided by an embodiment of the invention.
Figure 39A:
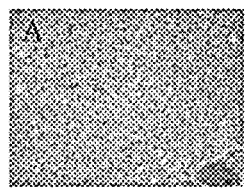
FIG. 39A to FIG. 39G: Schematic diagram of the effect of *Ganoderma lucidum* polysaccharide GLP-2 combined with chemotherapy on the liver of orthotopic H22-bearing mice (×200), provided by an embodiment of the invention.
Figure 39B:
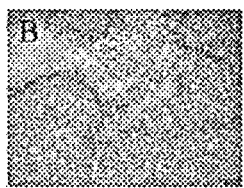
Figure 39C:
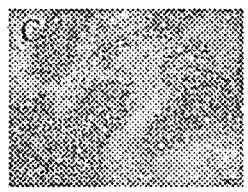
Figure 39D:
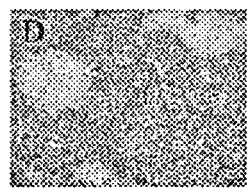
Figure 39E:
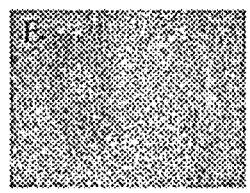
Figure 39F:
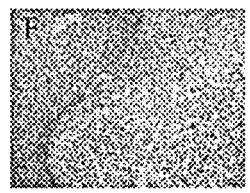
Figure 39G:
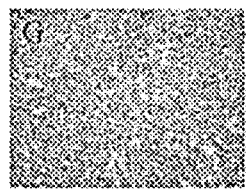
Figure 40A:
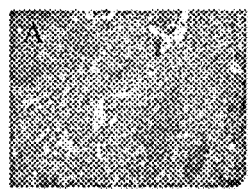
FIG. 40A to FIG. 40G: Schematic diagram of the effect of *Ganoderma lucidum* polysaccharide GLP-2 combined with chemotherapy on the spleen of orthotopic H22-bearing mice (×200), provided by an embodiment of the invention.
Figure 40B:
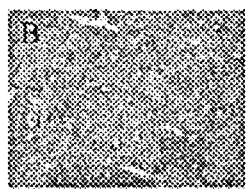
Figure 40C:
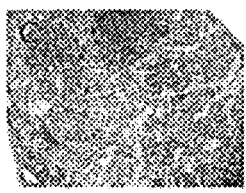
Figure 40D:
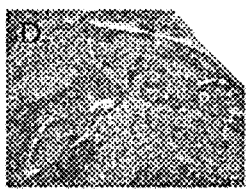
Figure 40E:
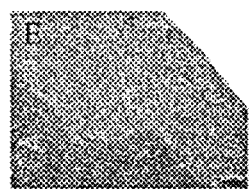
Figure 40F:
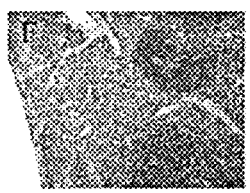
Figure 40G:
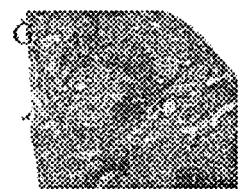

As shown in FIG. 38, the corresponding groups are as follows: 1: normal group, 2: model control group, 3: cisplatin group, 4: Kanglaite soft capsule group, 5: cisplatin+Kanglaite soft capsule group, 6: cisplatin+GLP-2 low-dose group, 7: cisplatin+GLP-2 high-dose group.

TABLE 18

Effect of *Ganoderma lucidum* polysaccharide GLP-2 combined with chemotherapy on tumors in orthotopic H22-bearing mice ($\bar{x} \pm s$)

| Group | W0 | | W1 | | W2 | |
|---|---|---|---|---|---|---|
| | Tumor (P/s/cm²/sr) | Number of animals | Tumor (P/s/cm²/sr) | Number of animals | Tumor (P/s/cm²/sr) | Number of animals |
| Normal control group | 0 ± 0 | 6 | 0 ± 0 | 6 | 0 ± 0 | 6 |
| Model control group | 3897500 ± 2651893++ | 6 | 17515000 ± 2702626++ | 6 | 20032000 ± 3407219++ | 5 |
| Cisplatin group | 3756000 ± 2439052 | 6 | 12898500 ± 3588676 | 6 | 11871333 ± 2780016& | 3 |
| Kanglaite soft capsule group | 3888167 ± 2341708 | 6 | 5906333 ± 2710545** | 6 | 6040000 ± 2159132** | 5 |

TABLE 18-continued

Effect of *Ganoderma lucidum* polysaccharide GLP-2 combined with chemotherapy on tumors in orthotopic H22-bearing mice ($\bar{x} \pm s$)

| Group | W0 Tumor (P/s/cm²/sr) | W0 Number of animals | W1 Tumor (P/s/cm²/sr) | W1 Number of animals | W2 Tumor (P/s/cm²/sr) | W2 Number of animals |
|---|---|---|---|---|---|---|
| Cisplatin + Kanglaite soft capsule group | 3968117 ± 2511453 | 6 | 17516667 ± 3438157<sup>&&</sup> | 6 | 10266000 ± 2143720** | 5 |
| Cisplatin + GLP-2 low-dose group | 3751083 ± 2310570 | 6 | 9081667 ± 2731045★★ | 6 | 4402333 ± 1686745*** | 6 |
| Cisplatin + GLP-2 high-dose group | 3905167 ± 2143597 | 6 | 13835333 ± 2778074<sup>&</sup> | 6 | 15633333 ± 2160504<sup>&</sup> | 3 |

Note:
Compared to the normal control group, $^{++}P \leq 0.01$; compared to the model control group, $^*P \leq 0.05$, $^{**}P \leq 0.01$; compared to the cisplatin group, $^{\#}P \leq 0.05$, $^{\#\#}P \leq 0.01$; compared to the Kanglaite soft capsule group, $^{\&}P \leq 0.05$, $^{\&\&}P \leq 0.01$; compared to the cisplatin + Kanglaite soft capsule group, $^{\star}P \leq 0.05$, $^{\star\star}P \leq 0.01$.

Effect of *Ganoderma lucidum* Polysaccharide GLP-2 Combined with Chemotherapy on Organ Coefficients and Tumor Growth Inhibition Rates in Orthotopic H22-Bearing Mice As shown in Table 19, compared to the normal control group, the organ coefficients of the spleen and liver tissues in the model control group significantly increased ($P \leq 0.05$ or $P \leq 0.01$). Compared to the model control group, the thymus and spleen coefficients in both the cisplatin+GLP-2 low-dose and high-dose groups significantly decreased ($P \leq 0.05$ or $P \leq 0.01$), and the thymus and spleen coefficients in both the cisplatin group and the cisplatin+Kanglaite soft capsule group significantly decreased ($P \leq 0.05$). There was no statistically difference across the treatment groups when compared to the cisplatin group. Compared to the Kanglaite soft capsule group, the thymus and spleen coefficients in the cisplatin+GLP-2 low-dose and high-dose groups significantly decreased ($P \leq 0.05$ or $P \leq 0.01$), and the spleen coefficients in the cisplatin+Kanglaite soft capsule group significantly decreased ($P \leq 0.05$ or $P \leq 0.01$); there was no statistically significant difference in the remaining treatment groups.

TABLE 19

Effect of *Ganoderma lucidum* polysaccharide GLP-2 combined with chemotherapy on organ coefficients in orthotopic H22-bearing mice ($\bar{x} \pm s$)

| Group | Thymus coefficient | Spleen coefficient | Liver coefficient |
|---|---|---|---|
| Normal control group | 0.191 ± 0.039 | 0.372 ± 0.066 | 5.325 ± 0.205 |
| Model control group | 0.191 ± 0.162 | 1.151± 0.713<sup>++</sup> | 12.497± 6.659<sup>+</sup> |
| Cisplatin group | 0.078 ± 0.023* | 0.524 ± 0.295* | 11.365 ± 3.599 |
| Kanglaite soft capsule group | 0.144 ± 0.079 | 1.116 ± 0.537 | 14.206 ± 8.001 |
| Cisplatin + Kanglaite soft capsule group | 0.074± 0.063* | 0.548± 0.351*<sup>&</sup> | 9.405 ± 2.800 |
| Cisplatin + GLP-2 low-dose group | 0.054± 0.036<sup>&</sup> | 0.440± 0.119<sup>&&</sup> | 10.025 ± 7.69 |
| Cisplatin + GLP-2 high-dose group | 0.044± 0.038<sup>&</sup> | 0.412± 0.314<sup>&&</sup> | 11.199 ± 4.044 |

Note:
Compared to the normal control group, $^{+}P \leq 0.05$, $^{++}P \leq 0.01$; compared to the model control group, $^*P \leq 0.05$, $^{**}P \leq 0.01$; compared to the cisplatin group, $^{\#}P \leq 0.05$; compared to the Kanglaite soft capsule group, $^{\&}P \leq 0.05$, $^{\&\&}P \leq 0.01$.

Effect of *Ganoderma lucidum* Polysaccharide GLP-2 Combined with Chemotherapy on Blood Biochemical Indicators in Orthotopic H22-Bearing Mice As shown in Table 20, compared to the normal control group, the blood AST and CRE level of mice in the model control group significantly increased ($P \leq 0.01$); compared to the model control group, the blood WBC level of mice in the cisplatin+GLP-2 low-dose group and the Kanglaite soft capsule group significantly decreased ($P \leq 0.05$), and blood BUN level of mice in the cisplatin+GLP-2 high-dose group significantly decreased ($P \leq 0.05$). Compared to the cisplatin group, the blood BUN level in the mice of the cisplatin+GLP-2 high-dose group significantly decreased ($P \leq 0.05$). Compared to the Kanglaite soft capsule group, the RBC level of mice in the cisplatin+GLP-2 low-dose and high-dose groups significantly decreased ($P \leq 0.05$ or $P \leq 0.01$). Compared to the cisplatin+Kanglaite soft capsule group, the blood WBC level in the mice of the cisplatin+GLP-2 high-dose group significantly increased ($P \leq 0.05$ or $P \leq 0.01$), with no statistical significance in other groups.

TABLE 20

Effect of Ganoderma lucidum polysaccharide GLP-2 combined with chemotherapy on blood biochemical indicators in orthotopic H22-bearing mice ($\bar{x} \pm s$)

| Group | WBC ($10^9$/L) | RBC ($10^{12}$/L) | ALT (U/L) | AST (UL) | BUN (mmol/L) | CRE (umol/L) |
|---|---|---|---|---|---|---|
| Normal control group | 6.81 ± 0.83 | 9.62 ± 0.16 | 49 ± 4 | 134 ± 18 | 8.10 ± 1.33 | 10.5 ± 09 |
| Model control group | 9.33 ± 1.29 | 9.18 ± 0.44 | 84 ± 31 | 761 ± 104$^{++}$ | 9.75 ± 1.51 | 19.8 ± 2.7$^+$ |
| Cisplatin group | 4.41 ± 1.83 | 8.91 ± 0.22 | 115 ± 39 | 771 ± 153 | 13.52 ± 4.94 | 18.9 ± 2.7 |
| Kanglaite soft capsule group | 6.16 ± 1.60 | 8.80 ± 0.15 | 72 ± 10 | 831 ± 148 | 8.42 ± 1.86 | 15.1 ± 1.7 |
| Cisplatin + Kanglaite soft capsule | 3.10 ± 0.51* | 8.54 ± 0.27 | 63 ± 21 | 431 ± 103 | 4.97 ± 2.08 | 22.2 ± 0.9 |
| Cisplatin + GLP-2 low-dose group | 4.84 ± 0.75* | 8.31 ± 0.21$^\&$ | 61 ± 11 | 735 ± 278 | 11.44 ± 2.55 | 15.5 ± 2.8 |
| Cisplatin + GLP-2 high-dove group | 5.29 ± 0.57* | 7.80 ± 0.64$^\&$ | 68 ± 9 | 640 ± 22 | 3.64 ± 1.11*$^\#$ | 20.4 ± 0.6 |

Note:
Compared to the normal control group, $^+P \leq 0.05$, $^{++}P \leq 0.01$; compared to the model control group, *$P \leq 0.05$, **$P \leq 0.01$; compared to the cisplatin group, $^\#P \leq 0.05$, $^{\#\#}P \leq 0.01$; compared to the Kanglaite soft capsule group, $^\&P \leq 0.05$, $^{\&\&}P \leq 0.01$; compared to the cisplatin + Kanglaite soft capsule group, $^\star P \leq 0.05$, $^{\star\star}P \leq 0.01$.

As shown in Table 21, compared to the normal control group, there was a trend of increased blood CD3$^+$/CD4$^+$ and CD3$^+$/CD8$^+$ ratios in the model control group of mice, though the differences were not statistically significant. Compared to the model control group, the blood CD3$^+$/CD8$^+$ ratio in the mice of the cisplatin+GLP-2 low-dose group significantly increased (P≤0.05); the blood CD3$^+$/CD4$^+$ and CD3$^+$/CD8$^+$ ratios in the mice of the cisplatin+GLP-2 high-dose group significantly increased (P≤0.05). Compared to the cisplatin group, the blood CD3$^+$/CD8$^+$ ratio in the mice of the cisplatin+GLP-2 low-dose group significantly increased (P≤0.05); the blood CD3$^+$/CD4$^+$ and CD3$^+$/CD8$^+$ ratios in the mice of the cisplatin+GLP-2 high-dose group significantly increased (P≤0.05). There was no significant statistical difference between groups compared to the Kanglaite soft capsule group. There was no significant statistical difference between groups compared to the cisplatin+Kanglaite soft capsule group.

TABLE 21

Effect of Ganoderma lucidum polysaccharide GLP-2 combined with chemotherapy on blood CD3$^+$/CD4$^+$ and CD3$^+$/CD8$^+$ ratios in orthotopic H22-bearing mice ($\bar{x} \pm s$)

| Group | CD3$^+$/CD4$^+$ | CD3$^+$/CD8$^+$ |
|---|---|---|
| Normal control group | 2.97 ± 0.12 | 3.62 ± 0.38 |
| Model control group | 4.76 ± 1.37 | 4.73 ± 0.75 |
| Cisplatin group | 4.26 ± 0.04 | 4.21 ± 0.81 |
| Kanglaite soft capsule group | 4.20 ± 0.70 | 6.58 ± 2.91 |
| Cisplatin + Kanglaite soft capsule group | 3.88 ± 0.88 | 9.58 ± 3.62 |
| Cisplatin + GLP-2 low-dose group | 6.23 ± 1.00 | 11.70± 1.50*$^\#$ |
| Cisplatin + GLP-2 high-dose group | 10.45± 2.74*$^\#$ | 16.81± 3.40*$^\#$ |

Note:
Compared to the model control group, *$P \leq 0.05$; compared to the cisplatin group, $^\#P \leq 0.05$; compared to the Kanglaite soft capsule group, $^\&P \leq 0.05$; compared to the cisplatin + Kanglaite soft capsule group, $^\star P \leq 0.05$.

As shown in FIGS. 39A-42G, the mice in the model control group exhibited extensive hepatocellular carcinoma cell infiltration and necrosis, increased number of sinusoidal cells, and inflammatory cell infiltration in the liver; evident extramedullary hematopoiesis and diffuse red pulp in the spleen, liver cancer cell infiltration in the stomach and lesions on the serosa, with widespread atrophy of the gastric mucosa. After administration of Ganoderma lucidum polysaccharide GLP-2 combined with cisplatin, the extent of liver cancer cell infiltration and necrosis decreased in all groups, with increased splenic extramedullary hematopoiesis, and no significant lesions observed in the stomach and kidneys.

As shown in FIGS. 39A-42G, the corresponding groups are as follows: A: normal group, B: model control group, C: cisplatin group, D: Kanglaite soft capsule group, E: cisplatin+Kanglaite soft capsule group, F: cisplatin+GLP-2 low-dose group, G: cisplatin+GLP-2 high-dose group

Conclusion

Ganoderma lucidum polysaccharide GLP-2 combined with cisplatin significantly inhibits the growth of tumors in orthotopic H22-bearing mice and demonstrates a notable synergistic effect.

Discussion and Conclusion

Liver cancer is a highly lethal malignancy, where current treatments involving surgical resection, chemotherapy, and radiotherapy merely delay symptoms, making complete cure extremely difficult. Liver cancer is notably resistant to chemotherapy, especially in cases of advanced liver cancer, where there is no reliable evidence proving that systemic chemotherapy can improve overall survival of patients with advanced liver cancer.

The results of this study showed that in the model control group of mice, tumor volume significantly increased, spleen and liver indices significantly increased, red blood cell counts in the blood significantly increased, white blood cell counts significantly decreased, and liver and kidney functions were significantly abnormal. These findings indicate a decline in lymphatic system function during tumor progression in the model control group of mice. After the last dose, Ganoderma lucidum polysaccharide GLP-2 combined with cisplatin significantly inhibited the growth of tumors in mice, significantly reduced the thymus index and spleen index, significantly reduced the number of red blood cells in the blood of mice, and significantly increased the number of white blood cells, with some recovery in liver and kidney function indicators. CD4$^+$T cells and CD8$^+$T cells mediate tumor immune responses, where CD8$^+$T cells are the main effector cells of tumor immunity. Results indicate that *Ganoderma lucidum* polysaccharide GLP-2 combined with cisplatin significantly increased CD3+/CD4+ and CD3+/CD8+ ratios in the mice's blood, suggesting that *Ganoderma lucidum* polysaccharide GLP-2 combined with cisplatin can protect immune organs and enhance the body's own immune function, thereby playing a role in reducing toxicity and enhancing antitumor effects. Histopathological results also showed that *Ganoderma lucidum* polysaccharide GLP-2 can enhance the body's immunity. Additionally, when compared to Kanglaite soft capsule combined with cisplatin, *Ganoderma lucidum* polysaccharide GLP-2 combined with cisplatin significantly reduced tumor, spleen indices, and thymus indices, indicating that *Ganoderma lucidum* polysaccharide GLP-2 combined with cisplatin has a stronger antitumor effect than Kanglaite soft capsule combined with cisplatin.

The foregoing description concerns merely exemplary embodiments of the present invention and is not intended to limit the invention. Any modifications, equivalent substitutions, and improvements made within the spirit and principles of the invention should be included within the scope of the invention's protection.

What is claimed is:

1. A type of *Ganoderma lucidum* polysaccharide GLP-2, wherein a molecular structural formula of the *Ganoderma lucidum* polysaccharide GLP-2 is

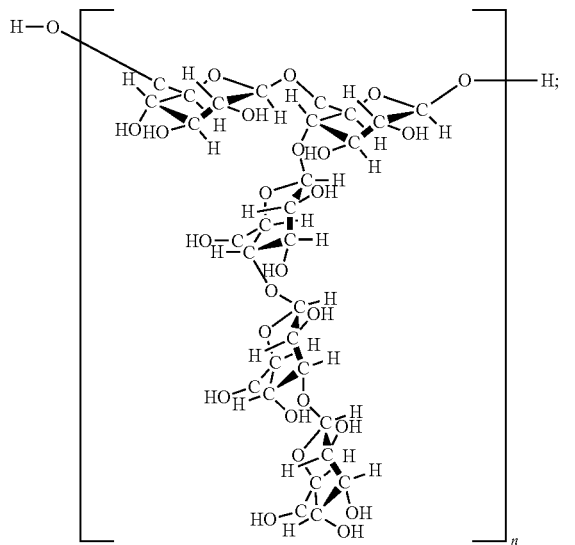

a molecular formula is: $(C_{30}H_{50}O_{25})_n$; a main chain of the *Ganoderma lucidum* polysaccharide GLP-2 is β-1,6 glucan, with β-D-Glcp-(1→3)-β-D-Glcp-(1→4)-β-D-Glcp-(1→ linked to the main chain through an O-4 bond of →4,6)-β-D-Glcp-(1→; a condensed structural formula is:

β-D-Glcp-(1→3)-β-D-Glcp-(1→4)-β-D-Glcp-(1→
|
4
→6)-β-D-Glcp-(1→6)-β-D-Glcp-(1→ , where n=92-147.

2. The *Ganoderma lucidum* polysaccharide GLP-2 according to claim 1, wherein n is selected from 92, 96, 100, 105, 110, 115, 120, 125, 130, 135, 140, 144, or 147.

3. A method for extracting the *Ganoderma lucidum* polysaccharide GLP-2 as claimed in claim 1, comprising the following steps of:
   S1. dusting and drying *Ganoderma lucidum*, then crushing *Ganoderma lucidum* to make *Ganoderma lucidum* powder;
   S2. placing the crushed *Ganoderma lucidum* powder in a sealed container mixed with water, heating under high temperature and pressure to fully dissolve the *Ganoderma lucidum* powder with the water into a medicinal juice solution;
   S3. using membrane concentration technology to separate the medicinal juice solution to obtain a concentrated solution with an active ingredient and not fully dissolved medicinal residue; and
   S4. mixing the concentrated solution containing the active ingredient with pure water to a water solution with a preset concentration, followed by multiple column chromatography separations to obtain the *Ganoderma lucidum* polysaccharide GLP-2 with the active ingredient.

4. The method for extracting *Ganoderma lucidum* polysaccharide GLP-2 according to claim 3, wherein in the step S2, the mixture of the *Ganoderma lucidum* powder and the water in the sealed container is fully stirred and heated at a high temperature to 105-200° C., with boiling time lasting for 2-6 h, during which the internal pressure in the sealed container gradually increases as the heating temperature rises, forming a high-temperature and high-pressure environment within the sealed container.

5. The method for extracting *Ganoderma lucidum* polysaccharide GLP-2 according to claim 4, wherein in the step S2, the mixture of the *Ganoderma lucidum* powder and the water in the sealed container is heated at a high temperature to 105-170° C., with boiling time lasting for 3-6 h, during which the internal pressure in the sealed container gradually increases as the heating temperature rises, forming the high-temperature and high-pressure environment within the sealed container.

6. The method for extracting the *Ganoderma lucidum* polysaccharide GLP-2 according to claim 5, wherein in the step S4, the concentrated liquid containing the active ingredient is mixed with the pure water at a concentration ratio of 1:2 to 1:5.

7. The method for extracting the *Ganoderma lucidum* polysaccharide GLP-2 according to claim 6, wherein in the step S3, *Ganoderma lucidum* residue is removed from the extracted water solution containing the active ingredient by using the membrane concentration technology, obtaining a concentrated liquid or paste containing the active ingredient.

8. The method for extracting the *Ganoderma lucidum* polysaccharide GLP-2 according to claim 7, wherein in the step S1, the *Ganoderma lucidum* is rinsed with clean water to remove surface dust and dried at 105° C., and the dried *Ganoderma lucidum* is crushed, with the crushed *Ganoderma lucidum* powder being larger than 60 mesh.

9. The method for extracting the *Ganoderma lucidum* polysaccharide GLP-2 according to claim 8, wherein in the step S2, the mixed liquid in the sealed container is heated at a high temperature to 105° C., 110° C., 115° C., 125° C., 130° C., 135° C., 140° C., 145° C., 155° C., 160° C., 165° C., or 170° C., with boiling times of 3 h, 3.5 h, 4 h, 4.5 h, 5 h, 5.5 h, or 6 h, during which the internal pressure in the sealed container gradually increases as the heating temperature rises, forming the high-temperature and high-pressure environment within the sealed container.

10. The method for extracting the *Ganoderma lucidum* polysaccharide GLP-2 according to claim 4, wherein in the step S2, the mixed liquid in the sealed container is heated at a high temperature to 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C., with boiling times of 2 h, 2.5 h, 3 h, 3.5 h, 4 h, 4.5 h, 5 h, 5.5 h, or 6 h, during which the internal pressure in the sealed container gradually increases as the heating temperature rises, forming the high-temperature and high-pressure environment within the sealed container.

11. A method of treating lung cancer or liver cancer in a subject in need thereof, said method comprising administering an effective amount of the combination of cisplatin with the *Ganoderma lucidum* polysaccharide GLP-2 according to claim 1, said combination alleviates toxic side effects caused by chemotherapy drugs on the subject, controls and reduces tumor masses, and a reduces and eliminates cancer cells.

12. A method of treating lung cancer or liver cancer in a subject in need thereof, said method comprising administering an effective amount of the combination of cisplatin with the *Ganoderma lucidum* polysaccharide GLP-2 according to claim 2, said combination alleviates toxic side effects caused by chemotherapy drugs on the subject, controls and reduces tumor masses, and a reduces and eliminates cancer cells.

13. A method for extracting the *Ganoderma lucidum* polysaccharide GLP-2 as claimed in claim 2, comprising the following steps of:
  S1. dusting and drying *Ganoderma lucidum*, then crushing *Ganoderma lucidum* to make *Ganoderma lucidum* powder;
  S2. placing the crushed *Ganoderma lucidum* powder in a sealed container mixed with water, heating under high temperature and pressure to fully dissolve the *Ganoderma lucidum* powder with the water into a medicinal juice solution;
  S3. using membrane concentration technology to separate the medicinal juice solution to obtain a concentrated solution with an active ingredient and not fully dissolved medicinal residue; and
  S4. mixing the concentrated solution containing the active ingredient with pure water to a water solution with a preset concentration, followed by multiple column chromatography separations to obtain the *Ganoderma lucidum* polysaccharide GLP-2 with the active ingredient.

* * * * *